(12) United States Patent
Kearney et al.

(10) Patent No.: US 8,053,454 B2
(45) Date of Patent: Nov. 8, 2011

(54) PYRIDOPYRIMIDINONE INHIBITORS OF PIM-1 AND/OR PIM-3

(75) Inventors: Patrick Kearney, San Francisco, CA (US); S. David Brown, San Carlos, CA (US); Elena S. Koltun, Foster City, CA (US)

(73) Assignee: Exelixis, Inc., South San Francisco, CA (US)

( * ) Notice: Subject to any disclaimer, the term of this patent is extended or adjusted under 35 U.S.C. 154(b) by 328 days.

(21) Appl. No.: 12/088,474

(22) PCT Filed: Oct. 5, 2006

(86) PCT No.: PCT/US2006/039568
§ 371 (c)(1),
(2), (4) Date: Jul. 29, 2008

(87) PCT Pub. No.: WO2007/044724
PCT Pub. Date: Apr. 19, 2007

(65) Prior Publication Data
US 2009/0042918 A1    Feb. 12, 2009

Related U.S. Application Data

(60) Provisional application No. 60/724,171, filed on Oct. 6, 2005.

(51) Int. Cl.
*A61K 31/41* (2006.01)
*C07D 247/00* (2006.01)
(52) U.S. Cl. .................................. 514/381; 548/250
(58) Field of Classification Search .................. 514/381; 548/250
See application file for complete search history.

(56) References Cited

U.S. PATENT DOCUMENTS

| | | | |
|---|---|---|---|
| 3,636,094 A | 1/1972 | Yonan | |
| 2004/0142981 A1* | 7/2004 | Thorarensen et al. | ........ 514/355 |

FOREIGN PATENT DOCUMENTS

| | | |
|---|---|---|
| EP | 0 628 555 A | 12/1994 |
| GB | 1 276 359 A | 6/1972 |
| JP | 62/012753 A | 1/1987 |
| JP | 62/255458 A | 11/1987 |
| JP | 04/342577 A | 11/1992 |
| WO | 02/50031 A | 6/2002 |
| WO | 2004/022525 A | 3/2004 |
| WO | 2004/022529 A | 3/2004 |
| WO | WO 2004/022525 * | 3/2004 |
| WO | 2004/034972 A | 4/2004 |
| WO | 2004/046090 A | 6/2004 |
| WO | 2004/046140 A | 6/2004 |
| WO | 2004/058769 A | 7/2004 |

OTHER PUBLICATIONS

Patini, et al., Chem. Rev., 1996, 96, 3147-3176, esp. pp. 3146 and 3147.*

Valgeirsson, Jon et al., "Bioisosteric Modifications of 2-Arylureidobenzoic Acids: Selective Noncompetitive Antagonists for the Homomeric Kainate Receptor Subtype GluR5", Journal of Medicinal Chemistry, 2004, 47(27), 6948-6957.
Valgeirsson, Jon et al., "2-Arylureidobenzoic Acids: Selective Noncompetitive Antagonists for the Homomeric Kainate Receptor Subtype GluR5", Journal of Medicinal Chemistry, 2003, 46(26), 5834-5843.
Biagi, Giuliana et al., "Some structural changes on triazolyl-benotriazoles and triazolyl-benzimidazolones as potential potassium channel activators. III", Farmaco, 2001, 56(11), 841-849.
Avotin'sh, F. M. et al., "2-[(3-Ethyl-2,2-dimethylcyclobutyl)methyl]-4(3H)-quinazolinones", Chemistry of Heterocyclic Compounds, 1999, 35(6), 722-728.
Osborne, A. G. et al., "1H and 13C NMR spectral studies of some 4H-3,1-benzoxazin-4-ones and their 2-acylaminobenzoic acid precursors", Spectrochimica Acta, Part A: Molecular and Biomolecular Spectroscopy, 2000, 56A(6), 1079-1100.
Johnson, Judith L. et al., "Synthesis of NSC-341,964: an unexpected study on the stability of 2-aryl-4H-3,1-benzoxazin-4-ones", Journal of Heterocyclic Chemistry, 1986, 23(1), 249-251.
Ryznerski, Zygmunt et al., "Synthesis and antiinflammatory properties of N-(2-carboxyphenyl)phenoxyacetamides", Chemical Abstract Service, XP002425195, Database accession No. 1980:567828.
Sunder, Shyam et al., "Synthesis of benzofuro[3,2-b]quinolin-6(11H)one and derivatives", Journal of Heterocyclic Chemistry, 1978, 15(8), 1379-1382.
Heyman, Duane A., "Preparation of isatoates from isatoic anhydride", Journal of Heterocyclic Chemistry, 1978, 15(7), 1131-1136.
Archer, John G. et al., "1,2,3-Benzotrianzin-4-ones and related systems. II. Thermolytic decomposition of substituted 1,2,3-benzotriazin-4-ones and isatoic anhydrides", Journal of the Chemical Society, Perkin Transactions 1: Organic and Bio-Organic Chemistry, 1972-1999, vol. 11, 1169-1173.
Felix, Arthur M. et al., "Synthesis and diuretic properties of some N-alkylaminocarbonyl- and N-pyrrolylcarbonylanthranilic acid derivatives", Journal of Medicinal Chemistry, 1969, 12(3), 384-387.
Itami, Yasuo et al., "Preparation of herbicidal fluorinated alkanecarboxamides.", Chemical Abstracts Service, Columbus, Ohio, XP002425196, Database accession No. 1988:200216.

* cited by examiner

*Primary Examiner* — Susannah Chung
(74) *Attorney, Agent, or Firm* — McDonnell Boehnen Hulbert & Berghoff LLP

(57) ABSTRACT

Compounds of formula (I), useful for inhibiting PIM-I and/or PIM-3: and pharmaceutically acceptable salts thereof, wherein Y, Z, $R_1$, $R_3$, Q, X and $R_4$ are as defined above. Pharmaceutical compositions and methods of treating diseases and conditions, such as cancer, are also disclosed.

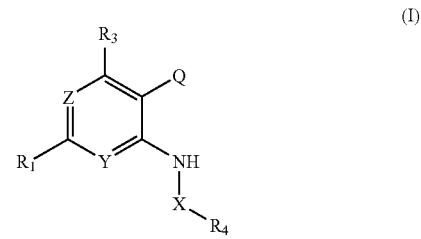

10 Claims, No Drawings

PYRIDOPYRIMIDINONE INHIBITORS OF PIM-1 AND/OR PIM-3

This application is a US national phase of international application PCT/US2006/039568, filed on Oct. 5, 2006, which claims the benefit of U.S. provisional application Ser. No. 60/724,171 filed on Oct. 6, 2005.

BACKGROUND OF THE INVENTION

1. Field of the Invention

The invention relates to compounds for inhibiting PIM-1, PIM-3, or a combination thereof, pharmaceutical compositions of such compounds, and methods of treating diseases or conditions responsive to inhibition of PIM-1, PIM-3, or a combination thereof.

2. Summary of the Related Art

The PIM protein kinase family which consists of the closely related PIM-1, 2, and 3, have been implicated in diverse biological processes such as cell survival, proliferation, and differentiation. PIM-1 is involved in a number of signaling pathways that are highly relevant to tumorigenesis [reviewed in Bachmann & Moroy, Internat. J. Biochem. Cell Biol., 37, 726-730 (2005)]. Many of these are involved in cell cycle progression and apoptosis. It has been shown that PIM-1 acts as an anti-apoptotic factor via inactivation of the pro-apoptotic factor Bad. This finding suggested a direct role of PIM-1 in preventing cell death since the inactivation of Bad can enhance Bcl-2 activity and thereby promotes cell survival [Aho et al., FEBS Letters, 571, 43-49 (2004)]. PIM-1 has also been recognized as a positive regulator of cell cycle progression. PIM-1 binds and phosphorylates CDC25A, which leads to an increase in its phosphatase activity and promotion of G1/S transition [reviewed in Losman et al., JBC, 278, 4800-4805 (1999)]. In addition, the cyclin kinase inhibitor p21$^{Waf}$ which inhibits G1/S progression was found to be inactivated by PIM-1 [Wang et al., Biochim. Biophys. Act. 1593, 45-55 (2002)]. Furthermore, by means of phosphorylation, Pim-1 inactivates C-TAK1 and activates Cdc25C which results in acceleration of G2/M transition [Bachman et al., JBC, 279, 48319-48 (2004)].

PIM-1 appears to be an essential player in hematopoetic proliferation. Kinase active PIM-1 is required for the gp130-mediated STAT3 proliferation signal [Hirano et al., Oncogene 19, 2548-2556, (2000)] PIM-1 is overexpressed or even mutated in a number of tumors and different types of tumor cell lines and leads to genomic instability. Examples for a possible involvement of PIM-1 in human tumors are prostate cancer, oral cancer, and Burkitt lymphoma (Gaidano & Dalla Faver, 1993). All these findings point to an important role of PIM-1 in the initiation and progression of human cancer, and it appears that small molecule inhibition of PIM-1 activity is a promising therapeutic strategy. Finally, PIM-2 and PIM-3 have overlapping functions with PIM-1 and inhibition of more than one isoform may provide additional therapeutic benefits.

The implication of a role for PIM-3 in cancer was first suggested by transcriptional profiling experiments showing that PIM3 gene transcription was upregulated in EWS/ETS-induced malignant transformation of NIH 3T3 cells. These results were extended to show that PIM-3 is selectively expressed in human and mouse hepatocellular and pancreatic carcinomas but not in normal liver or pancreatic tissues. In addition, PIM-3 mRNA and protein are constitutively expressed in multiple human pancreatic and hepatocellular cancer cell lines.

The link between PIM-3 overexpression and a functional role in promoting tumorigenesis came from RNAi studies in human pancreatic and hepatocellular cancer cell lines overexpressing PIM-3. In these studies the ablation of endogenous PIM-3 protein promoted apoptosis of these cells. The molecular mechanism by which PIM-3 suppresses apoptosis is in part carried out through the modulation of phosphorylation of the pro-apoptotic protein BAD. Similar to both PIM1&2 which phosphorylate BAD protein, the knockdown of PIM-3 protein by siRNA results in a decrease in BAD phosphorylation at Ser112. Thus, similar to PIM1&2, PIM-3 acts a suppressor of apoptosis in cancers of endodermal origin, pancreatic and liver. Moreover, as conventional therapies in pancreatic cancer have a poor clinical outcome, PIM-3 could represent a new important molecular target towards successful control of this incurable disease.

Accordingly, the identification of compounds that specifically inhibit, regulate and/or modulate the signal transduction of PIM-1 and/or PIM-3, is desirable as a means to treat or prevent disease states associated with abnormal cell proliferation, such as cancer, and is an object of this invention.

SUMMARY OF THE INVENTION

The present invention provides compounds for the inhibition of PIM-1 and/or PIM-3. The compounds of the invention have general structural formula I:

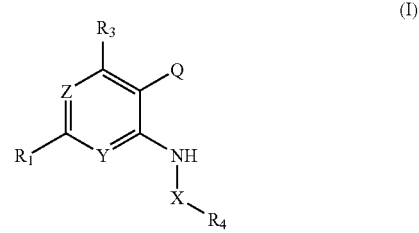

wherein the variables are defined below.

In other aspects, the invention provides a pharmaceutical composition of a compound of formula I, a method of inhibiting the in vivo activity of PIM-1 and/or PIM-3 using a compound of formula I, and a method of treating proliferative disease with a compound of formula I.

The foregoing merely summarizes certain aspects of the invention and is not intended to be limiting in nature. These aspects and other aspects and embodiments are described more fully below. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

DETAILED DESCRIPTION OF THE INVENTION

In one aspect, the invention provides compounds of formula (I) that are useful as inhibitors of PIM-1 and/or PIM-3:

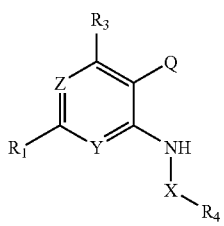

(I)

or pharmaceutically acceptable salts thereof, wherein

Q is tetrazolyl, carboxyl, or hydroxamic acid;

X is absent or —C(O)—;

Y is N or $CR_5$;

Z is N or $CR_2$;

$R_1$, $R_2$, and $R_3$ are independently H, halogen, $C_1$-$C_6$ haloalkyl, $C_1$-$C_6$ haloalkoxy, $C_1$-$C_6$ alkyl, $C_0$-$C_6$ alkyl $CR_7$, $C_1$-$C_6$ alkoxy, $C_1$-$C_6$ alkylcarbonyl, or $C_1$-$C_6$ alkylC(O)$OR_6$;

$R_6$ and $R_7$ at each occurrence are independently H, $C_1$-$C_6$ alkyl, $C_2$-$C_6$ alkanoyl, aryl (such as phenyl or naphthyl) or aryl $C_1$-$C_6$ alkyl (such as benzyl or phenethyl); or when Z is carbon then Z, $R_2$, $R_1$, and the carbon to which $R_1$ is attached may form a five membered ring containing 0, 1, or 2 nitrogens, where the five membered ring is aromatic or non-aromatic; and is unsubstituted or substituted with 1 or 2 groups that are independently $C_1$-$C_6$ alkyl, $C_1$-$C_6$ alkoxy, halogen, $C_1$-$C_6$ haloalkyl or $C_1$-$C_6$ haloalkoxy;

$R_5$ is H, $C_1$-$C_6$ alkyl, halogen, $C_1$-$C_6$ haloalkyl or $C_1$-$C_6$ haloalkoxy; and $R_4$ is $C_1$-$C_8$ alkyl, $NR_6R_7$, $C_1$-$C_6$ alkoxy, $C_1$-$C_6$ alkyl C(O)$OR_6$, aryl, aryl $C_1$-$C_6$ alkyl, heteroaryl, heteroaryl $C_1$-$C_6$ alkyl, heterocycloalkyl, heterocycloalkyl $C_1$-$C_6$ alkyl, cycloalkyl, or cycloalkyl $C_1$-$C_6$ alkyl, each of which is optionally substituted with one or more groups, where each group is independently $C_1$-$C_6$ alkyl, $C_1$-$C_6$ alkoxy, $C_2$-$C_4$ alkenyl, $C_1$-$C_6$ alkylcarbonyl, $C_0$-$C_6$ alkylC(O)$OR_6$, halogen, $C_1$-$C_6$ haloalkyl, $C_1$-$C_6$ haloalkoxy, $C_1$-$C_6$ alkoxy $C_1$-$C_6$ alkyl, $C_0$-$C_6$ alkyl $NR_6R_7$, —$SO_2$—($C_1$-$C_4$ alkyl), —S—($C_1$-$C_4$ alkyl), $C_2$-$C_6$ alkanoyl, aryl, —O-aryl, heteroaryl, heterocycloalkyl, cycloalkyl, $C_1$-$C_6$ alkoxycarbonyl, or $C_1$-$C_6$ alkyl substituted with $C_1$-$C_6$ alkoxycarbonyl, where the alkyl, alkoxy, heterocycloalkyl or cycloalkyl portions of $R_4$ may further be substituted with one or more oxo groups; and where each aryl, heteroaryl, heterocycloalkyl, cycloalkyl substituent of $R_4$ above is optionally substituted with one or more groups, where each group is independently halogen, $C_1$-$C_6$ haloalkyl, $C_1$-$C_6$ haloalkoxy, $C_1$-$C_6$ alkyl, $C_1$-$C_6$ alkoxy, hydroxy, $NR_6R_7$, 4-methylpiperazin-1-yl, $CF_3$, $OCF_3$, $C_2$-$C_6$ alkanoyl, or $C_1$-$C_6$ alkyl substituted with $C_1$-$C_6$ alkoxycarbonyl.

In one embodiment, the invention provides compounds of formula I-1, i.e., compound of formula I where X is —C(O)—.

In another embodiment, the invention provides compounds of formula I-2, i.e., compound of formula I-1 where $R_4$ is $C_1$-$C_7$ alkyl, which is optionally substituted with one or more groups, where each group is independently $C_1$-$C_6$ alkoxy, halogen, $C_1$-$C_4$ haloalkyl, $C_1$-$C_4$ haloalkoxy, $C_1$-$C_6$ alkoxy $C_1$-$C_6$ alkyl, $C_2$-$C_4$ alkenyl, $NR_6R_7$, —$C_0$-$C_6$ alkylC(O)$OR_6$, —O-aryl or aryl, where the aryl (such as phenyl) is Optionally substituted with one or more groups, where each group is independently halogen, $C_1$-$C_4$ haloalkyl, $C_1$-$C_4$ haloalkoxy, $C_1$-$C_6$ alkyl, $C_1$-$C_6$ alkoxy, hydroxy, $NR_6R_7$, 4-methylpiperazin-1-yl, $CF_3$, $OCF_3$, $C_2$-$C_6$ alkanoyl, or $C_1$-$C_6$ alkyl substituted with $C_1$-$C_6$ alkoxycarbonyl.

In still another embodiment, the invention provides compounds of formula I-3, i.e., compound of formula I-2 where Y is $CR_5$; Z is $CR_2$; and $R_2$ and $R_5$ are independently H or halogen.

In yet another embodiment, the invention provides compounds of formula I-4, i.e., compound of formula I-3 where, $R_1$, $R_2$, and $R_3$ are independently H, chloro, bromo, methyl, $NR_6R_7$, or methoxy; and $R_6$ and $R_7$ at each occurrence are independently H, $C_1$-$C_4$ alkyl, $C_2$-$C_4$ alkanoyl, or phenyl$C_1$-$C_4$ alkyl.

In still yet another embodiment, the invention provides compounds of formula I-5, i.e., compound of formula I-4 where $R_4$ is isopropyl, n-butyl, sec-butyl, isobutyl, tert-butyl, 3-pentyl, propyl, ethyl, isopentyl, methoxymethyl, propyl substituted with phenyl, —($C_1$-$C_4$ alkyl)-$NR_6R_7$, where $R_6$ and $R_7$ are independently H, or $C_1$-$C_4$ alkyl (such as Me); or $C_1$-$C_2$ alkyl substituted with $C_1$-$C_4$ alkoxycarbonyl.

In still another embodiment, the invention provides compounds of formula I-6, i.e., compound of formula I-5 where Q is tetrazolyl.

In yet another embodiment, the invention provides compounds of formula I-7, i.e., compound of formula I-5 where Q is carboxyl.

In still yet another embodiment, the invention provides compounds of formula I-8, i.e., compound of formula I-1 where $R_4$ is $C_1$-$C_7$ alkyl, which is optionally substituted with $C_2$-$C_4$ alkenyl, $C_1$-$C_4$ alkoxy, $NR_6R_7$, —$C_0$-$C_6$ alkylC(O)$OR_6$, —O-phenyl where the phenyl is optionally substituted with 1, 2, or 3 groups that are independently, halogen, $C_1$-$C_4$ alkyl, $C_1$-$C_4$ alkoxy, hydroxyl, 4-methylpiperazin-1-yl, $CF_3$, or $OCF_3$.

In still another embodiment, the invention provides compounds of formula I-9, i.e., compound of formula I-1 where $R_4$ is $C_2$-$C_4$ alkyl substituted with $C_2$-$C_4$ alkenyl. In one aspect, $R_4$ is —$CH_2CH_2CH=CH_2$.

In still yet another embodiment, the invention provides compounds of formula I-10, i.e., compound of formula I-1 where $R_4$ is $C_2$-$C_4$ alkyl substituted with $C_1$-$C_3$ alkoxy.

In yet another embodiment, the invention provides compounds of formula I-11, i.e., compound of formula I-1 where $R_4$ is $C_2$-$C_4$ alkyl substituted with $NR_6R_7$, where $R_6$ and $R_7$ are independently H or $C_1$-$C_4$ alkyl. In one aspect, $NR_6R_7$ is $NH_2$. In another aspect, $NR_6R_7$ is $NMe_2$.

In yet another embodiment, the invention provides compounds of formula I-12, i.e., compound of formula I-1 where $R_4$ is $C_2$-$C_4$ alkyl substituted with $C_0$-$C_6$ alkylC(O)$OR_6$, where $R_6$ is H or $C_1$-$C_3$ alkyl.

In yet another embodiment, the invention provides compounds of formula I-13, i.e., compound of formula I-1 where $R_4$ is $C_1$-$C_4$ alkyl substituted with —O-phenyl where the phenyl is unsubstituted.

In yet still another embodiment, the invention provides compounds of formula I-14, i.e., compound of formula I-1 where $R_4$ is $C_1$-$C_4$ alkyl substituted with —O-phenyl where the phenyl is optionally substituted with 1, 2, or 3 groups that are independently, halogen, $C_1$-$C_4$ alkyl, $C_1$-$C_4$ alkoxy, hydroxyl, 4-methylpiperazin-1-yl, $CF_3$, or $OCF_3$.

In yet another embodiment, the invention provides compounds of formula I-15, i.e., compound of formula I-1 where $R_4$ is $C_1$-$C_2$ alkyl substituted with —O-phenyl where the phenyl is substituted with 1, 2, or 3 groups that are independently, halogen (such as Cl), $C_1$-$C_4$ alkyl (such as methyl), $C_1$-$C_4$ alkoxy (such as methoxy), hydroxyl, 4-methylpiperazin-1-yl, $CF_3$, or $OCF_3$. In one aspect, the phenyl is mono-substituted.

In still another embodiment, the invention provides compounds of formula I-16, i.e., compound of formula I-1 where $R_4$ is $C_1$ alkyl substituted with —O-phenyl where the phenyl is substituted with 1, or 2 groups that are independently, halogen (such as Cl), $C_1$-$C_4$ alkyl (such as methyl), $C_1$-$C_4$ alkoxy (such as methoxy), or hydroxyl.

In yet still another embodiment, the invention provides compounds of formula I-17, i.e., compounds according to formula I-8, where $R_4$ is unsubstituted $C_2$-$C_7$ alkyl.

In yet still another embodiment, the invention provides compounds of formula I-18, i.e., compounds according to formula I-20, where $R_4$ is ethyl, isopropyl, isobutyl, tert-butyl, sec butyl, n-butyl, isopentyl, pent-3-yl, pent-2-yl, or n-heptyl.

In yet another embodiment, the invention provides compounds of formula I-19, i.e., compounds according to any one of formulas I-8, I-9, I-10, I-11, I-12, I-13, I-14, I-15, I-16, I-17, or I-18, where Y and Z are both CH; $R_3$ is H and Q is tetrazolyl.

In still yet another embodiment, the invention provides compounds of formula I-20, i.e., compounds according to any one of formulas I-8, I-9, I-10, I-11, I-12, I-13, I-14, I-15, I-16, I-17, or I-18, where Y and Z are both CH; $R_3$ is H and Q is carboxyl.

In still yet another embodiment, the invention provides compounds of formula I-21, i.e., compounds according to any one of formulas I-8, I-9, I-10, I-11, I-12, I-13, I-14, I-15, I-16, I-17, I-18, I-19, or I-20, where $R_1$ is halogen (in one aspect, chloro).

In another embodiment, the invention provides compounds of formula II, i.e., compound of formula I-1 where $R_4$ is aryl, or aryl $C_1$-$C_6$ alkyl, wherein each is optionally substituted with one or more groups, where each group is independently $C_1$-$C_6$ alkyl, $C_1$-$C_6$ alkoxy, halogen, $C_1$-$C_6$ haloalkyl, $C_1$-$C_6$ haloalkoxy, $C_1$-$C_6$ alkoxy $C_1$-$C_6$ alkyl, $NR_6R_7$, $C_2$-$C_6$ alkanoyl, aryl, or $C_1$-$C_6$ alkyl substituted with $C_1$-$C_6$ alkoxycarbonyl, where the aryl is selected from phenyl and naphthyl, and where the aryl is optionally substituted with one or more groups, where each group is independently halogen, $C_1$-$C_6$ haloalkyl, $C_1$-$C_6$ haloalkoxy, $C_1$-$C_6$ alkyl (such as methyl), $C_1$-$C_6$ alkoxy (such as methoxy), hydroxy, $NR_6R_7$, 4-methylpiperazin-1-yl, $CF_3$, $OCF_3$, $C_2$-$C_6$ alkanoyl, or $C_1$-$C_6$ alkyl substituted with $C_1$-$C_6$ alkoxycarbonyl.

In still yet an embodiment, the invention provides compounds of formula II-1, i.e., compound of formula II, where Y is $CR_5$; Z is $CR_2$; and $R_2$ and $R_5$ are independently H or halogen.

In yet another embodiment the invention provides compounds of formula II-2, i.e., compound of formula II-1, $R_1$, $R_2$, and $R_3$ are independently chloro, bromo, iodo, fluoro, methyl, $NR_6R_7$, or methoxy; where $R_6$ and $R_7$ at each occurrence are independently H, $C_1$-$C_4$ alkyl, $C_2$-$C_4$ alkanoyl, or phenyl$C_1$-$C_4$ alkyl.

In still another embodiment, the invention provides compounds of formula II-3, i.e., compound of formula II-2, $R_4$ is phenyl, naphthyl, phenyl $C_1$-$C_4$ alkyl, or naphthyl $C_1$-$C_4$ alkyl, each of which is optionally substituted with 1, 2, or 3 halogens (fluoro, chloro, iodo, bromo), $C_1$-$C_4$ alkoxy (methoxy), $NR_6R_7$ (such as —NHC(O)CH$_3$); where $R_6$ and $R_7$ are independently H, $C_1$-$C_4$ alkyl, or $C_2$-$C_4$ alkanoyl.

In yet still another embodiment, the invention provides compounds of formula II-4, i.e., compound of formula II-3, where $R_4$ is phenyl, or phenyl $C_1$-$C_2$ alkyl, where each phenyl is optionally substituted with 1, 2, or 3 halogens, where each halogen is independently fluoro, chloro, bromo or iodo, or methoxy, or —NHC(O)CH$_3$. Alternatively, $R_4$ is benzyl or phenethyl each of which is unsubstituted or substituted with 1 or 2 halogens. In one aspect, a preferred halogen is bromo.

In still yet another embodiment, the invention provides compounds of formula II-5, i.e., compound of formula II-3, where, $R_4$ is naphthyl, or naphthyl $C_1$-$C_2$ alkyl, where each naphthyl is optionally substituted with 1, 2, or 3 halogens selected from fluoro, chloro, bromo or iodo, or methoxy, or —NHC(O)CH$_3$.

In yet another embodiment, the invention provides compounds of formula II-6, i.e., compound of formula II-4, where Q is tetrazolyl.

In yet another embodiment, the invention provides compounds of formula II-7, i.e., compound of formula II-4, where Q is carboxyl.

In still yet another embodiment, the invention provides compounds of formula II-8, i.e., compound of formula II where $R_4$ is phenyl or phenyl $C_1$-$C_4$ alkyl, where the phenyl portion of each is optionally substituted with 1 or 2 groups, each of which is independently halogen, $C_1$-$C_4$ alkyl, $C_1$-$C_4$ alkoxy, $C_1$-$C_2$ haloalkyl, or $C_1$-$C_2$ haloalkoxy.

In yet still another embodiment, the invention provides compounds of formula II-9, i.e., compound of formula II-8 where $R_1$ is halogen (in one aspect, chloro).

In another embodiment, the invention provides compounds of formula II-10, i.e., compound of formula II-9 where at least one of Y and Z is CH.

In yet another embodiment, the invention provides compounds of formula II-11, i.e., compound of formula II-10 where $R_3$ is H or F.

In yet another embodiment, the invention provides compounds of formula II-12, i.e., compound of formula II-11 where Y and Z are both CH; $R_3$ is H and Q is tetrazolyl.

In still yet another embodiment, the invention provides compounds of formula II-13, i.e., compound of formula II-11 where Y and Z are both CH; $R_3$ is H and Q is carboxyl.

In yet still another embodiment, the invention provides compounds of formula II-14, i.e., compounds according to any one of formulas II-8, II-9, II-10, II-11, II-12, or II-13 where the phenyl portion of $R_4$ is unsubstituted.

In still another embodiment, the invention provides compounds of formula I-15, i.e., compounds according to any one of formulas II-8, II-9, II-10, II-11, II-12, or II-13 where the phenyl portion of $R_4$ is substituted with at least one halogen.

In another embodiment, the invention provides compounds of formula II-16, i.e., compounds according to any one of formulas II-8, II-9, II-10, II-11, II-12, or II-13 where the phenyl portion of $R_4$ is substituted with two groups, where each group is independently halogen, $CF_3$, $OCF_3$, methyl or methoxy. (in one aspect, in the 3,5-positions, in another aspect, in the 2,4-positions, in another aspect, the 2,6-positions). In one aspect, the two halogens are both fluoro or both chloro.

In another embodiment, the invention provides compounds of formula II-17, i.e., compounds according to any one of formulas II-8, II-9, II-10, II-11, II-12, or II-13 where the phenyl portion of $R_4$ is substituted with one group that is halogen (such as F or Cl), $CF_3$, $OCF_3$, methyl or methoxy.

In another embodiment, the invention provides compounds of formula II-18, i.e., compounds according to any one of formulas II-8, II-9, II-10, II-11, II-12, or II-13 where the phenyl portion of $R_4$ is substituted at the 2-position with a group that is fluoro, bromo, methyl, or methoxy.

In another embodiment, the invention provides compounds of formula II-19, i.e., compounds according to any one of formulas II-8, II-9, II-10, II-11, II-12, or II-13 where the phenyl portion of $R_4$ is substituted at the 3-position with a group that is methoxy, chloro, fluoro, bromo, or methyl.

In another embodiment, the invention provides compounds of formula II-20, i.e., compounds according to any one of formulas II-8, II-9, II-10, II-11, II-12, or II-13 where the phenyl portion of $R_4$ is substituted at the 4-position with a group that is methoxy, fluoro, or chloro.

In another embodiment, the invention provides compounds of formula II-21, i.e., compounds according to any one of formulas II-14, II-15, II-16, II-17, II-18, II-19, or II-20 where $R_4$ is an optionally substituted phenyl.

In another embodiment, the invention provides compounds of formula II-22, i.e., compounds according to any one of formulas II-14, II-15, II-16, II-17, II-18, II-19, or II-20 where $R_4$ is an optionally substituted phenyl $C_1$-$C_4$ alkyl. In one aspect, $R_4$ is an optionally substituted phenyl $C_1$-$C_2$ alkyl. In still another aspect, $R_4$ is an optionally substituted benzyl.

In another embodiment, the invention provides compounds of formula III, i.e., compound of formula I-1, where $R_4$ is heteroaryl or heteroaryl $C_1$-$C_6$ alkyl, each of which is optionally substituted with one or more groups, where each group is independently $C_1$-$C_6$ alkyl, $C_1$-$C_6$ alkoxy, halogen, —$SO_2$—($C_1$-$C_4$ alkyl), —S—($C_1$-$C_4$ alkyl), $C_1$-$C_6$ haloalkyl, $C_1$-$C_6$ haloalkoxy, $C_1$-$C_6$ alkoxy $C_1$-$C_6$ alkyl, $NR_6R_7$, $C_2$-$C_6$ alkanoyl, aryl, or $C_1$-$C_6$ alkyl substituted with $C_1$-$C_6$ alkoxycarbonyl, where the aryl is selected from phenyl and naphthyl, and where the aryl is optionally substituted with one or more groups, where each group is independently halogen, $C_1$-$C_6$ haloalkyl, $C_1$-$C_6$ haloalkoxy, $C_1$-$C_6$ alkyl (such as methyl), $C_1$-$C_6$ alkoxy (such as methoxy), hydroxy, $NR_6R_7$, 4-methylpiperazin-1-yl, $CF_3$, $OCF_3$, $C_2$-$C_6$ alkanoyl, or $C_1$-$C_6$ alkyl substituted with $C_1$-$C_6$ alkoxycarbonyl.

In still another embodiment, the invention provides compounds of formula III-1, i.e., compound of formula III, where Y is $CR_5$; Z is $CR_2$; and $R_2$ and $R_5$ are independently H or halogen.

In still yet another embodiment, the invention provides compounds of formula III-2, i.e., compound of formula III-1, $R_1$ and $R_3$ are independently H, chloro, bromo, methyl, $NR_6R_7$, or methoxy; and where $R_6$ and $R_7$ at each occurrence are independently H, $C_1$-$C_4$ alkyl, $C_2$-$C_4$ alkanoyl, or phenyl $C_1$-$C_4$ alkyl.

In yet another embodiment, the invention provides compounds of formula III-3, i.e., compound of formula III-2, where $R_4$ is heteroaryl or heteroaryl $C_1$-$C_6$ alkyl, where the heteroaryl group is thienyl, thiadiazolyl, oxazolyl, benzothienyl, isoxazolyl, benzofuranyl, pyridyl, pyrazolyl, or furanyl, each of which is optionally substituted with one or more groups, where each group is independently halogen (such as chloro), $C_1$-$C_4$ alkyl, —$SO_2$—($C_1$-$C_4$ alkyl), —S—($C_1$-$C_4$ alkyl), $C_1$-$C_4$ alkoxy, or aryl (such as phenyl), where the aryl is optionally substituted with one or more groups, where each group is independently halogen, $C_1$-$C_4$ haloalkyl, $C_1$-$C_4$ haloalkoxy, $C_1$-$C_4$ alkyl, $C_1$-$C_4$ alkoxy (such as methoxy), or hydroxy.

In yet still another embodiment, the invention provides compounds of formula III-4, i.e., compound of formula III-3, where the heteroaryl portion of the heteroaryl or heteroaryl $C_1$-$C_6$ alkyl group is thienyl optionally substituted with one halogen (such as chloro), two halogens (which are the same or different), or with aryl (such as phenyl), where the aryl (such as phenyl) is optionally substituted with one or more groups that are independently halogen, $C_1$-$C_4$ haloalkyl, $C_1$-$C_4$ haloalkoxy, methyl, methoxy, or hydroxy.

In still yet another embodiment, the invention provides compounds of formula III-5, i.e., compound of formula III-4, where the heteroaryl portion of the heteroaryl or heteroaryl $C_1$-$C_6$ alkyl group is an unsubstituted thienyl (such as a 2-thienyl).

In still yet another embodiment, the invention provides compounds of formula III-6, i.e., compound of formula III-4, where the heteroaryl portion of the heteroaryl or heteroaryl $C_1$-$C_6$ alkyl group is thienyl substituted with one halogen (such as Cl). In one aspect, the mono halogenated thienyl is a 3-chlorothien-2-yl.

In still yet another embodiment, the invention provides compounds of formula III-7, i.e., compound of formula III-4, where the heteroaryl portion of the heteroaryl or heteroaryl $C_1$-$C_6$ alkyl group is thienyl substituted with two independently selected halogens. In one aspect, both halogens are the same and they are Cl.

In still yet another embodiment, the invention provides compounds of formula III-8, i.e., compound of formula III-4, where the heteroaryl portion of the heteroaryl or heteroaryl $C_1$-$C_6$ alkyl group is thienyl substituted with —$SO_2$—($C_1$-$C_4$ alkyl). In one aspect, the heteroaryl portion is 3-chloro-4-(methylsulfonyl)thien-2-yl.

In yet still another embodiment, the invention provides compounds of formula III-9, i.e., compound of formula III-3, where the heteroaryl portion of the heteroaryl or heteroaryl $C_1$-$C_6$ alkyl group is thiadiazolyl optionally substituted with $C_1$-$C_4$ alkyl (such as methyl). In one aspect, the heteroaryl portion is 4-methyl-thiadiazol-5-yl.

In still another embodiment, the invention provides compounds of formula III-10, i.e., compound of formula III-3, where the heteroaryl portion of the heteroaryl or heteroaryl $C_1$-$C_6$ alkyl group is pyrazolyl optionally substituted with 1 or 2 groups, where each group is independently $C_1$-$C_4$ alkyl (such as methyl) or halogen (such as Cl). In one aspect, the heteroaryl portion is 1-methyl-5-chloropyrazolyl.

In another embodiment, the invention provides compounds of formula III-11, i.e., compound of formula III-3, where the heteroaryl portion of the heteroaryl or heteroaryl $C_1$-$C_6$ alkyl group is isoxazolyl optionally substituted with 1 or 2 groups, where each group is independently $C_1$-$C_4$ alkyl (such as methyl), phenyl optionally substituted with 1, 2, or 3 groups that are independently $C_1$-$C_4$ alkyl, $C_1$-$C_4$ alkoxy, or halogen (such as F or Cl). In one aspect, the isoxazolyl portion of the heteroaryl or heteroaryl $C_1$-$C_6$ alkyl group is 5-methylisoxazol-3-yl. In another aspect, the isoxazolyl portion is 3,5-dimethylisoxazol-3-yl. In yet another aspect, the isoxazolyl portion is unsubstituted. In still yet another aspect, the isoxazolyl portion is substituted with one methyl and one phenyl (where the phenyl is unsubstituted or substituted with at least one halogen or methyl).

In another embodiment, the invention provides compounds of formula III-12, i.e., compound of formula III-3, where the heteroaryl portion of the heteroaryl or heteroaryl $C_1$-$C_6$ alkyl group is furanyl optionally substituted with 1 or 2 groups, where each group is independently $C_1$-$C_4$ alkyl, or —$CO_2$($C_1$-$C_4$ alkyl). In one aspect, the furanyl portion is substituted with two $C_1$-$C_4$ alkyl groups. In another aspect, the furanyl portion is 2,5-dimethyl-furan-3-yl.

In still another embodiment, the invention provides compounds of formula III-13, i.e., compound of formula III-3, where the heteroaryl portion of the heteroaryl or heteroaryl $C_1$-$C_6$ alkyl group is benzothienyl, which is optionally substituted with 1, 2, or 3 groups, where each group is independently $C_1$-$C_4$ alkyl, $C_1$-$C_4$ alkoxy, or halogen. In one aspect, the benzothienyl ring is substituted on the thienyl ring with a chloro. In another aspect, the benzothienyl group is unsubstituted.

In still another embodiment, the invention provides compounds of formula III-14, i.e., compound of formula III-3, where the heteroaryl portion of the heteroaryl or heteroaryl $C_1$-$C_6$ alkyl group is pyridyl optionally substituted with one or two groups, where each group is halogen, —S—($C_1$-$C_4$ alkyl), $C_1$-$C_4$ alkyl, or $C_1$-$C_4$ alkoxy. In one aspect, the pyridyl is unsubstituted. In another aspect, the pyridyl is 2-chloropyrid-3-yl. In still another aspect, the pyridyl is 2-methylthiopyrid-3-yl.

In still another embodiment, the invention provides compounds of formula III-15, i.e., compound of formula III-3, where the heteroaryl portion of the heteroaryl or heteroaryl $C_1$-$C_6$ alkyl group is benzofuranyl optionally substituted with 1 or 2 groups that are independently $C_1$-$C_4$ alkyl, $C_1$-$C_4$ alkoxy, or halogen. In another aspect, the benzofuranyl ring is substituted on the furanyl ring with a methyl group.

In yet still yet another embodiment, the invention provides compounds of formula III-16, i.e., compounds according to any one of formulas III-3, III-4, III-5, III-6, III-7, III-8, III-9, III-10, III-11, III-12, III-13, III-14, or III-15, where Q is tetrazolyl.

In yet still another embodiment, the invention provides compounds of formula III-17, i.e., compounds according to any one of formulas III-3, III-4, III-5, III-6, III-7, III-8, III-9, III-10, III-11, III-12, III-13, III-14, or III-15, where Q is carboxyl.

In still another embodiment, the invention provides compounds of formula III-18, i.e., compounds according to any one of formulas III-3, III-4, III-5, III-6, III-7, III-8, III-9, III-10, III-11, III-12, III-13, III-14, III-15, III-16, or III-17, where $R_1$ is chloro, $R_2$, $R_3$, and $R_5$ are H.

In still yet another embodiment, the invention provides compounds of formula III-19, i.e., compounds according to any one of formulas III-3, III-4, III-5, III-6, III-7, III-8, III-9, III-10, III-11, III-12, III-13, III-14, III-15, III-16, III-17, or III-18, where the alkyl portion of the heteroaryl $C_1$-$C_6$ alkyl group is a $C_1$-$C_4$ alkyl group. In another aspect, the alkyl portion of the heteroaryl $C_1$-$C_6$ alkyl group is a $C_1$-$C_2$ alkyl group. In still another aspect, the alkyl portion of the heteroaryl $C_1$-$C_6$ alkyl group is a $C_2$-$C_4$ alkyl group.

In yet another embodiment, the invention provides compounds of formula III-20, i.e., compounds according to any one of formulas III-3, III-4, III-5, III-6, III-7, III-8, III-9, III-10, III-11, III-12, III-13, III-14, III-15, III-16, or III-17, where $R_1$ is chloro.

In another embodiment, the invention provides compounds of formula IV, i.e., compound of formula I-1, where $R_4$ is heterocycloalkyl or heterocycloalkyl $C_1$-$C_6$ alkyl, each of which is optionally substituted with one or more groups, where each group is independently $C_1$-$C_6$ alkyl, $C_1$-$C_6$ alkoxy, halogen, $C_1$-$C_6$ haloalkyl, $C_1$-$C_6$ haloalkoxy, $C_1$-$C_6$ alkoxy $C_1$-$C_6$ alkyl, $NR_6R_7$, $C_2$-$C_6$ alkanoyl, aryl, or $C_1$-$C_6$ alkyl substituted with $C_1$-$C_6$ alkoxycarbonyl, where the aryl is selected from phenyl and naphthyl, and where the aryl is optionally substituted with one or more groups, where each group is independently halogen, $C_1$-$C_6$ haloalkyl, $C_1$-$C_6$ haloalkoxy, $C_1$-$C_6$ alkyl (such as methyl), $C_1$-$C_6$ alkoxy (such as methoxy), hydroxy, $NR_6R_7$, 4-methylpiperazin-1-yl, $CF_3$, $OCF_3$, $C_2$-$C_6$ alkanoyl, or $C_1$-$C_6$ alkyl substituted with $C_1$-$C_6$ alkoxycarbonyl.

In still another embodiment, the invention provides compounds of formula IV-1, i.e., compound of formula IV, where Y is $CR_5$; Z is $CR_2$; and $R_2$ and $R_5$ are independently H or halogen.

In yet another embodiment, the invention provides compounds of formula IV-2, i.e., compound of formula IV-1, where $R_1$, $R_2$, and $R_3$ are independently H, chloro, bromo, methyl, $NR_6R_7$, or methoxy; and where $R_6$ and $R_7$ at each occurrence are independently H, $C_1$-$C_4$ alkyl, $C_2$-$C_4$ alkanoyl, or phenyl $C_1$-$C_4$ alkyl.

In still yet another embodiment, the invention provides compounds of formula IV-3, i.e., compound of formula IV-2, where $R_4$ is heterocycloalkyl or heterocycloalkyl $C_1$-$C_6$ alkyl, where the heterocycloalkyl group is 3-oxo-2-oxabicyclo[2.2.1]heptanyl, piperidinyl, or tetrahydrofuranyl, each of which is optionally substituted with one or more groups, where each group is independently $C_1$-$C_6$ alkyl, $C_1$-$C_6$ alkoxy, halogen, $C_1$-$C_4$ haloalkyl, $C_1$-$C_4$ haloalkoxy, $C_1$-$C_6$ alkoxy $C_1$-$C_6$ alkyl, $NR_6R_7$, $C_2$-$C_6$ alkanoyl, aryl, or $C_1$-$C_6$ alkyl substituted with $C_1$-$C_6$ alkoxycarbonyl, where the aryl is selected from phenyl and naphthyl, and where the aryl is optionally substituted with one or more groups, where each group is independently halogen, $C_1$-$C_6$ alkyl, $C_1$-$C_6$ alkoxy, or hydroxy.

In yet another embodiment, the invention provides compounds of formula IV-4, i.e., compound of formula IV-3, where $R_4$ is heterocycloalkyl or heterocycloalkyl $C_1$-$C_6$ alkyl, where the heterocycloalkyl group is 3-oxo-2-oxabicyclo[2.2.1]heptane substituted with one or more methyl groups. In one aspect, the heterocycloalkyl portion is 4,7,7-trimethyl-3-oxo-2-oxabicyclo[2.2.1]heptan-1-yl.

In still yet another embodiment, the invention provides compounds of formula IV-5, i.e., compound of formula IV-3, where $R_4$ is heterocycloalkyl or heterocycloalkyl $C_1$-$C_6$ alkyl, where the heterocycloalkyl group is piperidinyl substituted with $C_2$-$C_4$ alkanoyl (such as acetyl or propionyl). In one aspect, the piperidinyl group is acylated on the nitrogen with an acetyl group.

In still another embodiment, the invention provides compounds of formula IV-6, i.e., compound of formula IV-3, where $R_4$ is heterocycloalkyl or heterocycloalkyl $C_1$-$C_6$ alkyl, where the heterocycloalkyl group is tetrahydrofuranyl.

In still another embodiment, the invention provides compounds of formula IV-7, i.e., compounds according to any one of formulas IV-3, IV-4, IV-5, or IV-6 where Q is tetrazolyl.

In still another embodiment, the invention provides compounds of formula IV-8, i.e., compounds according to any one of formulas IV-3, IV-4, IV-5, or IV-6 where Q is carboxyl.

In yet still yet another embodiment, the invention provides compounds of formula IV-9, i.e., compounds according to any one of formulas IV-3, IV-4, IV-5, IV-6, IV-7, or IV-8, where $R_1$ is chloro.

In yet still yet another embodiment, the invention provides compounds of formula IV-10, i.e., compounds according to any one of formulas IV-3, IV-4, IV-5, IV-6, IV-7, IV-8, or IV-9 where $R_2$, $R_3$, and $R_5$ are H.

In another embodiment, the invention provides compounds of formula V, i.e., compounds of formula I-1 where $R_4$ is cycloalkyl, or cycloalkyl $C_1$-$C_6$ alkyl, each of which is optionally substituted with one or more groups, where each group is independently $C_1$-$C_6$ alkyl, $C_1$-$C_6$ alkoxy, halogen, $C_1$-$C_6$ alkoxy $C_1$-$C_6$ alkyl, $NR_6R_7$, $C_2$-$C_6$ alkanoyl, aryl, or $C_1$-$C_6$ alkyl substituted with $C_1$-$C_6$ alkoxycarbonyl, where the aryl is selected from phenyl and naphthyl, where the aryl is optionally substituted with one or more groups, where each group is independently halogen, $C_1$-$C_6$ haloalkyl, $C_1$-$C_6$ haloalkoxy, $C_1$-$C_6$ alkyl (such as methyl), $C_1$-$C_6$ alkoxy (such as methoxy), hydroxy, $NR_6R_7$, 4-methylpiperazin-1-yl, $CF_3$, $OCF_3$, $C_2$-$C_6$ alkanoyl, or $C_1$-$C_6$ alkyl substituted with $C_1$-$C_6$ alkoxycarbonyl.

In yet another embodiment, the invention provides compounds of formula V-1, i.e., compounds of formula V where Y is $CR_5$; Z is $CR_2$; and $R_2$ and $R_5$ are independently H or halogen.

In still another embodiment, the invention provides compounds of formula V-2, i.e., compounds of formula V-1 where $R_1$, $R_2$, and $R_3$ are independently H, chloro, bromo, fluoro, iodo, methyl, $NR_6R_7$, or methoxy; and where $R_6$ and $R_7$ at each occurrence are independently H, $C_1$-$C_4$ alkyl, $C_2$-$C_4$ alkanoyl, or phenyl $C_1$-$C_4$ alkyl.

In yet still another embodiment, the invention provides compounds of formula V-3, i.e., compounds of formula V-2 where $R_4$ is cyclohexyl, tricyclo[3.3.1.1~3,7~]decanyl (also known as adamantyl), cyclopentyl, or cyclopentylmethyl, each of which is optionally substituted with one or more groups, where each group is independently $C_1$-$C_4$ alkyl, $C_1$-$C_4$ alkoxy, halogen, $C_1$-$C_4$ alkoxy $C_1$-$C_4$ alkyl, or phenyl. In one aspect, $R_4$ is unsubstituted cyclohexyl. In another aspect, $R_4$ is unsubstituted cyclopentyl. In still another aspect, $R_4$ is unsubstituted cyclobutyl. In yet still another aspect, $R_4$ is unsubstituted cyclopropyl. In still another aspect, $R_4$ is unsubstituted cyclopentylmethyl. In yet another aspect, $R_4$ is adamantyl.

In another embodiment, the invention provides compounds of formula V-4, i.e., compounds according to any one of formulas V-1, V-2, or V-3 where Q is tetrazolyl.

In another embodiment, the invention provides compounds of formula V-5, i.e., compounds according to any one of formulas V-1, V-2, or V-3 where Q is carboxyl.

In yet still yet another embodiment, the invention provides compounds of formula IV-6, i.e., compounds according to any one of formulas V-1, V-2, V-3, V-4, or V-5, where $R_1$ is chloro.

In yet still yet another embodiment, the invention provides compounds of formula IV-7, i.e., compounds according to any one of formulas V-1, V-2, V-3, V-4, V-5, or V-6, where $R_2$, $R_3$, and $R_5$ are H.

In another embodiment, the invention provides compounds of formula I-8, i.e., compounds of formula I-2 where, Y is N; and Z is N.

In another aspect, the invention provides a compound of formula I, or a pharmaceutically acceptable salt thereof, and at least one pharmaceutically acceptable carrier, excipient or solvent.

The following compounds are excluded from the scope of formula I for the purposes of compounds and compositions:
(2,6-Dichloro-benzoylamino)-(3-trifluoromethyl-phenyl)-acetic acid;
(2,6-Dichloro-benzoylamino)-(4-fluoro-phenyl)-acetic acid;
(2-Bromo-benzoylamino)-(4-fluoro-phenyl)-acetic acid;
(2-Bromo-benzoylamino)-(3-trifluoromethyl-phenyl)-acetic acid;
(2-Chloro-benzoylamino)-(4-fluoro-phenyl)-acetic acid;
(2-Chloro-benzoylamino)-(3-trifluoromethyl-phenyl)-acetic acid;
(2-Fluoro-benzoylamino)-(4-fluoro-phenyl)-acetic acid;
(2-Fluoro-benzoylamino)-(3-trifluoromethyl-phenyl)-acetic acid;
1-(2-Bromo-benzoyl)-pyrrolidine-2-carboxylic acid;
1-(2-Fluoro-benzoyl)-pyrrolidine-2-carboxylic acid;
1-(2,6-Dichloro-benzoyl)-pyrrolidine-2-carboxylic acid;
1-(2-Chloro-benzoyl)-pyrrolidine-2-carboxylic acid;
2-(2,6-Dichloro-benzoylamino)-cyclohexane carboxylic acid;
2-(2-Bromo-benzoylamino)-cyclohexane carboxylic acid;
2-(2-Chloro-benzoylamino)-cyclohexane carboxylic acid;
2-(2-Fluoro-benzoylamino)-cyclohexane carboxylic acid;
2-(4-Amino-benzoylamino)-benzoic acid;
2-(4-Chloro-benzoylamino)-3,5-dibromo-benzoic acid;
2-(4-Nitro-benzoylamino)-benzoic acid;
2-[2-(2-Chloro-phenyl)-acetylamino]-nicotinic acid;
2-[2-(3-Chloro-phenyl)-acetylamino]-nicotinic acid;
2-[2-(4-Chloro-phenyl)-acetylamino]-nicotinic acid;
2-({[4-(Acetylamino)phenyl]carbonyl}amino)-4-chlorobenzoic acid;
2-(3,4-Dichloro-benzoylamino)-nicotinic acid;
2-(3-Chloro-benzoylamino)-nicotinic acid;
2-(4-Bromo-benzoylamino)-benzoic acid;
2-Bromo-N-[5-chloro-2-(1H-tetrazol-5-yl)-phenyl]-benzamide;
2-Chloro-2-[2-(2-chloro-phenyl)-acetylamino]-benzoic acid;
2-Chloro-N-(2,3-difluoro-phenyl)-benzamide;
2-Chloro-N-[5-chloro-2-(1H-tetrazol-5-yl)phenyl]benzamide,
3-(2-Bromo-benzoylamino)-naphthalene-2-carboxylic acid;
3-(2-Chloro-benzoylamino)-naphthalene-2-carboxylic acid;
3,5-Dibromo-2-(2-chloro-benzoylamino)-benzoic acid;
3,5-Dibromo-2-(3-chloro-benzoylamino)-benzoic acid;
3,5-Dibromo-2-[2-(2,4-dichloro-phenyl)-acetylamino]-benzoic acid;
3,5-Dibromo-2-[2-(2-chloro-phenyl)-acetylamino]-benzoic acid;
3,5-Dibromo-2-[2-(3-chloro-phenyl)-acetylamino]-benzoic acid;
3,5-Dibromo-2-[2-(4-chloro-phenyl)-acetylamino]-benzoic acid;
3,5-Dibromo-2-(3,4-dichloro-benzoylamino)-benzoic acid;
3,5-Dibromo-2-[(thiophene-2-carbonyl)-amino]-benzoic acid;
3,5-Dibromo-2-[2-(5-chloro-1H-indole-2-carbonyl)-amino]-benzoic acid;
3,5-Dibromo-6-[(1H-indole-2-carbonyl)-amino]-benzoic acid;
3,6-Dibromo-2-(2,4-dichloro-benzoylamino)-benzoic acid;
3,4-Difluoro-2-[(2-fluoro-4-iodophenyl)amino]benzoic acid;
3-Bromo-6-(3-chloro-benzoylamino)-benzoic acid;
3-Bromo-6-(4-chloro-benzoylamino)-benzoic acid;
3-Bromo-6-(2,4-dichloro-benzoylamino)-benzoic acid;
3-Bromo-6-(2-chloro-benzoylamino)-benzoic acid;
3-Chloro-N-(2,3-difluoro-phenyl)-benzamide;
4,5-Bis(methyloxy)-2-[(2-thienylcarbonyl)amino]benzoic acid;
4-Bromo-2-[(thiophene-2-carbonyl)-amino]-benzoic acid;
4-Chloro-2-(2-bromo-benzoylamino)-benzoic acid;
4-Chloro-2-(2-chloro-benzoylamino)-benzoic acid;
4-Chloro-2-(3,4-dichloro-benzoylamino)-benzoic acid;
4-Chloro-2-(3-chloro-benzoylamino)-benzoic acid;
4-Chloro-2-(4-chloro-benzoylamino)-benzoic acid;
4-Chloro-2-[(1H-indole-3-carbonyl)-amino]-benzoic acid;
4-Chloro-2-[(5-chloro-1H-indole-2-carbonyl)-amino]-benzoic acid;
4-Chloro-2-[2-(3-chloro-phenyl)-acetylamino]-benzoic acid;
4-Chloro-2-({[2-(methyloxy)phenyl]carbonyl}amino)benzoic acid;
4-Chloro-2-({[4-(methyloxy)phenyl]carbonyl}amino)benzoic acid;
4-Chloro-2-(2,4-dichloro-benzoylamino)-benzoic acid;
4-Chloro-2-[(1H-indole-2-carbonyl)-amino]-benzoic acid;
4-Chloro-2-[(2,2-dimethylpropanoyl)amino]benzoic acid;
4-Chloro-2-[(2-thienylcarbonyl)amino]benzoic acid;
4-Chloro-2-[(3-phenylpropanoyl)amino]benzoic acid;

4-Chloro-2-[(cyclohexylcarbonyl)amino]benzoic acid;
4-Chloro-2-[(naphthalen-1-ylcarbonyl)amino]benzoic acid;
4-Chloro-2-[(naphthalen-2-ylcarbonyl)amino]benzoic acid;
4-Chloro-2-[(phenylacetyl)amino]benzoic acid;
4-Chloro-2-[(phenylcarbonyl)amino]benzoic acid;
4-Chloro-2-[(tetrahydrofuran-2-ylcarbonyl)amino]benzoic acid;
4-Chloro-2-[(thiophene-2-carbonyl)-amino]-benzoic acid;
4-Chloro-2-[2-(4-chloro-phenyl)-acetylamino]-benzoic acid;
4-Chloro-2-{[(2-chlorophenyl)carbonyl]amino}benzoic acid;
4-Chloro-2-{[(5-chloro-2-thienyl)carbonyl]amino}benzoic acid;
4-Chloro-3-(3-chloro-benzoylamino)-benzoic acid;
4-Chloro-3-(4-chloro-benzoylamino)-benzoic acid;
4-Chloro-N-(2,3-difluoro-phenyl)-benzamide;
5-Bromo-(3,4-dichloro-benzoylamino)-benzoic acid;
5-Bromo-2-(2,3-difluoro-benzoylamino)-benzoic acid;
5-Bromo-2-(2,4-difluoro-benzoylamino)-benzoic acid;
5-Bromo-2-(2,5-difluoro-benzoylamino)-benzoic acid;
5-Bromo-2-(2,6-dichloro-benzoylamino)-benzoic acid;
5-Bromo-2-(2,6-difluoro-benzoylamino)-benzoic acid;
5-Bromo-2-(2,6-dimethoxy-benzoylamino)-benzoic acid;
5-Bromo-2-(2-bromo-benzoylamino)-benzoic acid;
5-Bromo-2-(2-fluoro-4-trifluoromethyl-benzoylamino)-benzoic acid;
5-Bromo-2-(2-fluoro-benzoylamino)-benzoic acid;
5-Bromo-2-(2-iodo-benzoylamino)-benzoic acid;
5-Bromo-2-(2-methyl-benzoylamino)-benzoic acid;
5-Bromo-2-[2-(2,4-dichloro-phenyl)-acetylamino]-benzoic acid;
5-Bromo-2-[2-(2-chloro-phenyl)-acetylamino]-benzoic acid;
5-Bromo-2-[2-(3-chloro-phenyl)-acetylamino]-benzoic acid;
5-Bromo-2-[2-(4-chloro-phenyl)-acetylamino]-benzoic acid;
5-Bromo-2-(2-trifluoromethyl-benzoylamino)-benzoic acid;
5-Bromo-2-(4-ethoxy-benzoylamino)-benzoic acid;
5-Bromo-2-[(1H-indole-2-carbonyl)-amino]-benzoic acid;
5-Bromo-2-[(1H-indole-3-carbonyl)-amino]-benzoic acid;
5-Bromo-2-[(2-thienylcarbonyl)amino]benzoic acid;
5-Bromo-2-[(5-chloro-1H-indole-2-carbonyl)-amino]-benzoic acid;
5-Bromo-2-[(naphthalene-1-carbonyl)-amino]-benzoic acid;
5-Bromo-2-[2-(2,4-dichloro-phenoxy)-acetylamino]-benzoic acid;
5-Chloro-2-(2,3-difluoro-benzoylamino)-benzoic acid;
5-Chloro-2-(2,5-difluoro-benzoylamino)-benzoic acid;
5-Chloro-2-(2-bromo-benzoylamino)-benzoic acid;
5-Chloro-2-(2-fluoro-4-trifluoromethyl-benzoylamino)-benzoic acid;
5-Chloro-2-(2-fluoro-benzoylamino)-benzoic acid;
5-Chloro-2-(2-iodo-benzoylamino)-benzoic acid;
5-Chloro-2-(2,4-dichloro-benzoylamino)benzoic acid;
5-Chloro-2-(2,4-difluoro-benzoylamino)-benzoic acid;
5-Chloro-2-(2,6-dichloro-benzoylamino)-benzoic acid;
5-Chloro-2-(2,6-dimethoxy-benzoylamino)-benzoic acid;
5-Chloro-2-(2-trifluoromethyl-benzoylamino)-benzoic acid;
5-Chloro-2-(4-ethoxy-benzoylamino)-benzoic acid;
5-Chloro-2-[(2-thienylcarbonyl)amino]benzoic acid;
5-Chloro-2-[(naphthalene-1-carbonyl)-amino]-benzoic acid;
5-Chloro-2-[2-(2,4-dichloro-phenyl)-acetylamino]-benzoic acid;
5-Iodo-2-(2,4-difluoro-benzoylamino)-benzoic acid;
5-Iodo-2-(2,6-dimethoxy-benzoylamino)-benzoic acid;
5-Iodo-2-(2-bromo-benzoylamino)-benzoic acid;
5-Iodo-2-(2-fluoro-4-trifluoromethyl-benzoylamino)-benzoic acid;
5-Iodo-2-(4-ethoxy-benzoylamino)-benzoic acid;
5-Iodo-2-[(naphthalene-1-carbonyl)-amino]-benzoic acid;
5-Iodo-2-(2,3-difluoro-benzoylamino)-benzoic acid;
5-Iodo-2-(2,5-difluoro-benzoylamino)-benzoic acid;
5-Iodo-2-(2,6-difluoro-benzoylamino)-benzoic acid;
5-Iodo-2-(2-chloro-benzoylamino)-benzoic acid;
5-Iodo-2-(2-fluoro-benzoylamino)-benzoic acid;
5-Iodo-2-(2-iodo-benzoylamino)-benzoic acid;
5-Iodo-2-(2-methyl-benzoylamino)-benzoic acid;
5-Iodo-2-(2-trifluoromethyl-benzoylamino)-benzoic acid;
5-Iodo-2-(thiophene-2-yl)-benzoic acid;
5-Iodo-3-(2,4-dichloro-benzoylamino)-benzoic acid;
5-Methyl-2-(2,6-dichloro-benzoylamino)-benzoic acid;
5-Methyl-2-(2,6-dimethoxy-benzoylamino)-benzoic acid;
5-Methyl-2-(2-fluoro-benzoylamino)-benzoic acid;
N-[5-chloro-2-(1H-tetrazol-5-yl)phenyl]thiophene-2-carboxamide;
Thiophene-2-carboxylic acid (2,3-difluoro-phenyl)amide; or
Thiophene-2-carboxylic acid [5-chloro-2-(1H-tyetrazol5-yl)-phenyl]-amide;

but these compounds are encompassed by formula I with respect to methods of treating diseases, conditions, or malignancies responsive to inhibition of PIM-1 and/or PIM-3 and methods of preparing medicaments useful in the treatment of diseases, conditions, or malignancies responsive to inhibition of PIM-1 and/or PIM-3.

In still another aspect, the invention provides a method of inhibiting the in vivo activity of PIM-1 and/or PIM-3, the method comprising administering to a subject a therapeutically effective amount of a compound or salt of formula I, or a pharmaceutical composition thereof.

In yet another aspect, the invention provides a method of treating diseases or disorders associated with uncontrolled, abnormal, and/or unwanted cellular activities effected directly or indirectly by PIM-1 and/or PIM-3, the method comprising administering to a mammal in need of such treatment a therapeutically effective amount of a compound or salt of formula I, or a pharmaceutical composition thereof.

In another aspect, the invention provides a method of inhibiting proliferative activity in a cell, the method comprising administering to a cell or a plurality of cells an effective amount of a compound or salt of formula I, or a pharmaceutical composition thereof.

In still another aspect, the invention provides a method of treating cancer, comprising administering a therapeutically effective amount of a compound of formula I, a pharmaceutically acceptable salt of formula I, a pharmaceutical composition comprising a compound or salt of formula I, to a patient in need of such treatment.

A further aspect of the invention is a method of treating malignancies such as ovarian cancer, cervical cancer, breast cancer, colorectal cancer, and glioblastomas, among others, in a patient in need of such treatment, by administering a compound or salt of formula I, or a pharmaceutical composition thereof.

DEFINITIONS

As used in the present specification, the following words and phrases are generally intended to have the meanings as set forth below, except to the extent that the context in which they are used indicates otherwise or they are expressly defined to mean something different.

If a group "R" is depicted as "floating" on a ring system, as for example in the formula:

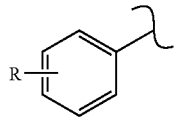

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

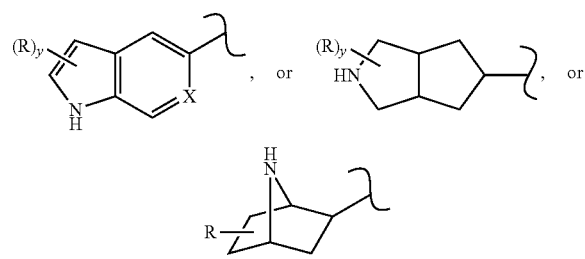

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals ═CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

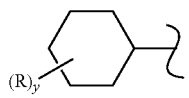

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

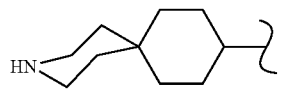

"Alkyl" is intended to include both linear and branched hydrocarbon structures and combinations thereof, inclusively. For example, "$C_8$ alkyl" may refer to an n-octyl, iso-octyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. A "$C_0$" alkyl (as in "$C_0$-$C_6$-alkyl") is a covalent bond. Exemplary alkyl groups are those of $C_{20}$ or below. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl; and for example, "propyl" or "$C_3$ alkyl" each include n-propyl, and isopropyl.

"Alkoxy" refers to the group —O-alkyl, where alkyl is as previously defined, and where the alkoxy group is attached to the parent structure through an oxygen atom. Examples include methoxy, ethoxy, propoxy, isopropoxy, and the like. Lower-alkoxy refers to groups containing one to six carbons.

"Amino" refers to the group —$NH_2$.

The term "aryl" refers to an aromatic hydrocarbon ring system containing at least one aromatic hydrocarbon ring. Preferred aryl rings have 6 members. Preferred aryl ring systems have 10-14 members. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene, anthracenyl, indanyl, and biphenyl. Preferred examples of aryl groups include phenyl, naphthyl, and anthracenyl. More preferred aryl groups are phenyl and naphthyl. Most preferred is phenyl.

The term "cycloalkyl" refers to a monocyclic and polycyclic saturated or partially saturated hydrocarbon ring or ring system. Preferred monocyclic rings have $C_3$-$C_8$ ring members. Examples of monocyclic cycloalkyl groups include cyclopropyl, cyclobutyl, cyclopentyl, cyclohexyl, cycloheptyl and cyclooctyl. Examples of polycyclic cycloalkyl groups include bicyclo[2.2.1]heptyl, and adamantyl (tricyclo [3.3.1.1~3,7~]decanyl).

"Halogen" or "halo" refers to fluorine, chlorine, bromine or iodine.

"Haloalkoxy" refers generically to alkoxy groups that are substituted with one or more halogens, respectively. When the alkoxy group is substituted with a plurality of halogens, the halogens may, but need not necessarily be the same halogen.

"Haloalkyl" refers generically to alkyl groups that are substituted with one or more halogens, respectively. Thus, "dihaloalkyl," etc. refer to an alkyl substituted with a plurality of halogens, but not necessarily a plurality of the same halogen.

The term "heterocycloalkyl" refers to a 3-8 membered ring or 7-12 membered ring system (which may be, fused or spiro), where at least one ring is saturated or partially saturated and contains at least one heteroatom selected from nitrogen, oxygen, and sulfur, wherein the heteroatom is in said saturated or partially saturated ring. Heterocycloalkyl rings may be fused to one or more unsaturated, saturated, or partially saturated hydrocarbon rings (such as phenyl, cyclohexyl or cyclopentene). Preferred heterocycloalkyl rings have 5 or 6 members. Preferred heterocycloalkyl ring systems comprise two fused 5 membered rings (which ring system has a total of 8 ring members), two fused 6 membered rings (which ring system has a total of 10 ring members), and one 5 membered ring fused to a 6 membered ring (which ring system has a total of 9 ring members). The heterocycloalkyl ring is optionally fused to or otherwise attached to other heterocycloalkyl rings and/or non-aromatic hydrocarbon rings and/or phenyl rings. Preferred heterocycloalkyl groups have from 3 to 7 members. Examples of heterocycloalkyl groups include, for example, 1,2,3,4-tetrahydroisoquinolinyl, 3-oxo-2-oxabicyclo[2.2.1]heptyl, piperazinyl, morpholinyl, piperidinyl, tetrahydrofuranyl, pyrrolidinyl, pyridinonyl, isoindolyl, and pyrazolidinyl. Preferred heterocycloalkyl groups include piperidinyl, piperazinyl, morpholinyl, pyrrolidinyl, pyridinonyl, isoindolyl, dihydropyrrolidinyl, 3-oxo-2-oxabicyclo[2.2.1]heptyl, tetrahydrofuranyl, and pyrrolidinonyl.

The term "heteroaryl" refers to an aromatic ring or ring system (where two rings are fused) containing at least one heteroatom selected from nitrogen, oxygen, and sulfur. Preferred heteroaryl rings have 5 or 6 members. The heteroaryl ring may be fused or otherwise attached to one or more heteroaryl rings, aromatic or non-aromatic hydrocarbon rings or heterocycloalkyl rings. Examples of heteroaryl groups include, for example, furanyl, thienyl, 5,6,7,8-tetrahydroisoquinolinyl, benzothienyl, pyridyl, quinolyl, pyrazolyl, pyrimidyl, imidazolyl, benzimidazolyl, benzofuranyl, dibenzofuranyl, thiazolyl, benzothiazolyl, isoxazolyl, oxadiazolyl, isothiazolyl, benzisothiazolyl, triazolyl, thiadiazolyl, pyrrolyl, indolyl, indazolyl, pyrazolyl, and benzopyrazolyl. Preferred heteroaryl groups include thienyl, thiadiazolyl, oxazolyl, benzothienyl, isoxazolyl, benzofuranyl, pyridyl, pyrazolyl, or furanyl, indazolyl, and thiazolyl.

"Optional" or "optionally" means that the subsequently described event or circumstance may or may not occur, and that the description includes instances where said event or circumstance occurs and instances in which it does not. "Optionally substituted" refers to all subsequent modifiers in a term. So, for example, in the term "optionally substituted arylC$_{1-8}$ alkyl," optional substitution may occur on both the "C$_{1-8}$ alkyl" portion and the "aryl" portion of the molecule may or may not be substituted. A list of exemplary optional substitutions is presented below in the definition of "substituted." It will also be understood that the number of substituents will not exceed the number of available valences. Compounds of the invention are named using either 1) the systematic application of the nomenclature rules agreed upon by the International Union of Pure and Applied Chemistry (IUPAC), International Union of Biochemistry and Molecular Biology (IUBMB), and the Chemical Abstracts Service (CAS); 2) ChemDraw, or the names are derived therefrom.

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent group, for example, —OCH$_2$—, then it is understood that either of the two partners may be bound to the particular group at one end, and the other partner is necessarily bound to the other end of the particular group, unless stated explicitly otherwise. Stated another way, divalent groups are not to be construed as limited to the depicted orientation, for example "—OCH$_2$—" is meant to mean not only "—OCH$_2$—" as drawn, but also "—CH$_2$O—."

In addition to the preferred embodiments recited hereinabove, also preferred are embodiments comprising combinations of preferred embodiments.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertol/Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

The term "pharmaceutically acceptable salts" encompasses both acid addition salts, base addition salts, solvates and hydrates thereof.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular PIM-1 and/or PIM-3-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Compositions suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example PIM-1 and/or PIM-3, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, PIM-1 and/or PIM-3 may be done in a number of ways. In one example, the candidate agent (the compound of the invention) is labeled, for example, with a fluorescent or radioactive moiety and binding determined directly. For example, thus may be done by attaching all or a portion of the PIM-1 and/or PIM-3 protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

The term "labeled" as used herein is meant to include both direct and indirect labeling with a compound that provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, PIM-1 and/or PIM-3 protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. The terms "candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to PIM-1 and/or PIM-3.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocycloalkyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to PIM-1 and/or PIM-3, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to PIM-1 and/or PIM-3 protein for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to PIM-1 and/or PIM-3 and thus is capable of binding to, and potentially modulating, the activity of the PIM-1 and/or PIM-3. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to PIM-1 and/or PIM-3 with a higher affinity. Thus, if the candidate agent is labeled, the presence of the label on the support, coupled with a lack of competitor binding, may indicate the candidate agent is capable of binding to PIM-1 and/or PIM-3.

It may be of value to identify the binding site of PIM-1 and/or PIM-3. This can be done in a variety of ways. In one embodiment, once PIM-1 and/or PIM-3 is identified as binding to the candidate agent, the PIM-1 and/or PIM-3 is fragmented or modified and the assays repeated to identify the necessary components for binding.

Modulation is tested by screening for candidate agents capable of modulating the activity of PIM-1 and/or PIM-3 comprising the steps of combining a candidate agent with PIM-1 and/or PIM-3, as above, and determining an alteration in the biological activity of the PIM-1 and/or PIM-3. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native PIM-1 and/or PIM-3, but cannot bind to modified PIM-1 and/or PIM-3.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components can be added in any order that provides for the requisite binding.

The disclosures in this application of all articles and references, including patents, are incorporated herein by reference.

Preparation of Compounds

Synthesis of Compounds:

The differing nature the various acidic functionalities, such as carboxylic acids and tetrazoles, mandates different synthetic routes for the preparation of the various forms of the compounds of the invention. Scheme 1 depicts the general synthetic route for the preparation of the carboxylic acid derivatives. Scheme 2 depicts the general synthetic route for the tetrazole derivatives. These schemes depict the general synthetic route for the compounds of the invention and are not expected to be limiting. Specific examples are described subsequently to these general synthetic descriptions. In the generalizations below, specific reaction conditions or details for example, added reagents, solvents, reaction temperatures and the like are not described. The general routes depicted in conjunction with the specific examples provided contain sufficient information to allow one of ordinary skill in the art to synthesize compounds of the invention.

Scheme 1

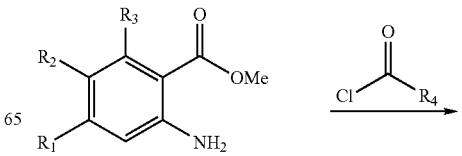

-continued

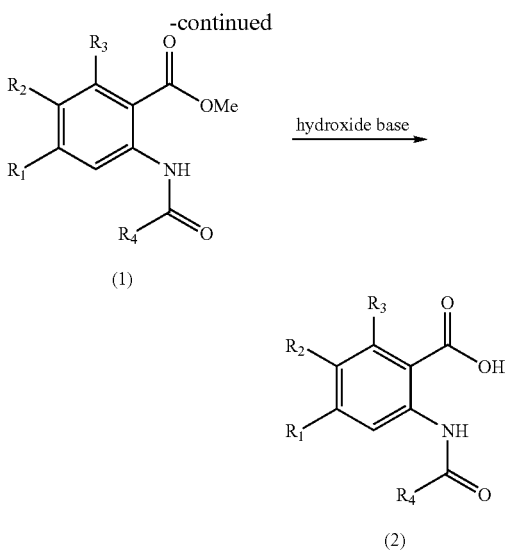

(1)

(2)

In Scheme 1, X is —C(O)— and Q is carboxyl.

In Scheme 1, the acidic group on the 2-amino-benzoic acid is masked as a methyl ester, although other masking groups are also useful. Acylation of the amine to form compound (1) can be performed with an acid chloride, although carboxylic acids and a suitable coupling reagent (or reagents) can also be used. Unmasking of the acid to form compound (2) is accomplished through hydrolysis of the ester or other suitable methods as are known in the art.

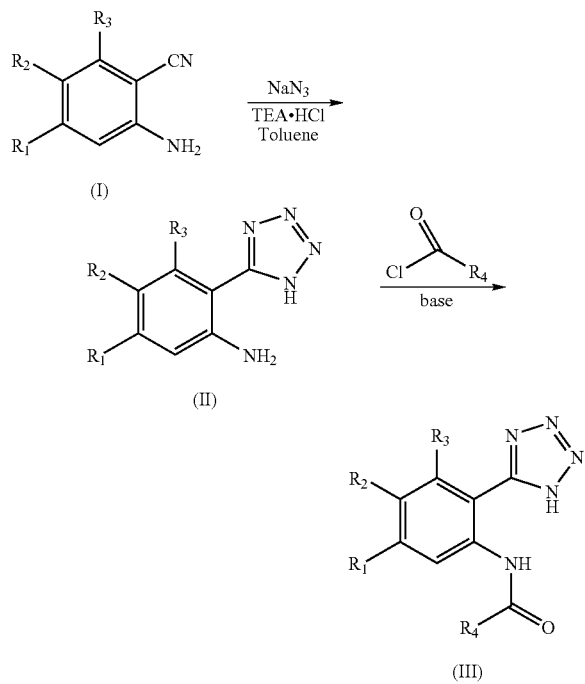

In Scheme 2, X is —C(O)— and Q is tetrazolyl.

In Scheme 2, a general synthetic route for the compounds of the invention is illustrated. 2-amino-benzonitriles (I) are converted into the corresponding tetrazoles through the addition of sodium azide to yield the 2-aminophenyl-1H-tetrazoles (II). The procedures used for conversion of nitrites to tetrazoles were based on the methods outlined in Koguro, Kiyoto; Oga, Toshikazu; Mitsui, Sunao; Orita, Ryozo. *Synthesis* 1998, 910-914. These compounds are then subsequently acylated with acid chlorides or acids and coupling reagent(s) to yield compounds (III). This acylation step can be adapted for rapid parallel synthesis of compounds for generating compound libraries of tetrazoles. In many cases the sequence of steps can be reversed with acylation preceding tetrazole formation.

EXAMPLES

The following examples serve to more fully describe the manner of using the above described invention, as well as to set forth the best modes contemplated for carrying out the invention. It is understood that these examples in no way serve to limit the true scope of this invention., but rather are presented for illustrative purposes. All references cited herein are incorporated by reference in their entirety. Generally, each example is set out below with a corresponding multi-step synthesis scheme. Following specific examples are lists of compounds that were made in a similar way.

Example 1

4-Chloro-2-{[(2,5-dimethylfuran-3-yl)carbonyl]amino}benzoic acid

In a 2 mL vial, methyl 2-amino-4-chlorobenzoate (7.4 mg, 40 μmol) was dissolved into a mixture of 655 μL DCE and 120 μL DMA, followed by addition of DIPEA (600 μmol, 15 eq.). 2,5-Dimethylfuran-3-carboxylic acid (16.8 mg, 120 μmol, 3 eq.) and $POCl_3$ (18.2 mg, 120 μmol, 3 eq.) were added. The reaction mixture was capped and stirred at room temperature overnight. Another 700 μL of DCE was added to the reaction mixture along with the following resin bound reagents: a resin bound diethylene triamine (PL-DETA, Polymer Labs, 297 μmol, 7.4 eq.) and a hydroxide ion exchange resin (PL-MP Hydroxide, Polymer Labs, 800 μmol, 20 eq.). The vial was recapped and shaken at room temperature overnight. The resin in the reaction mixture was filtered off, rinsed with 300 μL of MeOH and discarded. The combined filtrates were concentrated down in vacuo. The residue was re-dissolved into 1 mL of DMA and 280 μL of 1M aqueous NaOH. The solution was stirred at room temperature overnight. The desired product was isolated directly from this solution via reverse phase C18 preparative HPLC (water/acetonitrile w/0.1% formic acid, 30%-100% eluant gradient) to yield the final product (2.3 mg, 95% purity). MS (EI) for $C_{14}H_{12}ClNO_4$: 294 (M+H).

Example 2

5-Chloro-2-(1H-tetrazol-5-yl)aniline

5-Chloro-2-(1H-tetrazol-5-yl)aniline: 2-Amino-4-chlorobenzonitrile (1000 mg, 6.6 mmol), sodium azide (555 mg, 8.5 mmol) and triethylamine hydrochloride (1175 mg, 8.5 mmol) were taken up in 15 mL of toluene. The suspension was heated to 100° C. overnight. After cooling, the reaction mixture was washed 3 times with 5 mL portions of water. The combined aqueous fractions were acidified with concentrated hydrochloric acid. The desired 5-Chloro-2-(1H-tetrazol-5-yl)aniline precipitated from aqueous solution and was isolated by filtration (1090 mg, 85% yield). $^1$H NMR (500 MHz, DMSO-d$_6$) δ 7.73 (d, 1H), 6.97 (d, 1H), 6.74 (dd, 1H); MS (electrospray) m/z 196 (M+H).

Example 3

4-Chloro-2-[({4-[4-(methyloxy)phenyl]-2-thienyl}carbonyl)amino]benzoic acid

In a 2 mL vial, methyl 2-amino-4-chlorobenzoate (7.4 mg, 40 μmol) was dissolved into a mixture of 655 μL DCE and 120 μL DMA, followed by addition of DIPEA (600 μmol, 15 eq.). 4-(4-Methoxyphenyl)thiophene-2-carboxylic acid (13.7 mg, 120 μmol, 3 eq.) and POCl$_3$ (28.1 mg, 120 μmol, 3 eq.) were added. The reaction mixture was capped and stirred at room temperature overnight. Another 700 μL of DCE was added to the reaction mixture along with the following resin bound reagents: a resin bound diethylene triamine (PL-DETA, Polymer Labs, 297 μmol, 7.4 eq.) and a hydroxide ion exchange resin (PL-MP Hydroxide, Polymer Labs, 800 μmol, 20 eq.). The vial was recapped and shaken at room temperature overnight. The resin in the reaction mixture was filtered off, rinsed with 300 μL of MeOH and discarded. The combined filtrates were concentrated down in vacuo. The residue was re-dissolved into 1 mL of DMA and 280 μL of 1M aqueous NaOH. The solution was stirred at room temperature overnight. The desired product was isolated directly from this solution via reverse phase C18 preparative HPLC (water/acetonitrile w/0.1% formic acid, 30%-100% eluant gradient) to yield the final product (4.7 mg, 92% purity). MS (EI) for C$_{19}$H$_{14}$ClNO$_4$S: 388 (M+H).

Example 4

3-Chloro-N-(5-chloro-2-(1H-tetrazol-5-yl)phenyl)thiophene-2-carboxamide

The intermediate 5-chloro-2-(1H-tetrazol-5-yl)aniline (200 mg, 1.0 mmol) and diisopropylethylamine (310 uL, 1.7 mmol) were taken up in 5 mL of dichloromethane. To the solution was added 3-chlorothiophene-2-carboyl chloride (221 mg, 1.2 mmol). The solution was stirred for 4 hours, at which point starting material was no longer detected by LCMS analysis. Dichloromethane (10 ml) was then added to solution. This solution was extracted 3 times with an aqueous solution of 0.1 N NaOH. The aqueous extractions were combined and concentrated HCl was added to until pH=1. The resulting precipitate was filtered and washed with acetonitrile to yield final product (141.1 mg, 41%). $^1$H NMR (400 MHz, d6-DMSO): 11.89 (s, 1H), 8.60 (s, 1H), 8.26 (d, 1H), 8.05 (d, 1H), 7.45 (d, 1H), 7.30 (d, 1H). MS (EI) for C$_{12}$H$_7$Cl$_2$N$_5$OS: 340.2 (M+H).

Example 5

N-[5-Chloro-2-(1H-tetrazol-5-yl)phenyl]benzamide

The title compound was prepared essentially according to the method of Example 4, but using 5-chloro-2-(1H-tetrazol-5-yl)aniline (3.6 mmol) and benzoyl chloride to yield the desired product (647 mg, 60% yield). $^1$H NMR (400 MHz, DMSO-d6) δ 11.80 (s, 1H), 8.75 (d, 1H), 8.08-8.05 (m, 3H), 7.69-7.62 (m, 3H), 7.49 (dd, 1H); MS (EI) for C$_{14}$H$_{10}$ClN$_5$O: m/z 300 (M+H).

Example 6

N-[5-Chloro-2-(1H-tetrazol-5-yl)phenyl]-3-(methyloxy)benzamide

The title compound was prepared essentially according to the method of Example 4, but using 5-Chloro-2-(1H-tetrazol-5-yl)aniline (1.0 mmol) and 3-methoxybenzoyl chloride to afford the desired product (29.1 mg, 9%). $^1$H NMR (400 MHz, d6-DMSO): δ 10.81 (s, 1H), 8.75 (s, 1H), 8.06 (s, 1H), 7.60 (m, 3H), 7.25 (s, 1H), 3.89 (s, 3H). MS (EI) for C$_{15}$H$_{12}$ClN$_5$O$_2$: 329.7 (M+H).

Example 7

3-Chloro-N-[5-chloro-2-(1H-tetrazol-5-yl)phenyl]benzamide

The title compound was prepared essentially according to the method of Example 4, but using 5-Chloro-2-(1H-tetrazol-5-yl)aniline (1.0 mmol) and 3-chlorobenzoyl chloride. After precipitation, the product was further purified by reverse phase C18 preparative HPLC (water/acetonitrile w/0.1% formic acid, 30%-100% eluant gradient) to yield the desired product (46.0 mg, 13%). $^1$H NMR (400 MHz, d6-DMSO): δ 13.07 (s, 1H), 8.87 (s, 1H), 8.29 (s, 1H), 8.17 (s, 1H), 7.76 (m, 2H), 7.27 (s, 1H), 6.96 (s, 2H). MS (EI) for C$_{14}$H$_9$Cl$_2$N$_5$O: 334.2 (M+H).

Example 8

N-[5-Chloro-2-(1H-tetrazol-5-yl)phenyl]isoxazole-5-carboxamide

The title compound was prepared essentially according to the method of Example 4, but using 5-Chloro-2-(1H-tetrazol-5-yl)aniline (1.0 mmol) and isoxazole-5-carbonyl chloride. After precipitation the product was further purified by reverse phase C18 preparative HPLC (water/acetonitrile containing 0.1% formic acid 30%-100% gradient) to yield the desired product (61.1 mg, 21%). $^1$H NMR (400 MHz, d6-DMSO): δ 11.90 (s, 1H), 8.90 (s, 1H), 8.52 (s, 1H), 8.06 (d, 1H), 7.96 (s, 1H), 7.56 (dd, 1H), 7.30 (s, 1H). MS (EI) for C$_{11}$H$_7$ClN$_6$O$_2$: 290.7 (M+H).

Example 9

N-[5-Chloro-2-(1H-tetrazol-5-yl)phenyl]-1-benzothiophene-2-carboxamide

The title compound was prepared essentially according to the method of Example 4, but using 5-Chloro-2-(1H-tetrazol-5-yl)aniline (1.0 mmol) and benzo[b]thiophene-2-carbonyl chloride. After precipitation, the product was further purified by recrystallization in ethanol to yield the desired product (19.6 mg, 5%). $^1$H NMR (400 MHz, d6-DMSO): δ 8.61 (s, 1H), 8.31 (s, 1H), 8.09 (m, 3H), 7.53 (m, 3H). MS (EI) for C$_{16}$H$_{10}$ClN$_5$OS: 355.8 (M+H).

Example 10

4-Chloro-N-(5-chloro-2-(1H-tetrazol-5-yl)phenyl)benzamide

The title compound was prepared essentially according to the method of Example 4, but using 5-Chloro-2-(1H-tetrazol-5-yl)aniline (1.0 mmol) and 4-chlorobenzoyl chloride to yield the desired product (126.3 mg, 37%). $^1$H NMR (400 MHz, d6-DMSO): δ 13.62 (s, 1H), 8.87 (s, 1H), 8.22 (m, 3H), 7.72 (s, 2H), 7.25 (s, 1H). MS (EI) for $C_{14}H_9Cl_2N_5O$: 334.165 (M+H).

Example 11

N-[5-Chloro-2-(1H-tetrazol-5-yl)phenyl]-2-{[2-(4-methylpiperazin-1-yl)phenyl]oxy}acetamide The compound was prepared from N-[5-chloro-2-(1H-tetrazol-5-yl)phenyl]benzamide in using essentially the method of example 4 and preparing the acid chloride as outlined below.

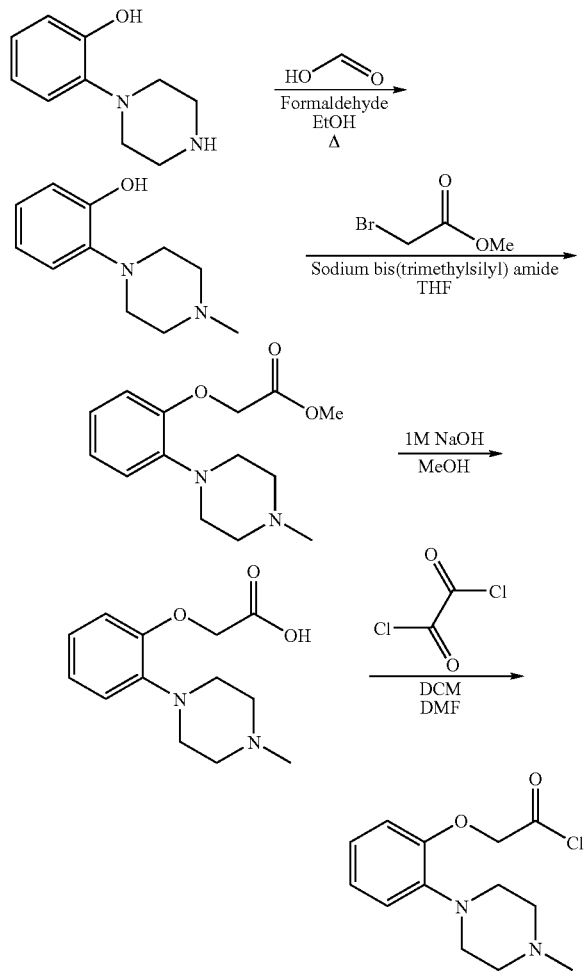

Step 1: 2-(4-Methylpiperazin-1-yl)phenol: To a solution of 2-piperazin-1-yl-phenol (2 g, 11.22 mmol) in 50 mL of EtOH, formic acid (224.43 mmol, 20 eq.) and formaldehyde (62.84 mmol, 5.6 eq.) were added. The reaction was stirred and refluxed at 90° C. for 4 hours. The crude reaction mixture was cooled to room temperature and concentrated in vacuo. The residue was dissolved into ethyl acetate and extracted with an aqueous solution of 0.1M NaOH and then an aqueous solution of saturated sodium bicarbonate. The organic layer was collected, dried with $Mg_2SO_4$, filtered, and concentrated down to afford 1.52 g of phenol 2-(4-methylpiperazin-1-yl) phenol. MS (EI) for $C_{11}H_{16}N_2O$: 193 (M+H).

Step 2: Methyl 2-(2-(4-methylpiperazin-1-yl)phenoxy)acetate: To a solution of 2-(4-methylpiperazin-1-yl)phenol (200 mg, 1.04 mmol) in 5 mL THF were added methyl bromoacetate (1.30 mmol, 1.25 eq.) and sodium bis(trimethylsilyl) amide (2M in THF, 1.14 mmol, 1.10 eq.). The reaction was stirred at room temperature for 1.5 hours and slowly became heterogeneous. The solid from the crude reaction mixture was filtered off and discarded. The solvent was removed in vacuo to afford 238.7 mg of the crude product that was determined to be contaminated with a small amount of the phenol starting material. This material was used without further characterization. MS (EI) for $C_{14}H_{20}N_2O_3$: 265 (M+H).

Step 3: 2-(2-(4-Methylpiperazin-1-yl)phenoxy)acetic acid: To a solution of crude methyl 2-(2-(4-methylpiperazin-1-yl) phenoxy)acetate (238.7 mg, 0.90 mmol) in 20 mL of MeOH, 2.5 mL of 1 M NaOH was added. The reaction was stirred at room temperature overnight. The crude reaction mixture was diluted with water and acidified by 1M HCl to a pH of 4. The solvent was removed in vacuo and the residue was purified by C-18 reverse phase HPLC on a Waters Corp FractionLynx System using a binary eluant gradient of water/acetonitrile each containing 0.1% formic acid to afford 135 mg of 2-(2-(4-methylpiperazin-1-yl)phenoxy)acetic acid. MS (EI) for $C_{13}H_{18}N_2O_3$: 251 (M+H).

Step 4: 2-(2-(4-Methylpiperazin-1-yl)phenoxy)acetyl chloride: To a solution of the acid 2-(2-(4-methylpiperazin-1-yl) phenoxy)acetic acid (135 mg, 0.54 mmol) in 5.4 mL of DCM were added 30 μL of DMF and oxalyl chloride (1.08 mmol, 2 eq.). The reaction was stirred at room temperature for 3 hours. The crude reaction mixture was concentrated down in vacuo to afford 130 mg of 2-(2-(4-Methylpiperazin-1-yl)phenoxy) acetyl chloride. This material was used without further purification. MS (EI) for $C_{13}H_{17}ClN_2O_2$: 269 (M+H).

Step 5: N-[5-Chloro-2-(1H-tetrazol-5-yl)phenyl]-2-{[2-(4-methylpiperazin-1-yl)phenyl]oxy}acetamide: To a solution of N-[5-chloro-2-(1H-tetrazol-5-yl)phenyl]benzamide (47.5 mg, 0.24 mmol) in 1.5 mL of DCM was added 130 μL of DIPEA (0.72 mmol, 3 eq.), and 1 mL of a 0.48M solution of 2-(2-(4-methylpiperazin-1-yl)phenoxy)acetyl chloride (0.48 mmol, 2 eq.). The reaction was stirred at room temperature overnight. The crude reaction mixture was concentrated in vacuo. The crude material was redissolved in methanol and purified by reverse phase C18 preparative HPLC (water/acetonitrile containing 0.1% formic acid 30%-100% gradient) to yield 70 mg of the final product. $^1$H-NMR (400 MHz, $d_6$-DMSO): δ 11.65 (s, 1H), 9.50 (s, br, 1H), 8.65 (d, 1H), 8.04 (d, 1H), 7.47 (dd, 1H), 7.09-7.00 (m, 4H), 4.82 (s, 2H), 3.76 (d, 4H), 3.46 (d, 4H), 2.82 (s, 3H). MS (EI) $C_{20}H_{22}ClN_7O_2$: 428 (M+H).

General Library Procedure

Parallel Synthesis of tetrazole analogs from 5-chloro-2-(1H-tetrazol-5-yl)aniline Synthetic method: Each 2-dram vial was charged with a unique acid chloride (0.5 mmol, 5 equiv.). Then, a 1.0 mL solution of 5-Chloro-2-(1H-tetrazol-5-yl)aniline (0.1 M in dichloroethane, 0.1 mmol) was added to each vial along with 96 uL of diisopropylethylamine (0.54 mmol, 5.4 equiv.). The vials were capped and shaken for 2 hr. at room temperature. The caps were removed from the vials and the solvent evaporated in a vacuum centrifuge. The product residues were dissolved in a solution of 1:1 methanol:dimethylformamide and were purified by C-18 reverse phase HPLC on a Waters Corp FractionLynx System using a binary eluant gradient of water/acetonitrile each containing 0.1% formic acid. The collected fractions were analyzed by LC/MS and fractions containing the desired compound with the greatest purity were combined and concentrated in pre-tared vials. All acid chlorides were obtained from Sigma Aldrich. The 5-Chloro-2-(1H-tetrazol-5-yl)aniline was prepared as described above.

Example 12

N-[5-Chloro-2-(1H-tetrazol-5-yl)phenyl]-2,2-dimethylpropionamide

This compound was synthesized according to the general library procedure using pivaloyl chloride. Isolated amount of material: 2.1 mg; HPLC purity: 100%; MS (EI) for $C_{12}H_{14}ClN_5O$: m/z 280 (M+H).

Example 13

4-Methoxy-N-[5-chloro-2-(1H-tetrazol-5-yl)phenyl]benzamide

This compound was synthesized according to the general library procedure using 4-methoxybenzoyl chloride. Isolated amount of material: 12.0 mg; HPLC purity: 100%; MS (EI) for $C_{15}H_{12}ClN_5O_2$: m/z 330 (M+H).

Example 14

N-[5-Chloro-2-(1H-tetrazol-5-yl)phenyl]cyclohexanecarboxamide

This compound was synthesized according to the general library procedure using cyclohexanecarbonyl chloride. Isolated amount of material: 2.5 mg; HPLC purity: 100%; MS (EI) for $C_{14}H_{16}ClN_5O$: m/z 306 (M+H).

Example 15

N-[5-Chloro-2-(1H-tetrazol-5-yl)phenyl]-2-methylpropanamide

This compound was synthesized according to the general library procedure using isobutyryl chloride. Isolated amount of material: 1.8 mg; HPLC purity: 100%; MS (EI) for $C_{11}H_{12}ClN_5O$: m/z 266 (M+H).

Example 16

N-[5-Chloro-2-(1H-tetrazol-5-yl)phenyl]-2-methylbutanamide

This compound was synthesized according to the general library procedure using 2-methylbutanoyl chloride. Isolated amount of material: 2.6 mg; HPLC purity: 100%; MS (EI) for $C_{12}H_{14}ClN_5O$: m/z 280 (M+H).

Example 17

N-[5-Chloro-2-(1H-tetrazol-5-yl)phenyl]-4-methyl-1,2,3-thiadiazole-5-carboxamide This compound was synthesized according to the general library procedure using 4-methyl-1,2,3-thiadiazole-5-carbonyl chloride. Isolated amount of material: 3.5 mg; HPLC purity: 100%; MS (EI) for $C_{11}H_8ClN_7OS$: m/z 322 (M+H).

Example 18

N-[5-Chloro-2-(1H-tetrazol-5-yl)phenyl]-2-cyclopentylacetamide

This compound was synthesized according to the general library procedure using 2-cyclopentylacetyl chloride. Isolated amount of material: 2.6 mg; HPLC purity: 100%; MS (EI) for $C_{14}H_{16}ClN_5O$: m/z 306 (M+H).

Example 19

(4R)—N-[5-Chloro-2-(1H-tetrazol-5-yl)phenyl]-4,7,7-trimethyl-3-oxo-2-oxabicyclo[2.2.1]heptane-1-carboxamide This compound was synthesized according to the general library procedure using (4R)-4,7,7-trimethyl-3-oxo-2-oxabicyclo[2.2.1]heptane-1-carbonyl chloride. Isolated amount of material: 2.6 mg; HPLC purity: 100%; MS (EI) for $C_{17}H_{18}ClN_5O_3$: m/z 376 (M+H).

Example 20

N-[5-Chloro-2-(1H-tetrazol-5-yl)phenyl]-3-methylbutanamide

This compound was synthesized according to the general library procedure using 3-methylbutanoyl chloride. Isolated amount of material: 2.1 mg; HPLC purity: 100%; MS (EI) for $C_{12}H_{14}ClN_5O$: m/z 280 (M+H).

Example 21

2-(2-Bromophenyl)-N-[5-chloro-2-(1H-tetrazol-5-yl)phenyl]acetamide

This compound was synthesized according to the general library procedure using 2-(2-bromophenyl)acetyl chloride. Isolated amount of material: 5.1 mg; HPLC purity: 100%; MS (EI) for $C_{15}H_{11}BrClN_5O$: m/z 393 (M+H).

Example 22

N-[5-Chloro-2-(1H-tetrazol-5-yl)phenyl]-5-methylisoxazole-3-carboxamide

This compound was synthesized according to the general library procedure using 5-methylisoxazole-3-carbonyl chloride. Isolated amount of material: 3.3 mg; HPLC purity: 100%; MS (EI) for $C_{12}H_9ClN_6O_2$: m/z 305 (M+H).

Example 23

N-[5-Chloro-2-(1H-tetrazol-5-yl)phenyl]-2-(2-thienyl)acetamide

This compound was synthesized according to the general library procedure using 2-(thiophen-2-yl)acetyl chloride. Isolated amount of material: 2.7 mg; HPLC purity: 100%; MS (EI) for $C_{13}H_{10}ClN_5OS$: m/z 320 (M+H).

Example 24

N-[5-Chloro-2-(1H-tetrazol-5-yl)phenyl]-2-methylpentanamide

This compound was synthesized according to the general library procedure using 2-methylpentanoyl chloride. Isolated amount of material: 3.3 mg; HPLC purity: 100%; MS (EI) for $C_{13}H_{16}ClN_5O$: m/z 294 (M+H).

Example 25

3-Chloro-N-[5-chloro-2-(1H-tetrazol-5-yl)phenyl]-1-benzothiophene-2-carboxamide

This compound was synthesized according to the general library procedure using 3-chlorobenzo[b]thiophene-2-carbonyl chloride. Isolated amount of material: 2.3 mg; HPLC purity: 95%; MS (EI) for $C_{16}H_{19}Cl_2N_5OS$: m/z 391 (M+H).

Example 26

N-[5-Chloro-2-(1H-tetrazol-5-yl)phenyl]pentanamide

This compound was synthesized according to the general library procedure using 2 pentanoyl chloride. Isolated amount of material: 2.5 mg; HPLC purity: 100%; MS (EI) for $C_{12}H_{14}ClN_5O$: m/z 280 (M+H).

Example 27

(3s,5s,7s)-N-[5-Chloro-2-(1H-tetrazol-5-yl)phenyl] tricyclo[3.3.1.1~3,7~]decane-1-carboxamide This compound was synthesized according to the general library procedure using 1-adamantanecarboxylic acid chloride. Isolated amount of material: 1.9 mg; HPLC purity: 100%; MS (EI) for $C_{18}H_{20}ClN_5O$: m/z 358 (M+H).

Example 28

N-[5-Chloro-2-(1H-tetrazol-5-yl)phenyl]-2-ethylbutanamide

This compound was synthesized according to the general library procedure using 2-ethylbutanoyl chloride. Isolated amount of material: 2.0 mg; HPLC purity: 100%; MS (EI) for $C_{13}H_{16}ClN_5O$: m/z 294 (M+H).

Example 29

N-[5-Chloro-2-(1H-tetrazol-5-yl)phenyl]butanamide

This compound was synthesized according to the general library procedure using butyryl chloride. Isolated amount of material: 2.3 mg; HPLC purity: 100%; MS (EI) for $C_{11}H_{12}ClN_5O$: m/z 266 (M+H).

Example 30

N-[5-Chloro-2-(1H-tetrazol-5-yl)phenyl]cyclopentanecarboxamide

This compound was synthesized according to the general library procedure using cyclopentanecarbonyl chloride. Isolated amount of material: 2.1 mg; HPLC purity: 85%; MS (EI) for $C_{13}H_{14}ClN_5O$: m/z 292 (M+H).

Example 31

N-[5-Chloro-2-(1H-tetrazol-5-yl)phenyl]-3,5-dimethylisoxazole-4-carboxamide

This compound was synthesized according to the general library procedure using 3,5-dimethylisoxazole-4-carbonyl chloride. Isolated amount of material: 2.4 mg; HPLC purity: 100%; MS (EI) for $C_{13}H_{11}ClN_6O_2$: m/z 319 (M+H).

Example 32

N-[5-Chloro-2-(1H-tetrazol-5-yl)phenyl]propanamide

This compound was synthesized according to the general library procedure using propionyl chloride. Isolated amount of material: 2.4 mg; HPLC purity: 100%; MS (EI) for $C_{10}H_{10}ClN_5O$: m/z 252 (M+1).

Example 33

N-[5-Chloro-2-(1H-tetrazol-5-yl)phenyl]-2-phenylacetamide

This compound was synthesized according to the general library procedure using 2-phenylacetyl chloride. Isolated amount of material: 3.1 mg; HPLC purity: 100%; MS (EI) for $C_{15}H_{12}ClN_5O$: m/z 314 (M+H).

Example 34

N-[5-Chloro-2-(1H-tetrazol-5-yl)phenyl]-4-methylpentanamide

This compound was synthesized according to the general library procedure using 4-methylpentanoyl chloride. Isolated amount of material: 1.9 mg; HPLC purity: 82%; MS (EI) for $C_{13}H_{16}ClN_5O$: m/z 294 (M+H).

Example 35

N-[5-Chloro-2-(1H-tetrazol-5-yl)phenyl]-2-(methyloxy)acetamide

This compound was synthesized according to the general library procedure using 2-methoxyacetyl chloride. Isolated amount of material: 2.4 mg; HPLC purity: 100%; MS (EI) for $C_{10}H_{10}ClN_5O_2$: m/z 268 (M+H).

Example 36

1-Acetyl-N-[5-chloro-2-(1H-tetrazol-5-yl)phenyl] piperidine-4-carboxamide

This compound was synthesized according to the general library procedure using 1-acetylpiperidine-4-carbonyl chloride. Isolated amount of material: 5.0 mg; HPLC purity: 100%; MS (EI) for $C_{15}H_{17}ClN_6O_2$: m/z 349 (M+H).

Example 37

N-[5-Chloro-2-(1H-tetrazol-5-yl)phenyl]-2-phenylbutanamide

This compound was synthesized according to the general library procedure using 2-phenylbutanoyl chloride. Isolated amount of material: 1.5 mg; HPLC purity: 80%; MS (EI) for $C_{17}H_{16}ClN_5O$: m/z 342 (M+H).

Example 38

N-[5-Chloro-2-(1H-tetrazol-5-yl)phenyl]-N~2~,N~2~-dimethylglycinamide

This compound was synthesized according to the general library procedure using 2-(dimethylamino)acetyl chloride. Isolated amount of material: 3.2 mg; HPLC purity: 100%; MS (EI) for $C_{11}H_{13}ClN_6O$: m/z 281 (M+H).

Example 39

Ethyl 3-{[5-Chloro-2-(1H-tetrazol-5-yl)phenyl]amino}-3-oxopropanoate

This compound was synthesized according to the general library procedure using ethyl 3-chloro-3-oxopropanoate. Isolated amount of material: 2.4 mg; HPLC purity: 87%; MS (EI) for $C_{12}H_{12}ClN_5O_3$: m/z 310 (M+H).

Example 40

N-[5-Chloro-2-(1H-tetrazol-5-yl)phenyl]-5-methyl-3-phenylisoxazole-4-carboxamide This compound was synthesized according to the general library procedure using 5-methyl-3-phenylisoxazole-4-carbonyl chloride. Isolated amount of material: 4.5 mg; HPLC purity: 100%; MS (EI) for $C_{18}H_{13}ClN_6O_2$: m/z 381 (M+H).

Example 41

N-[5-Chloro-2-(1H-tetrazol-5-yl)phenyl]-3-methyl-1-benzofuran-2-carboxamide

This compound was synthesized according to the general library procedure using 3-methylbenzofuran-2-carbonyl chloride. Isolated amount of material: 1.1 mg; HPLC purity: 100%; MS (EI) for $C_{17}H_{12}ClN_5O_2$: m/z 354 (M+H).

Example 42

N-[5-Chloro-2-(1H-tetrazol-5-yl)phenyl]-2-ethylhexanamide

This compound was synthesized according to the general library procedure using 2-ethylhexanoyl chloride. Isolated amount of material: 7.7 mg; HPLC purity: 100%; MS (EI) for $C_{15}H_{20}ClN_5O$: m/z 322 (M+H).

Example 43

N-[5-Chloro-2-(1H-tetrazol-5-yl)phenyl]-2-(phenyloxy)acetamide

This compound was synthesized according to the general library procedure using 2-phenoxyacetyl chloride. Isolated amount of material: 4.7 mg; HPLC purity: 100%; MS (EI) for $C_{15}H_{12}ClN_5O_2$: m/z 330 (M+H).

Example 44

Methyl 4-{[5-Chloro-2-(1H-tetrazol-5-yl)phenyl]amino}-4-oxobutanoate

This compound was synthesized according to the general library procedure using methyl 4-chloro-4-oxobutanoate. Isolated amount of material: 4.8 mg; HPLC purity: 91%; MS (EI) for $C_{12}H_{12}ClN_5O_3$: m/z 310 (M+H).

Example 45

(1R,2R)—N-[5-Chloro-2-(1H-tetrazol-5-yl)phenyl]-2-phenylcyclopropanecarboxamide

This compound was synthesized according to the general library procedure using (1R,2R)-2-phenylcyclopropanecarbonyl chloride. Isolated amount of material: 7.3 mg; HPLC purity: 100%; MS (EI) for $C_{17}H_{14}ClN_5O$: m/z 340 (M+H).

Example 46

N-[5-Chloro-2-(1H-tetrazol-5-yl)phenyl]-2-[3-(methyloxy)phenyl]acetamide

This compound was synthesized according to the general library procedure using 2-(3-methoxyphenyl)acetyl chloride. Isolated amount of material: 5.9 mg; HPLC purity: 83%; MS (EI) for $C_{16}H_{14}ClN_5O_2$: m/z 344 (M+H).

Example 47

N-[5-Chloro-2-(1H-tetrazol-5-yl)phenyl]-2,2-diphenylacetamide

This compound was synthesized according to the general library procedure using 2,2-diphenylacetyl chloride. Isolated amount of material: 9.0 mg; HPLC purity: 100%; MS (EI) for $C_{21}H_{16}ClN_5O$: m/z 390 (M+H).

Example 48

3-(2-Chlorophenyl)-N-[5-chloro-2-(1H-tetrazol-5-yl)phenyl]-5-methylisoxazole-4-carboxamide This compound was synthesized according to the general library procedure using 3-(2-chlorophenyl)-5-methylisoxazole-4-carbonyl chloride. Isolated amount of material: 8.4 mg; HPLC purity: 100%; MS (EI) for $C_{18}H_{12}Cl_2N_6O_2$: m/z 415 (M+H).

Example 49

2-Chloro-N-[5-chloro-2-(1H-tetrazol-5-yl)phenyl]pyridine-3-carboxamide

This compound was synthesized according to the general library procedure using 2-chloronicotinoyl chloride. Isolated amount of material: 6.6 mg; HPLC purity: 100%; MS (EI) for $C_{13}H_8Cl_2N_6O$: m/z 335 (M+H).

Example 50

N-[5-Chloro-2-(1H-tetrazol-5-yl)phenyl]-2-(methylthio)pyridine-3-carboxamide

This compound was synthesized according to the general library procedure using 2-(methylthio)nicotinoyl chloride.

Isolated amount of material: 5.2 mg; HPLC purity: 100%; MS (EI) for $C_{14}H_{11}ClN_6OS$: m/z 347 (M+H).

Example 51

3-(2-Chloro-6-fluorophenyl)-N-[5-chloro-2-(1H-tetrazol-5-yl)phenyl]-5-methylisoxazole-4-carboxamide This compound was synthesized according to the general library procedure using 3-(2-chloro-6-fluorophenyl)-5-methylisoxazole-4-carbonyl chloride. Isolated amount of material: 8.8 mg; HPLC purity: 100%; MS (EI) for $C_{18}H_{11}Cl_2FN_6O_2$: m/z 433 (M+H).

Example 52

3-Chloro-N-[5-chloro-2-(1H-tetrazol-5-yl)phenyl]-4-(methylsulfonyl)thiophene-2-carboxamide This compound was synthesized according to the general library procedure using 3-chloro-4-(methylsulfonyl)thiophene-2-carbonyl chloride. Isolated amount of material: 2.6 mg; HPLC purity: 100%; MS (EI) for $C_{13}H_9Cl_2N_5O_3S_2$: m/z 418 (M+H).

Example 53

N-[5-Chloro-2-(1H-tetrazol-5-yl)phenyl]-2,5-dimethylfuran-3-carboxamide

This compound was synthesized according to the general library procedure using 2,5-dimethylfuran-3-carbonyl chloride. Isolated amount of material: 1.5 mg; HPLC purity: 82%; MS (EI) for $C_{14}H_{12}ClN_5O_2$: m/z 318 (M+H).

Example 54

N-[5-Chloro-2-(1H-tetrazol-5-yl)phenyl]pent-4-enamide

This compound was synthesized according to the general library procedure using pent-4-enoyl chloride. Isolated amount of material: 5.7 mg; HPLC purity: 90%; MS (EI) for $C_{12}H_{12}ClN_5O$: m/z 278 (M+H).

Example 55

N-[5-Chloro-2-(1H-tetrazol-5-yl)phenyl]-3,5-bis(trifluoromethyl)benzamide

This compound was synthesized according to the general library procedure using 3,5-bis(trifluoromethyl)benzoyl chloride. Isolated amount of material: 10.1 mg; HPLC purity: 100%; MS (EI) for $C_{16}H_8ClF_6N_5O$: m/z 436 (M+H).

Example 56

N-[5-Chloro-2-(1H-tetrazol-5-yl)phenyl]-2-fluorobenzamide

This compound was synthesized according to the general library procedure using 2-fluorobenzoyl chloride. Isolated amount of material: 9.0 mg; HPLC purity: 100%; MS (EI) for $C_{14}H_9ClFN_5O$: m/z 318 (M+H).

Example 57

N-[5-Chloro-2-(1H-tetrazol-5-yl)phenyl]-2,4-difluorobenzamide

This compound was synthesized according to the general library procedure using 2,4-difluorobenzoyl chloride. Isolated amount of material: 9.1 mg; HPLC purity: 100%; MS (EI) for $C_{14}H_8ClF_2N_5O$: m/z 336 (M+H).

Example 58

N-[5-Chloro-2-(1H-tetrazol-5-yl)phenyl]-2,6-difluorobenzamide

This compound was synthesized according to the general library procedure using 2,6-difluorobenzoyl chloride. Isolated amount of material: 6.9 mg; HPLC purity: 98%; MS (EI) for $C_{14}H_8ClF_2N_5O$: m/z 336 (M+H).

Example 59

2,4-Dichloro-N-[5-chloro-2-(1H-tetrazol-5-yl)phenyl]benzamide

This compound was synthesized according to the general library procedure using 2,4-dichlorobenzoyl chloride. Isolated amount of material: 8.5 mg; HPLC purity: 100%; MS (EI) for $C_{14}H_8Cl_3N_5O$: m/z 368 (M+H).

Example 60

N-[5-Chloro-2-(1H-tetrazol-5-yl)phenyl]-2-(trifluoromethyl)benzamide

This compound was synthesized according to the general library procedure using 2-(trifluoromethyl)benzoyl chloride. Isolated amount of material: 7.8 mg; HPLC purity: 100%; MS (EI) for $C_{15}H_9ClF_3N_5O$: m/z 368 (M+H).

Example 61

N-[5-Chloro-2-(1H-tetrazol-5-yl)phenyl]-2-methylbenzamide

This compound was synthesized according to the general library procedure using 2-methylbenzoyl chloride. Isolated amount of material: 8.9 mg; HPLC purity: 100%; MS (EI) for $C_{15}H_{12}ClN_5O$: m/z 314 (M+H).

Example 62

3-Bromo-N-[5-chloro-2-(1H-tetrazol-5-yl)phenyl]benzamide

This compound was synthesized according to the general library procedure using 3-bromobenzoyl chloride. Isolated amount of material: 9.5 mg; HPLC purity: 100%; MS (EI) for $C_{14}H_9BrClN_5O$: m/z 378 (M+1).

Example 63

N-[5-Chloro-2-(1H-tetrazol-5-yl)phenyl]-3-fluorobenzamide

This compound was synthesized according to the general library procedure using 3-fluorobenzoyl chloride. Isolated amount of material: 7.3 mg; HPLC purity: 100%; MS (EI) for $C_{14}H_9ClF_2N_5O$: m/z 318 (M+H).

Example 64

3,4-Dichloro-N-[5-chloro-2-(1H-tetrazol-5-yl)phenyl]benzamide

This compound was synthesized according to the general library procedure using 3,4-dichlorobenzoyl chloride. Isolated amount of material: 7.3 mg; HPLC purity: 100%; MS (EI) for $C_{14}H_8Cl_3N_5O$: m/z 368 (M+H).

Example 65

N-[5-Chloro-2-(1H-tetrazol-5-yl)phenyl]-3-(trifluoromethyl)benzamide

This compound was synthesized according to the general library procedure using 3-(trifluoromethyl)benzoyl chloride. Isolated amount of material: 1.5 mg; HPLC purity: 82%; MS (EI) for $C_{15}H_9ClF_3N_5O$: m/z 280 (M+H).

Example 66

N-[5-Chloro-2-(1H-tetrazol-5-yl)phenyl]-3-methylbenzamide

This compound was synthesized according to the general library procedure using 3-methylbenzoyl chloride. Isolated amount of material: 7.9 mg; HPLC purity: 100%; MS (EI) for $C_{15}H_{12}ClN_5O$: m/z 314 (M+H).

Example 67

N-[5-Chloro-2-(1H-tetrazol-5-yl)phenyl]-4-fluorobenzamide

This compound was synthesized according to the general library procedure using 4-fluorobenzoyl chloride. Isolated amount of material: 9.4 mg; HPLC purity: 100%; MS (EI) for $C_{14}H_9ClFN_5O$: m/z 318 (M+H).

Example 68

N-[5-Chloro-2-(1H-tetrazol-5-yl)phenyl]cyclopropanecarboxamide

This compound was synthesized according to the general library procedure using cyclopropanecarbonyl chloride. Isolated amount of material: 8.0 mg; HPLC purity: 100%; MS (EI) for $C_{11}H_{104}ClN_5O$: m/z 264 (M+H).

Example 69

5-Chloro-N-[5-chloro-2-(1H-tetrazol-5-yl)phenyl]-1-methyl-1H-pyrazole-4-carboxamide This compound was synthesized according to the general library procedure using 5-chloro-1-methyl-1H-pyrazole-4-carbonyl chloride. Isolated amount of material: 2.2 mg; HPLC purity: 94%; MS (EI) for $C_{12}H_9Cl_2N_7O$: m/z 338 (M+H).

Example 70

N-[5-Chloro-2-(1H-tetrazol-5-yl)phenyl]-3-phenylpropanamide

This compound was synthesized according to the general library procedure using 3-phenylpropanoyl chloride. Isolated amount of material: 3.9 mg; HPLC purity: 100%; MS (EI) for $C_{16}H_{14}ClN_5O$: m/z 328 (M+H).

Example 71

2-[(4-Chlorophenyl)oxy]-N-[5-chloro-2-(1H-tetrazol-5-yl)phenyl]acetamide

This compound was synthesized according to the general library procedure using 2-(4-chlorophenoxy)acetyl chloride. Isolated amount of material: 4.8 mg; HPLC purity: 100%; MS (EI) for $C_{15}H_{11}Cl_2N_5O_2$: m/z 365 (M+H).

Example 72

2-[(3-Chlorophenyl)oxy]-N-[5-chloro-2-(1H-tetrazol-5-yl)phenyl]acetamide

This compound was synthesized according to the general library procedure using 2-(3-chlorophenoxy)acetyl chloride. Isolated amount of material: 5.7 mg; HPLC purity: 100%; MS (EI) for $C_{15}H_{11}Cl_2N_5O_2$: m/z 365 (M+H).

Example 73

N-[5-Chloro-2-(1H-tetrazol-5-yl)phenyl]-2-{[3-(methyloxy)phenyl]oxy}acetamide This compound was synthesized according to the general library procedure using 2-(3-methoxyphenoxy)acetyl chloride. Isolated amount of material: 6.1 mg; HPLC purity: 100%; MS (EI) for $C_{16}H_{14}ClN_5O_3$: m/z 360 (M+H).

Example 74

N-[5-Chloro-2-(1H-tetrazol-5-yl)phenyl]-3-(phenyloxy)propanamide

This compound was synthesized according to the general library procedure using 3-phenoxypropanoyl chloride. Isolated amount of material: 2.6 mg; HPLC purity: 100%; MS (EI) for $C_{16}H_{14}ClN_5O_2$: m/z 344 (M+H).

Example 75

N-[5-Chloro-2-(1H-tetrazol-5-yl)phenyl]-3-[(4-fluorophenyl)oxy]propanamide

This compound was synthesized according to the general library procedure using 3-(4-fluorophenoxy)propanoyl chloride. Isolated amount of material: 5.2 mg; HPLC purity: 100%; MS (EI) for $C_{16}H_{13}ClFN_5O_2$: m/z 362 (M+H).

Example 76

N-[5-Chloro-2-(1H-tetrazol-5-yl)phenyl]cyclobutanecarboxamide

This compound was synthesized according to the general library procedure using cyclobutanecarbonyl chloride. Isolated amount of material: 5.0 mg; HPLC purity: 100%; MS (EI) for $C_{12}H_{12}ClN_5O$: m/z 278 (M+H).

Example 77

N-[5-Methyl-2-(1H-tetrazol-5-yl)phenyl]thiophene-2-carboxamide

The compound was synthesized as outlined in the following synthetic sequence.

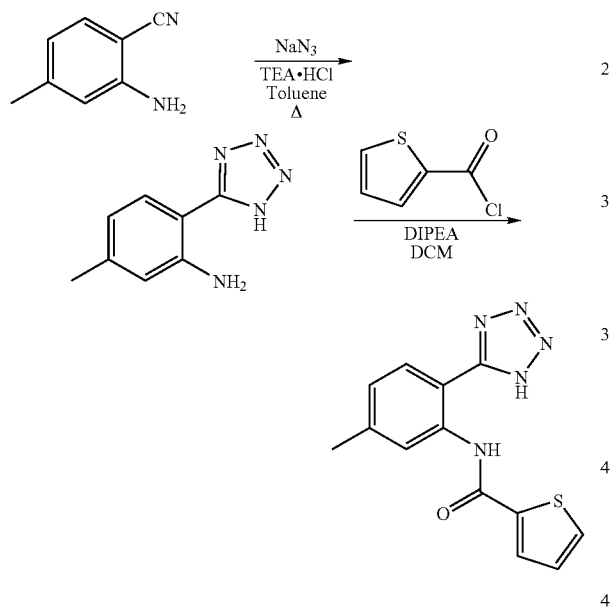

Step 1: 5-Methyl-2-(1H-tetrazol-5-yl)aniline: To a mixture of 2-amino-4-methylbenzonitrile (500 mg, 3.3 mmol), sodium azide (4.3 mmol, 1.3 eq.), and triethylamine hydrochloride (4.3 mmol, 1.3 eq.) in a sealed tube, 8 mL of toluene was added. The tube was tightly capped and the reaction was stirred and heated to 100° C. overnight. The mixture was cooled to room temperature, diluted with another 10 mL of toluene, transferred to a separatory funnel and washed 3×20 mL with water. The aqueous layer was collected and acidified to a pH of 4 with concentrated HCl. The solid was collected by filtration, washed with acetonitrile, and dried under vacuum to afford 244 mg of 5-methyl-2-(1H-tetrazol-5-yl) aniline. MS (EI) for $C_8H_9N_5$: 176 (M+H).
Step 2: N-[5-Methyl-2-(1H-tetrazol-5-yl)phenyl]thiophene-2-carboxamide: To a solution of 5-methyl-2-(1H-tetrazol-5-yl)aniline (240 mg, 1.4 mmol) in 6 mL of DCM was added DIPEA (7.5 mmol, 5.5 eq.) followed by thiophene-2-carbonyl chloride (6.8 mmol, 5 eq.). The reaction was stirred at room temperature overnight. The organic solution of the crude reaction mixture was extracted twice with aqueous HCl (0.1 M), twice with aqueous sodium hydroxide (0.1 M), and once with a saturated aqueous solution of sodium chloride. The basic aqueous extractions and final brine extraction were combined and acidified to a pH of 4 with concentrated HCl. The resulting solid was collected by filtration. This crude material was further purified by redissolving the material into minimum volume of aqueous NaOH (0.1 M), and then reacidified with concentrated HCl. The solid was collected by filtration, washed with EtOAc, and dried under vacuum to afford 26.8 mg of the desired product. $^1$H-NMR (400 MHz, $d_6$-DMSO): δ 11.60 (s, 1H), 8.35 (s, 1H), 7.98-7.94 (m, 2H), 7.90 (d, 1H), 7.33 (t, 1H), 7.20 (d, 1H), 2.42 (s, 3H). MS (EI) for $C_{13}H_{11}N_5OS$: 286 (M+H).

Example 78

N-[4-Bromo-2-(1H-tetrazol-5-yl)phenyl]thiophene-2-carboxamide

The compound was synthesized as outlined in the following synthetic sequence.

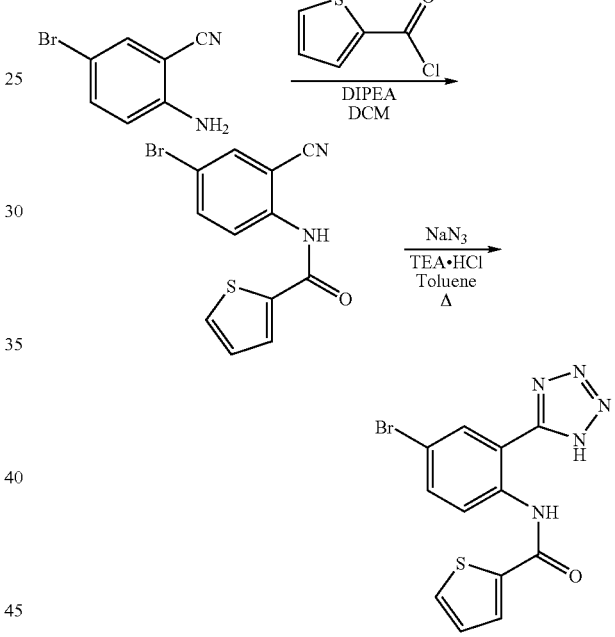

Step 1: N-(4-Bromo-2-cyanophenyl)thiophene-2-carboxamide: To a solution of 2-amino-5-bromobenzonitrile (1 g, 5.1 mmol) in 20 mL of DCM, DIPEA (27.9 mmol, 5.5 eq.) was added followed by thiophene-2-carbonyl chloride (25.4 mmol, 5.0 eq.). The reaction was stirred at room temperature overnight. The organic solution of the crude reaction mixture was extracted twice with aqueous HCl (0.1 M), twice with aqueous sodium hydroxide (0.1 M), and once with a saturated aqueous solution of sodium chloride. The organic layer was dried with magnesium sulfate, filtered and concentrated in vacuo. The residue was purified by column chromatography (silica gel, 20% EtOAc in hexane eluent) to afford 120 mg of N-(4-bromo-2-cyanophenyl)thiophene-2-carboxamide. MS (EI) for $C_{12}H_7BrN_2OS$: 307 (M+H).
Step 2: N-[4-Bromo-2-(1H-tetrazol-5-yl)phenyl]thiophene-2-carboxamide: To a mixture of the nitrile N-(4-bromo-2-cyanophenyl)thiophene-2-carboxamide (120 mg, 0.4 mmol), sodium azide (0.5 mmol, 1.3 eq.), and triethylamine hydrochloride (0.5 mmol, 1.3 eq.) in a sealed tube, 1 mL of toluene was added. The tube was tightly capped and the reaction was stirred and heated to 10° C. overnight. The mixture was cooled to room temperature, diluted with another 5 mL of toluene, transferred to a separatory funnel and washed 3×10 mL with water. The aqueous layer was collected and acidified to a pH of 4 with concentrated HCl. The solid was collected by filtration, washed with acetonitrile, and dried under vacuum to afford 18 mg of desired product. $^1$H-NMR (400 MHz, d$_6$-DMSO): δ 11.60 (s, 1H), 8.44 (d, 1H), 8.23 (d, 1H), 7.99-7.95 (m, 21), 7.82 (dd, 1H), 7.33 (t, 1H). MS (EI) for C$_{12}$H$_8$BrN$_5$OS: 350 (M+H).

Example 79

N-[3-Chloro-2-(1H-tetrazol-5-yl)phenyl]thiophene-2-carboxamide

The compound was synthesized as outlined in the following synthetic sequence.

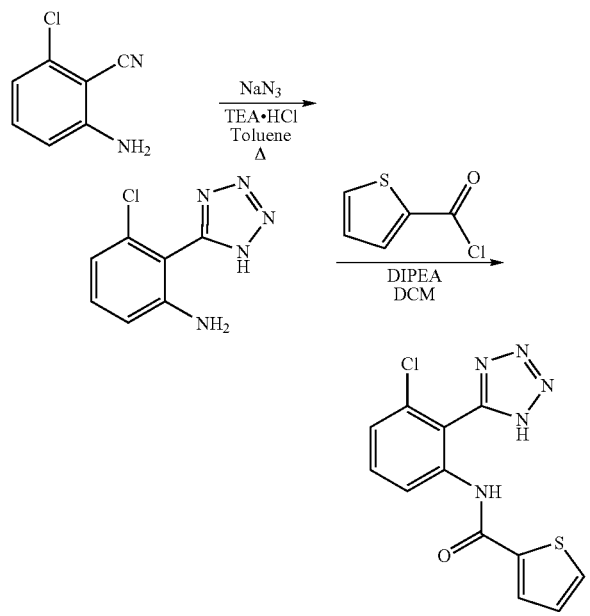

Step 1: 3-Chloro-2-(1H-tetrazol-5-yl)aniline: To a mixture of 2-amino-6-chlorobenzonitrile (500 mg, 3.3 mmol), sodium azide (4.3 mmol, 1.3 eq.), and triethylamine hydrochloride (4.3 mmol, 1.3 eq.) in a sealed tube, 8 mL of toluene was added. The tube was tightly capped and the reaction was stirred and heated to 100° C. overnight. The mixture was cooled to room temperature, diluted with another 10 mL of toluene, transferred to a separatory funnel and washed with water (3×20 mL). The aqueous extractions were combined and acidified to a pH of 4 with concentrated HCl. The solid was collected by filtration, washed with acetonitrile, and dried under vacuum to afford 137 mg of 3-chloro-2-(1H-tetrazol-5-yl)aniline. MS (EI) for C$_7$H$_6$ClN$_5$: 196 (M+H).

Step 2: N-[3-Chloro-2-(1H-tetrazol-5-yl)phenyl]thiophene-2-carboxamide: To a solution of the tetrazole intermediate 3-chloro-2-(1H-tetrazol-5-yl)aniline (137 mg, 0.7 mmol) in 3 mL of DCM, DIPEA (1.4 mmol, 2.0 eq.) was added followed by thiophene-2-carbonyl chloride (1.0 mmol, 1.5 eq.). The reaction was stirred at room temperature overnight. The organic solution of the crude reaction mixture was extracted twice with aqueous HCl (0.1 M), twice with aqueous sodium hydroxide (0.1 M), and once with a saturated aqueous solution of sodium chloride. The basic aqueous extractions and final brine extraction were combined and acidified to a pH of 4 with concentrated HCl. The resulting solid was collected by filtration. This was then washed with acetonitrile, and dried under vacuum to afford 80 mg of desired N-[3-chloro-2-(1H-tetrazol-5-yl)phenyl]thiophene-2-carboxamide. $^1$H-NMR (400 MHz, d$_6$-DMSO): 10.25 (s, 1H), 7.83 (dd, 1H), 7.73 (dd, 1H), 7.68-7.64 (m, 2H), 7.62-7.59 (m, 1H), 7.17 (t, 1H). MS (EI) for C$_{12}$H$_8$ClN$_5$OS: 306 (M+H).

Example 80

N-[2-Chloro-6-(1H-tetrazol-5-yl)phenyl]thiophene-2-carboxamide

The compound was synthesized as outlined in the following synthetic sequence.

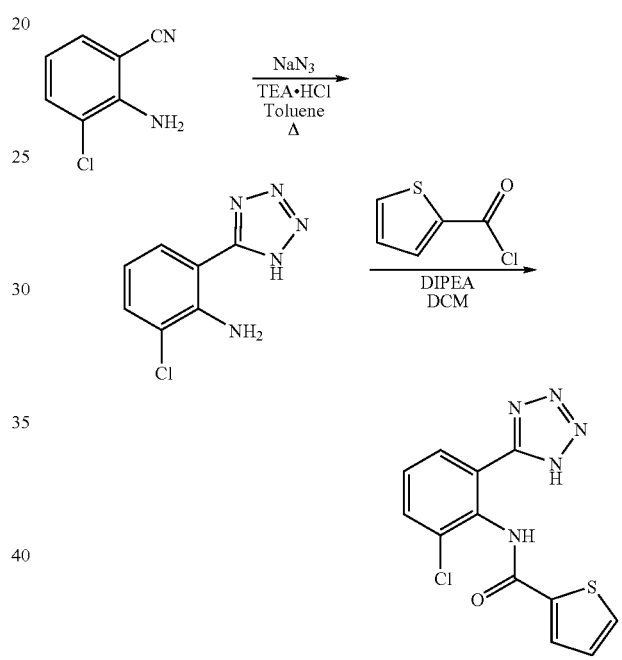

Step 1: 2-Chloro-6-(1H-tetrazol-5-yl)aniline: To a mixture of 2-amino-3-chlorobenzonitrile (500 mg, 3.3 mmol), sodium azide (4.3 mmol, 1.3 eq.), and triethylamine hydrochloride (4.3 mmol, 1.3 eq.) in a sealed tube, 8 mL of toluene was added. The tube was tightly capped and the reaction was stirred and heated to 100° C. overnight. The mixture was cooled to room temperature, diluted with another 10 mL of toluene, transferred to a separatory funnel and washed 3×20 mL with water. The aqueous extractions were collected and acidified to a pH of 4 with concentrated HCl. The solid was collected by filtration, washed with acetonitrile, and dried under vacuum to afford 581 mg of 2-chloro-6-(1H-tetrazol-5-yl)aniline. MS (EI) for C$_7$H$_6$ClN$_5$: 196 (MH$^+$).

Step 2: N-[2-Chloro-6-(1H-tetrazol-5-yl)phenyl]thiophene-2-carboxamide: To a solution of 2-chloro-6-(1H-tetrazol-5-yl)aniline (300 mg, 1.5 mmol) in 8 mL of DCM, DIPEA (3.1 mmol, 2.0 eq.) was added followed by thiophene-2-carbonyl chloride (2.3 mmol, 1.5 eq.). The reaction was stirred at room temperature overnight. The organic solution of the crude reaction mixture was extracted twice with aqueous HCl (0.1 M), twice with aqueous sodium hydroxide (0.1 M), and once with a saturated aqueous solution of sodium chloride. The basic aqueous extractions and final brine extraction were combined and acidified to a pH of 4 with concentrated HCl. The resulting solid was collected by filtration. The material was then washed with acetonitrile, and dried under vacuum to afford 33 mg of desired product. $^1$H-NMR (400 MHz, d$_6$-DMSO): δ 10.32 (s, 1H), 7.96 (d, 1H), 7.87-7.81 (m, 3H), 7.58 (t, 1H), 7.23 (t, 1H). MS (EI) C$_{12}$H$_8$ClN$_5$OS: 306 (M+H).

Example 81

N-[6-(1H-Tetrazol-5-yl)-1H-benzimidazol-5-yl]thiophene-2-carboxamide

The compound was synthesized as outlined in the following synthetic sequence.

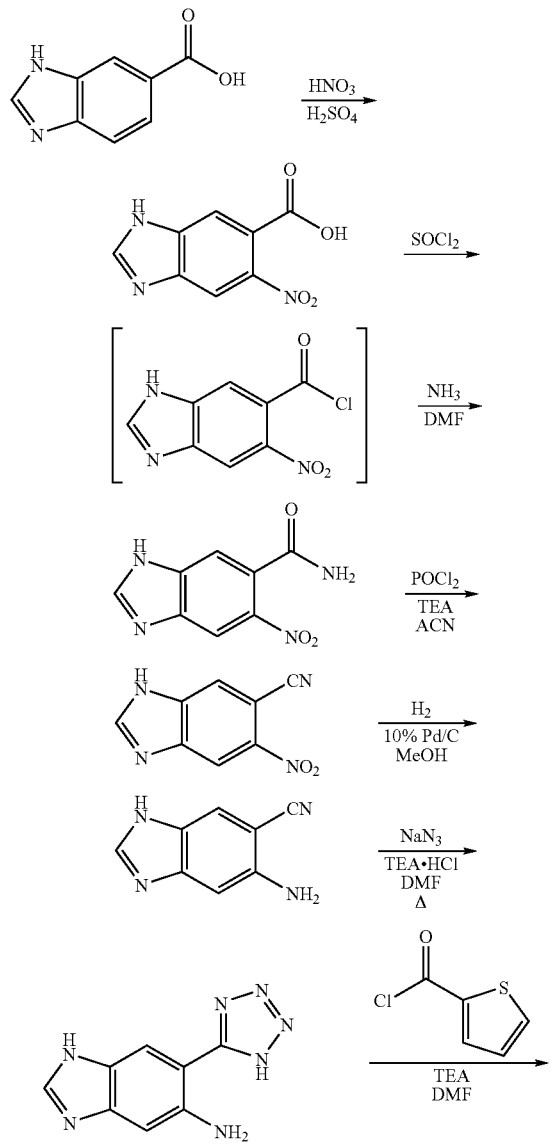

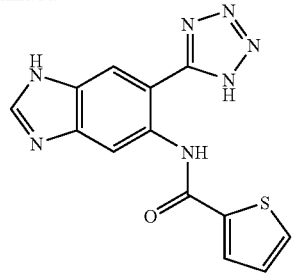

Step 1: 5-Nitro-1H-benzoimidazole-6-carboxylic acid: Benzimidazole-5-carboxylic acid (10 g, 62 mmol) was added to 70 mL of concentrated sulfuric acid cooled in an ice bath. When the solid had dissolved, 6.5 mL of fuming nitric acid was added over 10 min. The ice bath was removed and the reaction mixture was stirred at room temperature for 2 hr. Then, the mixture was poured into 800 mL of ice water. The pH of the aqueous solution was raised to 3 by the addition of solid sodium bicarbonate. The precipitate was filtered, washed with water and air dried. 5.6 g of precipitate was isolated. The material was used without further purification; MS (EI) m/z 208 (M+H).

Step 2: 5-Nitro-1H-benzoimidazole-6-carboxamide: 5-Nitro-1H-benzoimidazole-6-carboxylic acid (5.6 g, 27 mmol) was suspended in 20 mL of thionyl chloride. The suspension was heated at 80° C. for 3 hr. After cooling, the reaction mixture was concentrated under vacuum. The solid was taken up in 100 mL of DMF and cooled in an ice bath under a nitrogen atmosphere. Ammonia gas was bubbled through the reaction mixture for 2 min and the reaction was stirred at room temperature for another 30 min. The reaction mixture was diluted with 100 mL of water. The precipitate was filtered, washed with water and dried under vacuum to give 5 g of crude 5-nitro-1H-benzoimidazole-6-carboxamide. The material was used without further purification; MS (EI) m/z 207 (M+H).

Step 3: 5-Nitro-1H-benzoimidazole-6-carbonitrile: The crude amide 5-Nitro-1H-benzoimidazole-6-carboxamide (5 g, 24 mmol) was suspended in acetonitrile (135 mL) along with triethylamine (15 mL, 110 mmol). Phosphorous oxychloride (10 mL, 110 mmol) was added and the reaction was heated to 85° C. for 5 hr. After cooling, the reaction mixture was poured into 500 mL of ice water. The precipitate was filtered, washed with water and dried under vacuum to give 3.40 g of 5-nitro-1H-benzoimidazole-6-carbonitrile. The material was used without further purification. $^1$H NMR (400 MHz, d$_6$-DMSO): 7.56 (s, 1H), 7.44 (s, 1 μl), 7.31 (s, 1H); MS (EI) for C$_8$H$_4$N$_4$O$_2$: 189 (M+H).

Step 4: 5-Amino-1H-benzoimidazole-6-carbonitrile: The crude nitrile 5-nitro-1H-benzoimidazole-6-carbonitrile (2.0 g, 11 mmol) was dissolved in 50 mL of methanol. 10% Palladium on carbon (200 mg) was added and the reaction mixture was hydrogenated at 30 p.s.i. for 2 hr. The reaction mixture was filtered through Celite and concentrated under vacuum 10 give 1.7 g of crude 5-amino-1H-benzoimidazole-6-carbonitrile. The material was used without further purification; MS (EI) m/z 159 (M+H).

Step 5: 6-(1H-Tetrazol-5-yl)-1H-benzimidazole-5-amine: 5-Amino-1H-benzoimidazole-6-carbonitrile (150 mg, 0.9 mmol), triethylamine hydrochloride (430 mg, 3.1 mmol) and sodium azide (200 mg, 3.1 mmol) were suspended in 2 mL of DMF. The reaction mixture was heated at 100° C. for 2 hr. The reaction mixture was concentrated under vacuum and used without further purification; MS (EI) m/z 202 (M+H).

Step 6: N-[6-(1H-Tetrazol-5-yl)-1H-benzimidazol-5-yl] thiophene-2-carboxamide: The crude 6-(1H-tetrazol-5-yl)-1H-benzimidazole-5-amine (0.9 mmol) was suspended in 5 mL of DMF along with diisopropylethylamine (200 µL, 1.1 mmol). Thiophene-2-carbonyl chloride (100 µL, 0.9 mmol) was added dropwise. The reaction mixture was stirred for 1 hr at room temperature, filtered and purified by reverse phase HPLC to give 1 mg of the desired compound. $^1$H NMR (400 MHz, $d_6$-DMSO): 8.57 (s, 1H), 8.20 (dd, 1H), 8.02 (dd, 1H), 7.94 (d, 1H), 7.38-7.36 (m, 2H); MS (EI) for $C_{13}H_9N_7OS$: 312 (M+H).

Example 82

N-{2-[(Phenylmethyl)amino]-5-(1H-tetrazol-5-yl) pyrimidin-4-yl}thiophene-2-carboxamide The compound was synthesized as outlined in the following synthetic sequence.

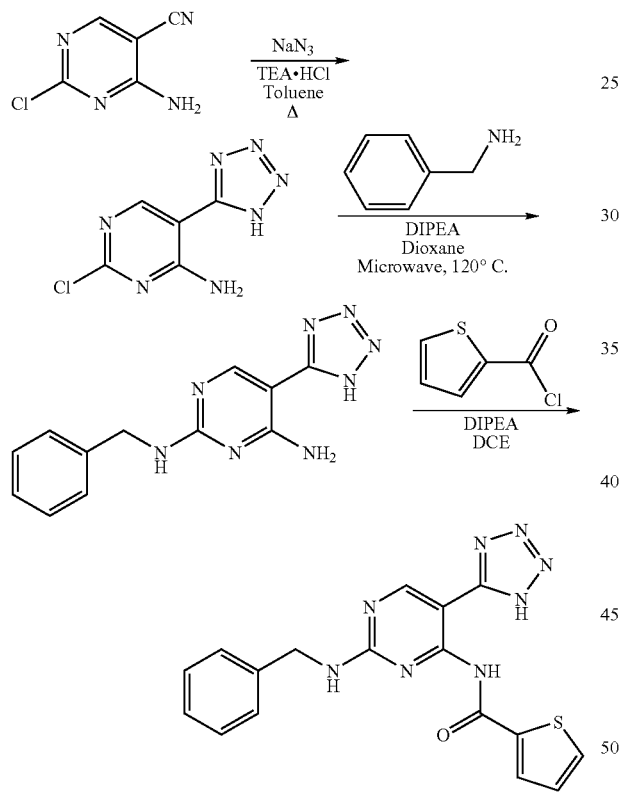

Step 1:
2-Chloro-5-(1H-tetrazol-5-yl)pyrimidin-4-amine

Into a sealed tube were added 4-amino-2-chloro-pyrimidine-5-carbonitrile (837 mg, 5.4 mmol), sodium azide (7.1 mmol, 1.3 eq.), triethylamine hydrochloride (7.1 mmol, 1.3 eq.) and 14 mL of toluene. The tube was tightly capped and the reaction was stirred and heated to 100° C. overnight. The mixture was cooled to room temperature, diluted with ethyl acetate, transferred to a separatory funnel and extracted three times with water. The aqueous extractions were combined and acidified to a pH of 4 with concentrated HCl. The precipitate was collected by filtration, washed with acetonitrile, and dried under vacuum to afford 460 mg of the product, which was used without further purification. MS (EI) for $C_5HClN_7$: 198 (M+H).

Step 2: $N^2$-Benzyl-5-(1H-tetrazol-5-yl)pyrimidine-2,4-diamine

In a microwave tube, 2-chloro-5-(1H-tetrazol-5-yl)pyrimidin-4-amine (200 mg, 1.0 mmol) was dissolved into 3 mL of dioxane and DIPEA (1.5 mmol, 1.5 eq.). After the addition of benzylamine (5.0 mmol, 5.0 eq.), the tube was capped and irradiated in a CEM Discover microwave reactor to 120° C. for a total of 60 minutes in three 20 minutes intervals. LC/MS was taken every 20 minutes to follow the disappearance of starting material. After the complete consumption of the starting material, the reaction was cooled to room temperature and a precipitate formed. This solid was collected by filtration, washed several times with water, then with hot EtOAc. It was dried under vacuum to afford 27 mg of desired product. This material was carried forward without further purification. MS (EI) for $C_{12}H_{12}N_8$: 269 (M+H).

Step 3: N-{2-[(Phenylmethyl)amino]-5-(1H-tetrazol-5-yl)pyrimidin-4-yl}thiophene-2-carboxamide To a solution of $N^2$-Benzyl-5-(1H-tetrazol-5-yl)pyrimidine-2,4-diamine (27 mg, 0.1 mmol) in 1 mL of DCE, DIPEA (0.3 mmol, 3.0 eq.) was added followed by thiophene-2-carbonyl chloride (0.15 mmol, 1.5 eq.). The reaction was stirred at room temperature for 2 hours. The crude reaction mixture was concentrated down in vacuo, and the residue redissolved in ethylacetate. This organic solution was extracted several times with water, dried with magnesium sulfate, filtered and concentrated. The residue was purified by reverse phase HPLC to give 4.8 mg of the desired compound. $^1$H-NMR (400 MHz, $d_6$-DMSO): δ 9.07 (t, 1H), 7.81 (dd, 1H), 7.77 (dd, 1H), 7.36-7.29 (m, 4H), 7.28-7.23 (m, 1H), 7.16 (t, 1H), 4.45 (d, 2H). MS (EI) for $C_{17}H_{14}N_8OS$: 379 (M+H).

Example 83

4-Chloro-2-{[(3-chloro-2-thienyl)carbonyl]amino}benzoic acid

The compound was synthesized as outlined in the following synthetic sequence.

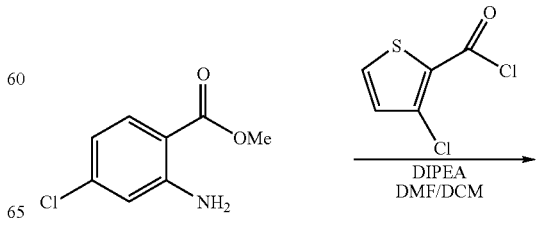

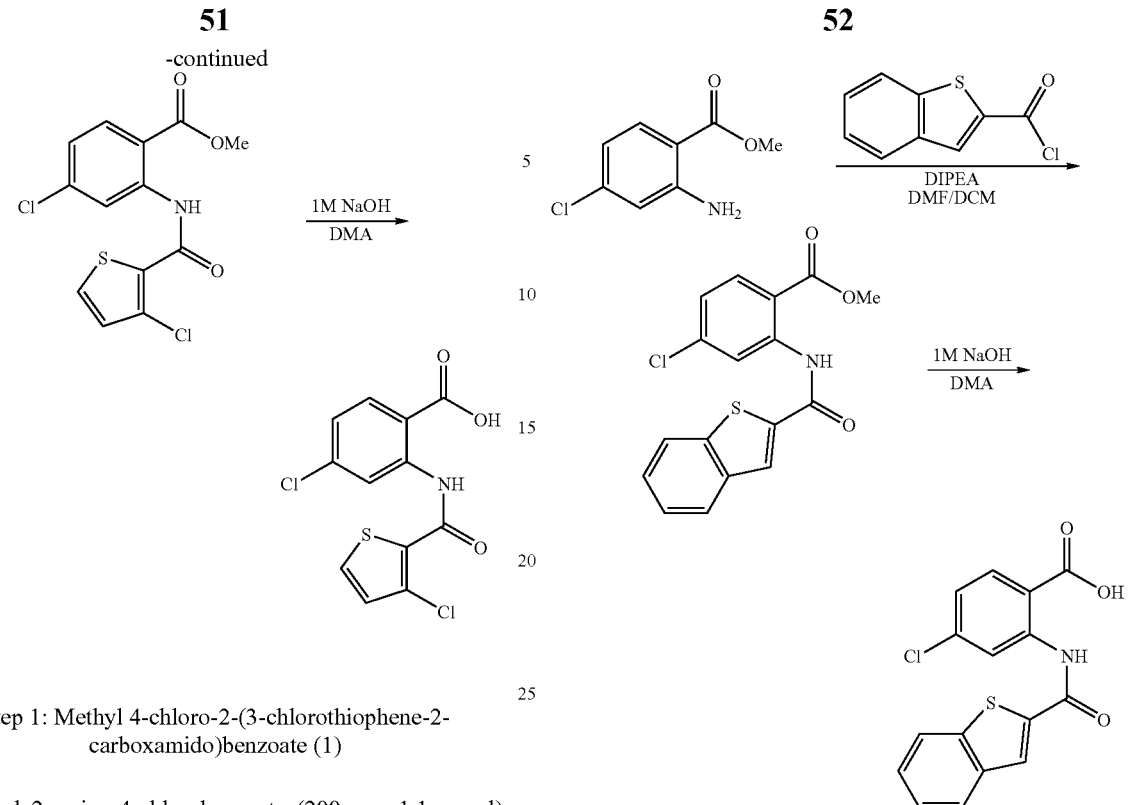

Step 1: Methyl 4-chloro-2-(3-chlorothiophene-2-carboxamido)benzoate (1)

Methyl 2-amino-4-chlorobenzoate (200 mg, 1.1 mmol) and diisopropylethylamine (285 μL, 1.6 mmol) were dissolved in a solution of dichloromethane (4 mL) and dimethylformamide (2 mL). 3-Chlorothiophene-2-carbonyl chloride (235 mg, 1.3 mmol) was added dropwise. The reaction mixture was stirred overnight at room temperature. The solvent was removed under vacuum and the residue was re-dissolved in 25 mL of ethyl acetate. The reaction mixture was washed one time each with 10 mL portions of water, 0.1 M NaOH, and saturated aqueous NaCl. The organic layer was dried with $MgSO_4$ and 90 mg of solid was precipitated by the addition of hexanes. The material was used without further purification. MS (EI) for $C_{13}H_9Cl_2NO_3S$: 330 (M+H).

Step 2: 4-Chloro-2-{[(3-chloro-2-thienyl)carbonyl]amino}benzoic acid

Methyl 4-chloro-2-(3-chlorothiophene-2-carboxamido)benzoate (90 mg, 0.27 mmol) was dissolved in 4 mL of dimethylacetamide. 1 M NaOH (1 mL) was added and the reaction was stirred at room temperature overnight. The product was precipitated by the addition of 1 M HCl to the reaction mixture. The product was filtered and dried under vacuum to give 69 mg of white solid. $^1$H NMR (400 MHz, $d_6$-DMSO): 12.08 (s, 1H), 8.68 (d, 1H), 8.05 (d, 1H), 8.03 (d, 1H), 7.32 (dd, 1H), 7.28 (d, 1H); MS (EI) for $C_{12}H_7Cl_2NO_3S$: 316 (M+H).

Example 84

2-[(1-Benzothien-2-ylcarbonyl)amino]-4-chlorobenzoic acid

The compound was synthesized as outlined in the following synthetic sequence.

Step 1: Methyl 2-(benzothiophene-2-carboxamido)-4-chlorobenzoate

Methyl 2-amino-4-chlorobenzoate (200 mg, 1.1 mmol) and diisopropylethyl amine (1045 μL, 5.9 mmol) were dissolved in a solution of dichloromethane (4 mL) and dimethylformamide (2 μL). Benzothiothiophene-2-carbonyl chloride (1060 mg, 5.4 mmol) was added in one portion. The reaction mixture was stirred overnight at room temperature. The solvent was removed under vacuum and the residue was re-dissolved in 25 mL of ethyl acetate. The reaction mixture was washed one time each with 10 mL portions of water, 0.1 M NaOH, and saturated aqueous NaCl. The organic layer was dried with $MgSO_4$ and concentrated under vacuum. The crude material was used without further purification. MS (EI) for $C_{13}H_9Cl_2NO_3S$: 330 (M+H).

Step 2: 4-Chloro-2-(3-chlorothiophene-2-carboxamido)benzoic acid

Methyl 2-(benzothiophene-2-carboxamido)-4-chlorobenzoate (1 mmol) was dissolved in 4 mL of dimethylacetamide. 1 M NaOH (1 mL) was added and the reaction was stirred at room temperature overnight. The product was precipitated by the addition of 1 M HCl to the reaction mixture. The product was filtered and dried under vacuum to give 20 mg of white solid. $^1$H NMR (400 MHz, $d_6$-DMSO): 12.49 (s, 1H), 8.69 (d, 1H), 8.12-8.07 (m, 4H), 7.57-7.48 (m, 2M), 7.32 (dd, 1H); MS (EI) for $C_{16}H_{10}ClNO_3S$: 332 (M+H).

Example 85

4-Chloro-2-[(cyclopentylcarbonyl)amino]benzoic acid

In a 2 mL vial, methyl 2-amino-4-chlorobenzoate (7.4 mg, 40 μmol) was dissolved into a mixture of 655 μL DCE and 120

µL DMA, followed by addition of DIPEA (600 µmol, 15 eq.). Cyclopentanecarboxylic acid (13.7 mg, 120 µmol, 3 eq.) and POCl$_3$ (18.2 mg, 120 µmol, 3 eq.) were added. The reaction mixture was capped and stirred at room temperature overnight. Another 700 µL of DCE was added to the reaction mixture along with the following resin bound reagents: a resin bound diethylene triamine (PL-DETA, Polymer Labs, 297 µmol, 7.4 eq.) and a hydroxide ion exchange resin (PL-MP Hydroxide, Polymer Labs, 800 µmol, 20 eq.). The vial was recapped and shaken at room temperature overnight. The resin in the reaction mixture was filtered off, rinsed with 300 µL of MeOH and discarded. The combined filtrates were concentrated down in vacuo. The residue was re-dissolved into 1 mL of DMA and 280 µL of 1M aqueous NaOH. The solution was stirred at room temperature overnight. The desired product was isolated directly from this solution via reverse phase C18 preparative HPLC (water/acetonitrile w/0.1% formic acid, 30%-100% eluant gradient) to yield the final product (4.3 mg, 99% purity). MS (EI) for $C_{13}H_{14}ClNO_3$: 268 (M+H).

Example 86

4-Chloro-2-[(pyridin-2-ylcarbonyl)amino]benzoic acid

In a 2 mL vial, methyl 2-amino-4-chlorobenzoate (7.4 mg, 40 µmol) was dissolved into a mixture of 655 µL DCE and 120 µL DMA, followed by addition of DIPEA (600 µmol, 15 eq.). Picolinic acid (14.8 mg, 120 µmol, 3 eq.) and POCl$_3$ (18.2 mg, 120 µmol, 3 eq.) were added. The reaction mixture was capped and stirred at room temperature overnight. Another 700 µL of DCE was added to the reaction mixture along with the following resin bound reagents: a resin bound diethylene triamine (PL-DETA, Polymer Labs, 297 µmol, 7.4 eq.) and a hydroxide ion exchange resin (PL-MP Hydroxide, Polymer Labs, 800 µmol, 20 eq.). The vial was recapped and shaken at room temperature overnight. The resin in the reaction mixture was filtered off, rinsed with 300 µL of MeOH and discarded. The combined filtrates were concentrated down in vacuo. The residue was re-dissolved into 1 mL of DMA and 280 µL of 1M aqueous NaOH. The solution was stirred at room temperature overnight. The desired product was isolated directly from this solution via reverse phase C18 preparative HPLC (water/acetonitrile w/0.1% formic acid, 30%-100% eluant gradient) to yield the final product (3.0 mg, 95% purity). MS (EI) for $C_{13}H_9ClN_2O_3$: 277 (M+H).

Example 87

4-Chloro-2-{[(2,5-dichloro-3-thienyl)carbonyl]amino}benzoic acid

In a 2 mL vial, methyl 2-amino-4-chlorobenzoate (7.4 mg, 40 µmol) was dissolved into a mixture of 655 µL DCE and 120 µL DMA, followed by addition of DIPEA (600 µmol, 15 eq.). 2,5-Dichlorothiophene-3-carboxylic acid (23.6 mg, 120 µmol, 3 eq.) and POCl$_3$ (18.2 mg, 120 µmol, 3 eq.) were added. The reaction mixture was capped and stirred at room temperature overnight. Another 700 µL of DCE was added to the reaction mixture along with the following resin bound reagents: a resin bound diethylene triamine (PL-DETA, Polymer Labs, 297 µmol, 7.4 eq.) and a hydroxide ion exchange resin (PL-MP Hydroxide, Polymer Labs, 800 µmol, 20 eq.). The vial was recapped and shaken at room temperature overnight. The resin in the reaction mixture was filtered off, rinsed with 300 µL of MeOH and discarded. The combined filtrates were concentrated down in vacuo. The residue was re-dissolved into 1 mL of DMA and 280 µL of 1M aqueous NaOH. The solution was stirred at room temperature overnight. The desired product was isolated directly from this solution via reverse phase C18 preparative HPLC (water/acetonitrile w/0.1% formic acid, 30%-100% eluant gradient) to yield the final product (3.2 mg, 98% purity). MS (EI) for $C_{12}H_6Cl_3NO_3S$: 351 (M+H).

Example 88

2-[(1-Benzothien-3-ylcarbonyl)amino]-4-chlorobenzoic acid

In a 2 mL vial, methyl 2-amino-4-chlorobenzoate (7.4 mg, 40 µmol) was dissolved into a mixture of 655 µL DCE and 120 µL DMA, followed by addition of DIPEA (600 µmol, 15 eq.). Benzo[b]thiophene-3-carboxylic acid (21.4 mg, 120 µmol, 3 eq.) and POCl$_3$ (18.2 mg, 120 µmol, 3 eq.) were added. The reaction mixture was capped and stirred at room temperature overnight. Another 700 µL of DCE was added to the reaction mixture along with the following resin bound reagents: a resin bound diethylene triamine (PL-DETA, Polymer Labs, 297 µmol, 7.4 eq.) and a hydroxide ion exchange resin (PL-MP Hydroxide, Polymer Labs, 800 µmol, 20 eq.). The vial was recapped and shaken at room temperature overnight. The resin in the reaction mixture was filtered off, rinsed with 300 µL of MeOH and discarded. The combined filtrates were concentrated down in vacuo. The residue was re-dissolved into 1 mL of DMA and 280 µL of 1M aqueous NaOH. The solution was stirred at room temperature overnight. The desired product was isolated directly from this solution via reverse phase C18 preparative HPLC (water/acetonitrile w/0.1% formic acid, 30%-100% eluant gradient) to yield the final product (2.9 mg, 95% purity). MS (EI) for $C_{16}H_{10}ClNO_3S$: 332 (M+H).

The PIM-1 and/or PIM-3 IC$_{50}$ values for many of the above compounds appear below. The compound numbers in Table 1 do not necessarily correspond to the above example numbers.

TABLE 1

| Cmpnd No. | Name | Structure |
|---|---|---|
| 1 | 3-Chloro-N-(5-chloro-2-(1H-tetrazol-5-yl)phenyl)thiophene-2-carboxamide | 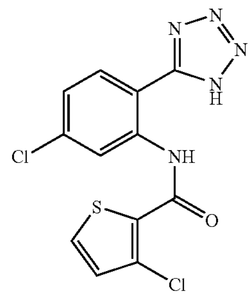 |
| 2 | N-[5-Chloro-2-(1H-tetrazol-5-yl)phenyl]benzamide | 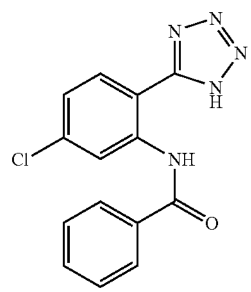 |
| 3 | N-[5-Chloro-2-(1H-tetrazol-5-yl)phenyl]-3-(methyloxy)benzamide | 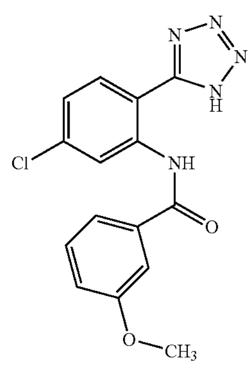 |
| 4 | N-[5-Chloro-2-(1H-tetrazol-5-yl)phenyl]-2,2-dimethylpropanamide | 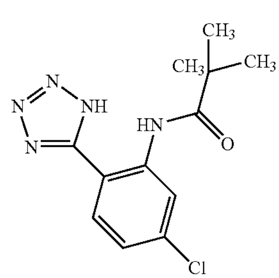 |

TABLE 1-continued

| Cmpnd No. | Name | Structure |
|---|---|---|
| 5 | 4-Methoxy-N-[5-chloro-2-(1H-tetrazol-5-yl)phenyl]benzamide | 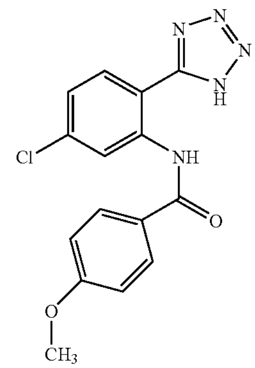 |
| 6 | N-[5-Chloro-2-(1H-tetrazol-5-yl)phenyl]cyclohexanecarboxamide | 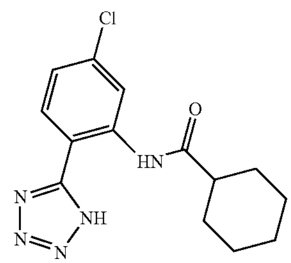 |
| 7 | N-[5-Chloro-2-(1H-tetrazol-5-yl)phenyl]-2-methylpropanamide | 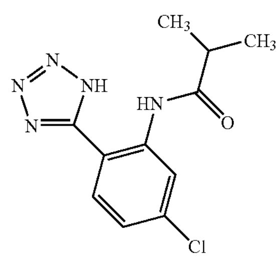 |
| 8 | N-[5-Chloro-2-(1H-tetrazol-5-yl)phenyl]-2-methylbutanamide | 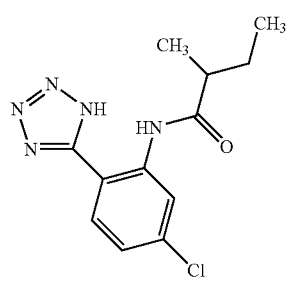 |
| 9 | N-[5-Chloro-2-(1H-tetrazol-5-yl)phenyl]-4-methyl-1,2,3-thiadiazole-5-carboxamide | 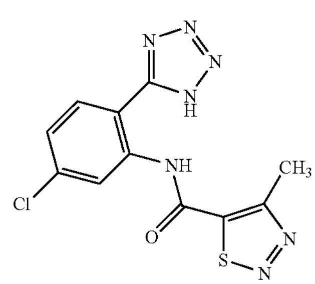 |

TABLE 1-continued
| Cmpnd No. | Name | Structure |
|---|---|---|
| 10 | 4-Chloro-N-[5-chloro-2-(1H-tetrazol-5-yl)phenyl]benzamide | 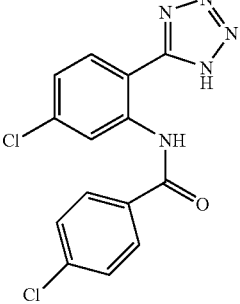 |
| 11 | N-[5-Chloro-2-(1H-tetrazol-5-yl)phenyl]-2-cyclopentylacetamide | 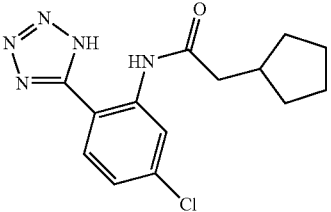 |
| 12 | (4R)-N-[5-Chloro-2-(1H-tetrazol-5-yl)phenyl]-4,7,7-trimethyl-3-oxo-2-oxabicyclo[2.2.1]heptane-1-carboxamide | 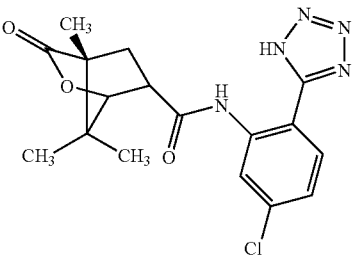 |
| 13 | N-[5-Chloro-2-(1H-tetrazol-5-yl)phenyl]-3-methylbutanamide | 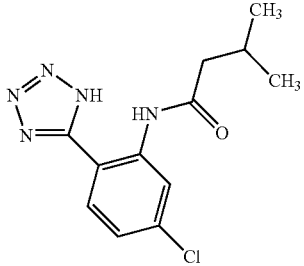 |
| 14 | 2-(2-Bromophenyl)-N-[5-chloro-2-(1H-tetrazol-5-yl)phenyl]acetamide | 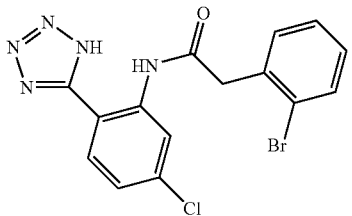 |

TABLE 1-continued

| Cmpnd No. | Name | Structure |
|---|---|---|
| 15 | N-[5-Chloro-2-(1H-tetrazol-5-yl)phenyl]-5-methylisoxazole-3-carboxamide | 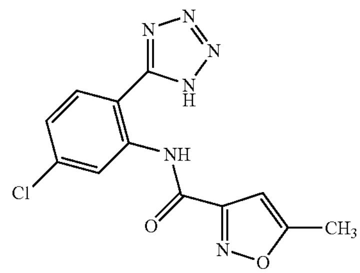 |
| 16 | N-[5-Chloro-2-(1H-tetrazol-5-yl)phenyl]-2-(2-thienyl)acetamide | 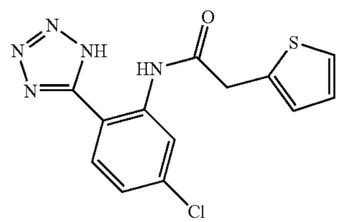 |
| 17 | N-[5-Chloro-2-(1H-tetrazol-5-yl)phenyl]-2-methylpentanamide | 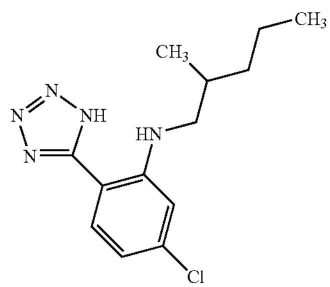 |
| 18 | 3-Chloro-N-[5-chloro-2-(1H-tetrazol-5-yl)phenyl]-1-benzothiophene-2-carboxamide | 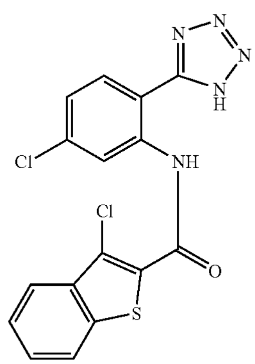 |
| 19 | 3-Chloro-N-[5-chloro-2-(1H-tetrazol-5-yl)phenyl]benzamide | 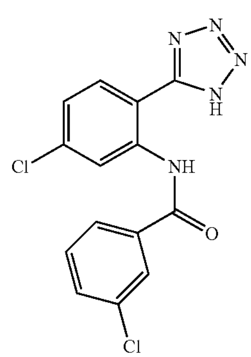 |

TABLE 1-continued
| Cmpnd No. | Name | Structure |
|---|---|---|
| 20 | N-[5-Chloro-2-(1H-tetrazol-5-yl)phenyl]pentanamide | 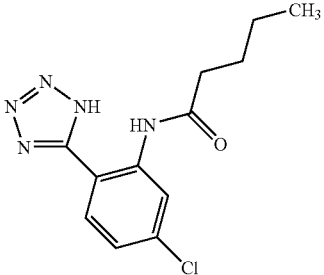 |
| 21 | N-[5-Chloro-2-(1H-tetrazol-5-yl)phenyl]isoxazole-5-carboxamide | 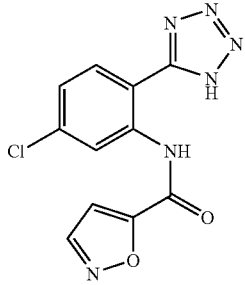 |
| 22 | (3s,5s,7s)-N-[5-Chloro-2-(1H-tetrazol-5-yl)phenyl]tricyclo[3.3.1.1~3,7~]decane-1-carboxamide | [Abs] 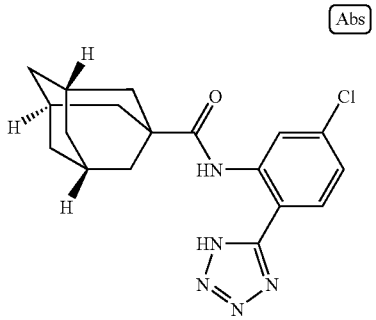 |
| 23 | N-[5-Methyl-2-(1H-tetrazol-5-yl)phenyl]thiophene-2-carboxamide | 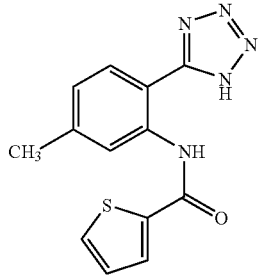 |
| 24 | N-[5-Chloro-2-(1H-tetrazol-5-yl)phenyl]-2-ethylbutanamide | 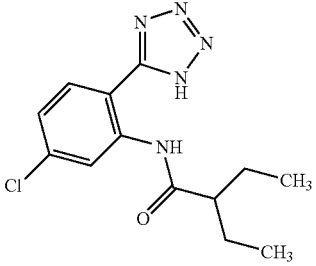 |

TABLE 1-continued
| Cmpnd No. | Name | Structure |
|---|---|---|
| 25 | N-[5-Chloro-2-(1H-tetrazol-5-yl)phenyl]butanamide | 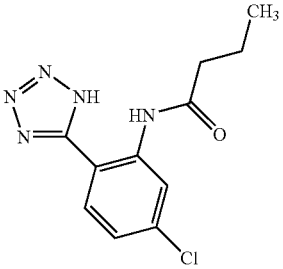 |
| 26 | N-[5-Chloro-2-(1H-tetrazol-5-yl)phenyl]cyclopentanecarboxamide | 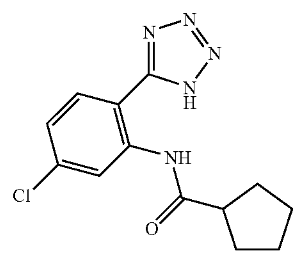 |
| 27 | N-[5-Chloro-2-(1H-tetrazol-5-yl)phenyl]-3,5-dimethylisoxazole-4-carboxamide | 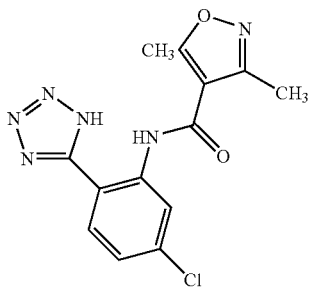 |
| 28 | N-[5-Chloro-2-(1H-tetrazol-5-yl)phenyl]propanamide | 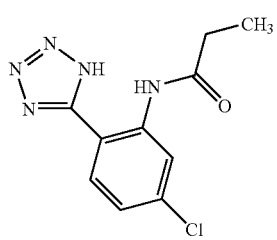 |
| 29 | N-[5-Chloro-2-(1H-tetrazol-5-yl)phenyl]-2-phenylacetamide | 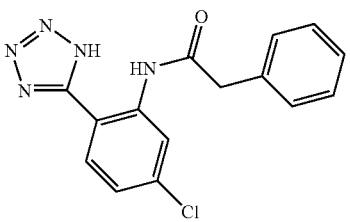 |

TABLE 1-continued

| Cmpnd No. | Name | Structure |
|---|---|---|
| 30 | N-[5-Chloro-2-(1H-tetrazol-5-yl)phenyl]-1-benzothiophene-2-carboxamide | 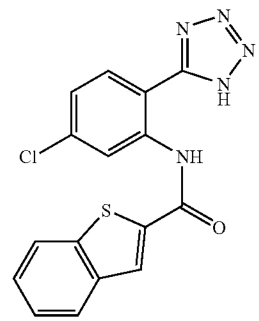 |
| 31 | N-[5-Chloro-2-(1H-tetrazol-5-yl)phenyl]-4-methylpentanamide | 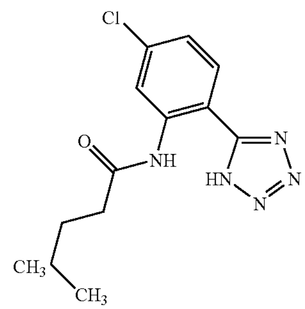 |
| 32 | N-[5-Chloro-2-(1H-tetrazol-5-yl)phenyl]-2-(methyloxy)acetamide | 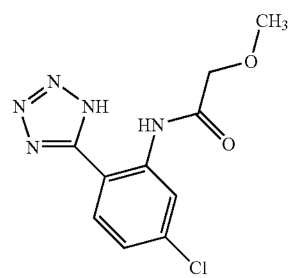 |
| 33 | 1-Acetyl-N-[5-chloro-2-(1H-tetrazol-5-yl)phenyl]piperidine-4-carboxamide | 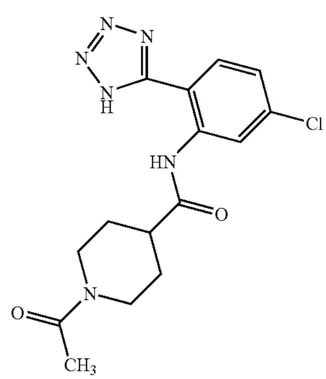 |
| 34 | N-[4-Bromo-2-(1H-tetrazol-5-yl)phenyl]thiophene-2-carboxamide | 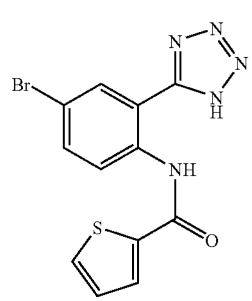 |

TABLE 1-continued

| Cmpnd No. | Name | Structure |
|---|---|---|
| 35 | N-[5-Chloro-2-(1H-tetrazol-5-yl)phenyl]-2-phenylbutanamide | 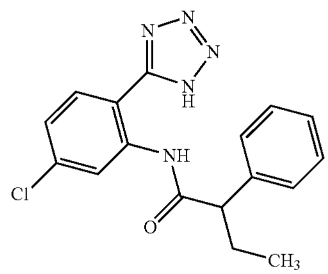 |
| 36 | N-[5-Chloro-2-(1H-tetrazol-5-yl)phenyl]-N~2~,N~2~-dimethylglycinamide | 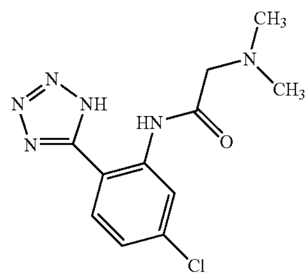 |
| 37 | Ethyl 3-{[5-chloro-2-(1H-tetrazol-5-yl)phenyl]amino}-3-oxopropanoate | 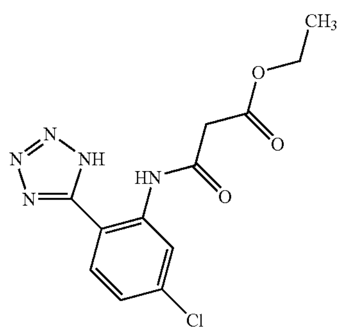 |
| 38 | N-[5-Chloro-2-(1H-tetrazol-5-yl)phenyl]-5-methyl-3-phenylisoxazole-4-carboxamide | 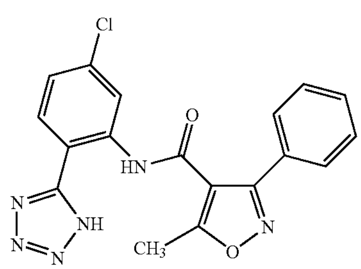 |
| 39 | 4-Chloro-2-{[(3-chloro-2-thienyl)carbonyl]amino}benzoic acid | 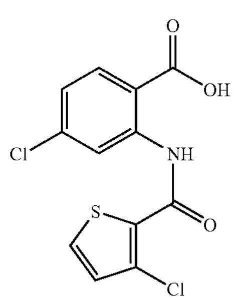 |

TABLE 1-continued

| Cmpnd No. | Name | Structure |
|---|---|---|
| 40 | 2-[(1-Benzothien-2-ylcarbonyl)amino]-4-chlorobenzoic acid | 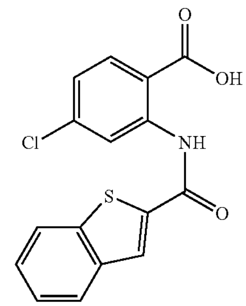 |
| 41 | 4-Chloro-2-[(cyclopentylcarbonyl)amino]benzoic acid | 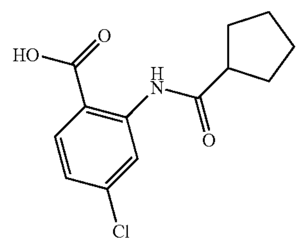 |
| 42 | 4-Chloro-2-[(pyridin-2-ylcarbonyl)amino]benzoic acid | 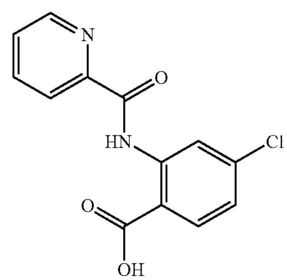 |
| 43 | 2-[(1-Benzothien-3-ylcarbonyl)amino]-4-chlorobenzoic acid | 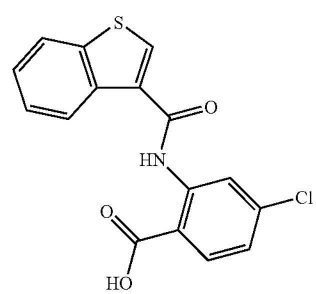 |
| 44 | 4-Chloro-2-{[(2,5-dimethylfuran-3-yl)carbonyl]amino}benzoic acid | 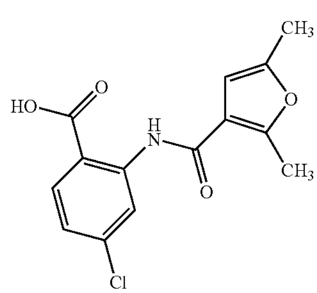 |

TABLE 1-continued

| Cmpnd No. | Name | Structure |
|---|---|---|
| 45 | 4-Chloro-2-[({4-[4-(methyloxy)phenyl]-2-thienyl}carbonyl)amino]benzoic acid | 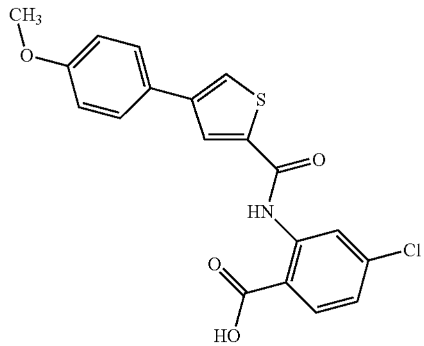 |
| 46 | N-[5-Chloro-2-(1H-tetrazol-5-yl)phenyl]-2-ethylhexanamide | 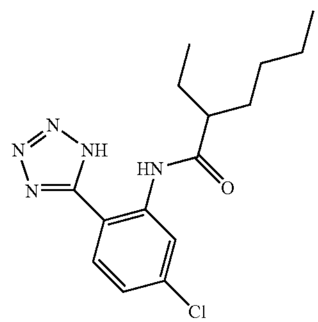 |
| 47 | N-[5-Chloro-2-(1H-tetrazol-5-yl)phenyl]-2-(phenyloxy)acetamide | 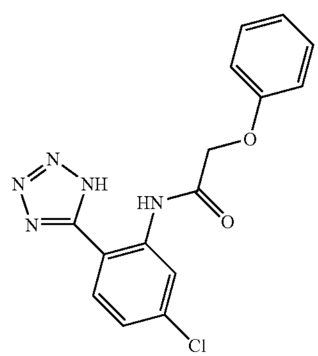 |
| 48 | Methyl 4-{[5-chloro-2-(1H-tetrazol-5-yl)phenyl]amino}-4-oxobutanoate | 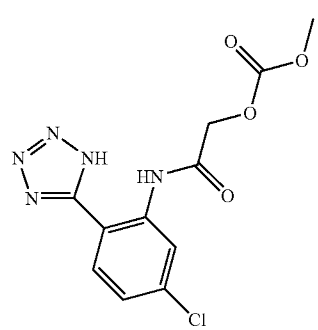 |

TABLE 1-continued

| Cmpnd No. | Name | Structure |
|---|---|---|
| 49 | (1R,2R)-N-[5-Chloro-2-(1H-tetrazol-5-yl)phenyl]-2-phenylcyclopropanecarboxamide | 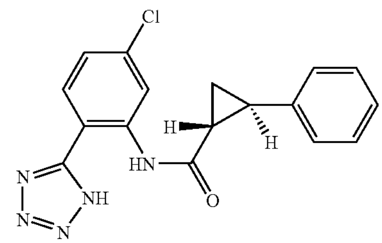 |
| 50 | N-[5-Chloro-2-(1H-tetrazol-5-yl)phenyl]-2-[3-(methyloxy)phenyl]acetamide | 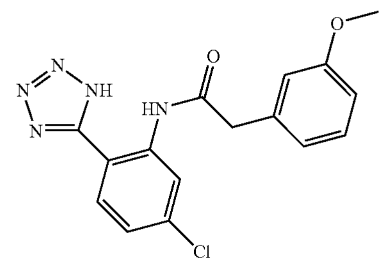 |
| 51 | N-[5-Chloro-2-(1H-tetrazol-5-yl)phenyl]-2,2-diphenylacetamide | 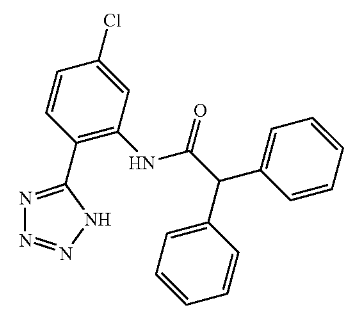 |
| 52 | 3-(2-Chlorophenyl)-N-[5-chloro-2-(1H-tetrazol-5-yl)phenyl]-5-methylisoxazole-4-carboxamide | 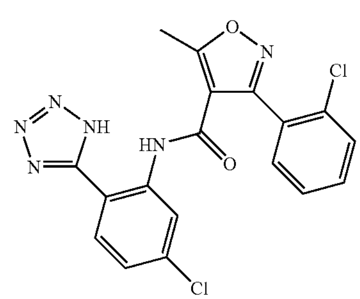 |
| 53 | 2-Chloro-N-[5-chloro-2-(1H-tetrazol-5-yl)phenyl]pyridine-3-carboxamide | 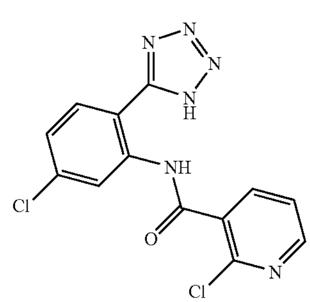 |

TABLE 1-continued

| Cmpnd No. | Name | Structure |
|---|---|---|
| 54 | N-[5-Chloro-2-(1H-tetrazol-5-yl)phenyl]-2-(methylthio)pyridine-3-carboxamide | 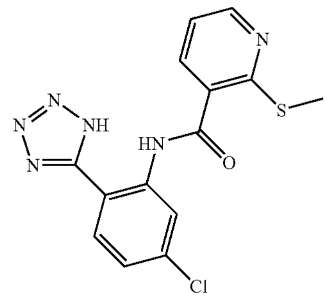 |
| 55 | 3-(2-Chloro-6-fluorophenyl)-N-[5-chloro-2-(1H-tetrazol-5-yl)phenyl]-5-methylisoxazole-4-carboxamide | 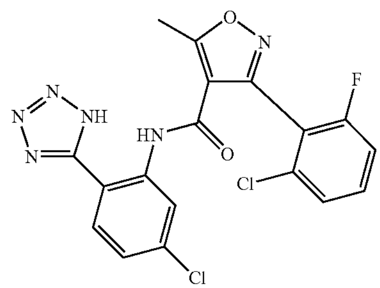 |
| 56 | 3-Chloro-N-[5-chloro-2-(1H-tetrazol-5-yl)phenyl]-4-(methylsulfonyl)thiophene-2-carboxamide | 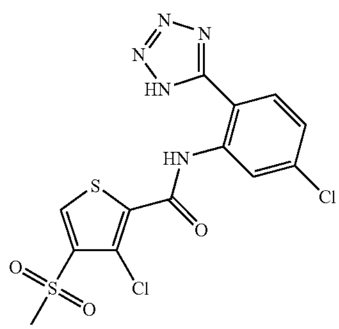 |
| 57 | N-[5-Chloro-2-(1H-tetrazol-5-yl)phenyl]-2,5-dimethylfuran-3-carboxamide | 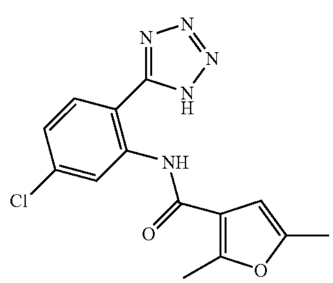 |
| 58 | N-[5-Chloro-2-(1H-tetrazol-5-yl)phenyl]pent-4-enamide | 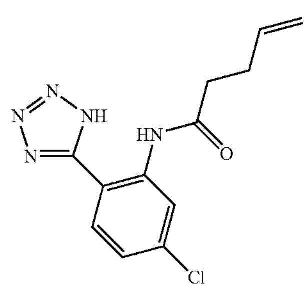 |

TABLE 1-continued

| Cmpnd No. | Name | Structure |
|---|---|---|
| 59 | N-[5-Chloro-2-(1H-tetrazol-5-yl)phenyl]-3,5-bis(trifluoromethyl)benzamide | 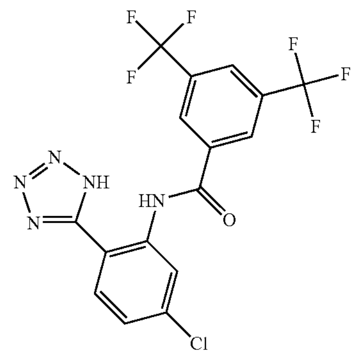 |
| 60 | N-[5-Chloro-2-(1H-tetrazol-5-yl)phenyl]-2-fluorobenzamide | 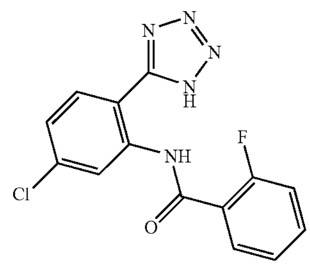 |
| 61 | N-[5-Chloro-2-(1H-tetrazol-5-yl)phenyl]-2,4-difluorobenzamide | 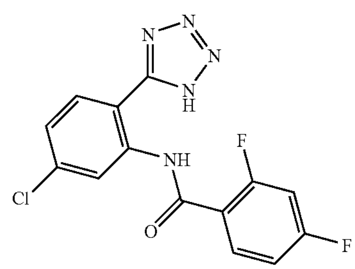 |
| 62 | N-[5-Chloro-2-(1H-tetrazol-5-yl)phenyl]-2,6-difluorobenzamide | 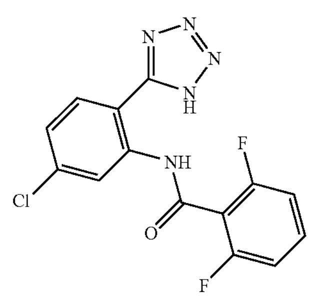 |
| 63 | 2,4-Dichloro-N-[5-chloro-2-(1H-tetrazol-5-yl)phenyl]benzamide | 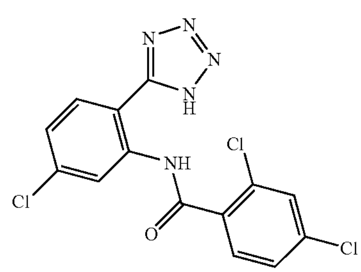 |

TABLE 1-continued

| Cmpnd No. | Name | Structure |
|---|---|---|
| 64 | N-[5-Chloro-2-(1H-tetrazol-5-yl)phenyl]-2-(trifluoromethyl)benzamide | 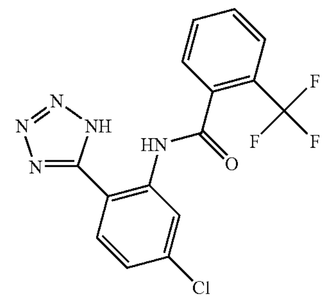 |
| 65 | N-[5-Chloro-2-(1H-tetrazol-5-yl)phenyl]-2-methylbenzamide | 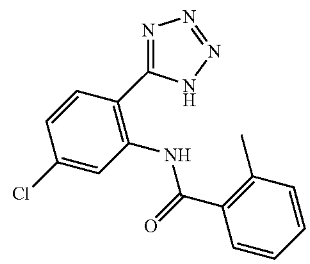 |
| 66 | 3-Bromo-N-[5-chloro-2-(1H-tetrazol-5-yl)phenyl]benzamide | 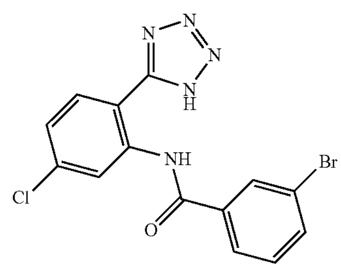 |
| 67 | N-[5-Chloro-2-(1H-tetrazol-5-yl)phenyl]-3-fluorobenzamide | 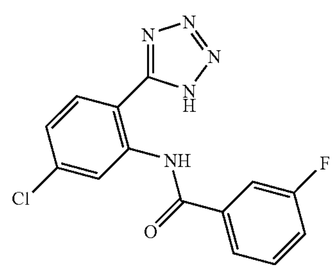 |
| 68 | 3,4-Dichloro-N-[5-chloro-2-(1H-tetrazol-5-yl)phenyl]benzamide | 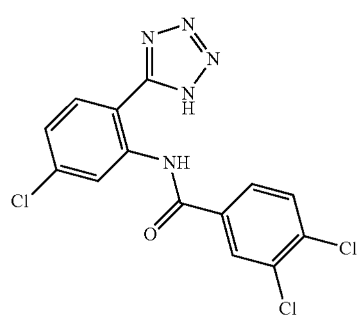 |

TABLE 1-continued

| Cmpnd No. | Name | Structure |
|---|---|---|
| 69 | N-[5-Chloro-2-(1H-tetrazol-5-yl)phenyl]-3-(trifluoromethyl)benzamide | 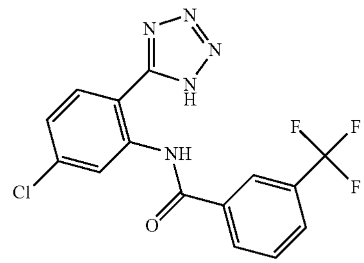 |
| 70 | N-[5-Chloro-2-(1H-tetrazol-5-yl)phenyl]-3-methylbenzamide | 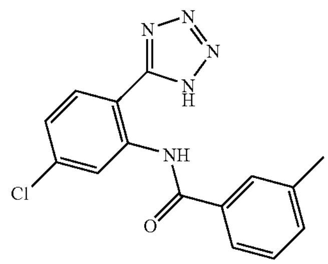 |
| 71 | N-[5-Chloro-2-(1H-tetrazol-5-yl)phenyl]-4-fluorobenzamide | 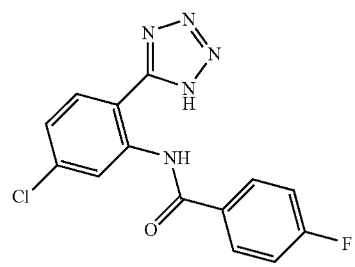 |
| 72 | N-[5-Chloro-2-(1H-tetrazol-5-yl)phenyl]cyclopropanecarboxamide | 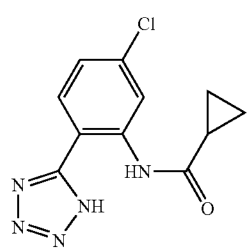 |
| 73 | 5-Chloro-N-[5-chloro-2-(1H-tetrazol-5-yl)phenyl]-1-methyl-1H-pyrazole-4-carboxamide | 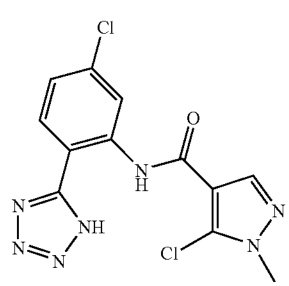 |

TABLE 1-continued

| Cmpnd No. | Name | Structure |
|---|---|---|
| 74 | N-[5-Chloro-2-(1H-tetrazol-5-yl)phenyl]-3-phenylpropanamide | 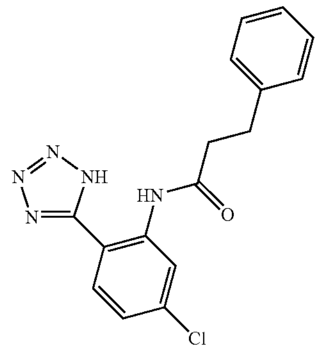 |
| 75 | 2-[(4-Chlorophenyl)oxy]-N-[5-chloro-2-(1H-tetrazol-5-yl)phenyl]acetamide | 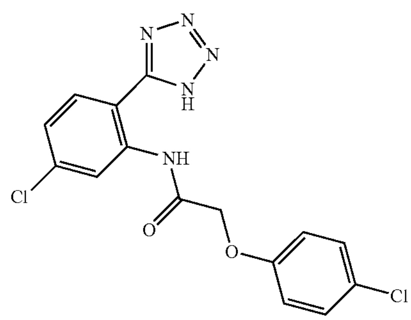 |
| 76 | 2-[(3-Chlorophenyl)oxyl-N-[5-chloro-2-(1H-tetrazol-5-yl)phenyl]acetamide | 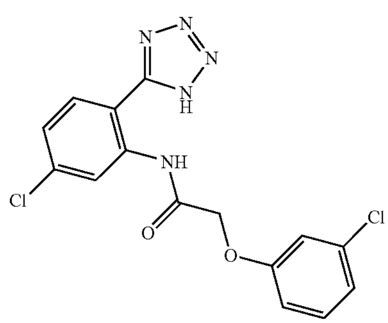 |
| 77 | N-[5-Chloro-2-(1H-tetrazol-5-yl)phenyl]-2-{[3-(methyloxy)phenyl]oxy}acetamide | 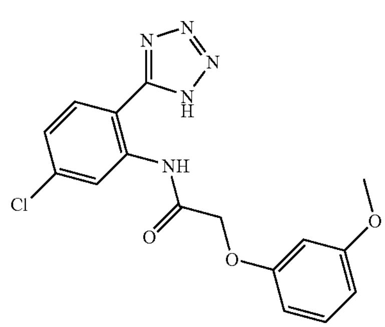 |

TABLE 1-continued

| Cmpnd No. | Name | Structure |
|---|---|---|
| 78 | N-[5-Chloro-2-(1H-tetrazol-5-yl)phenyl]-3-(phenyloxy)propanamide | 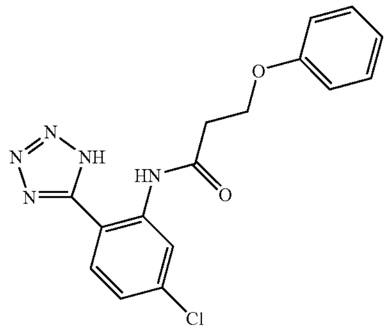 |
| 79 | N-[5-Chloro-2-(1H-tetrazol-5-yl)phenyl]-3-[(4-fluorophenyl)oxy]propanamide | 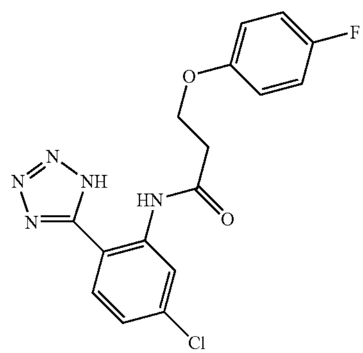 |
| 80 | N-[5-Chloro-2-(1H-tetrazol-5-yl)phenyl]cyclobutanecarboxamide | 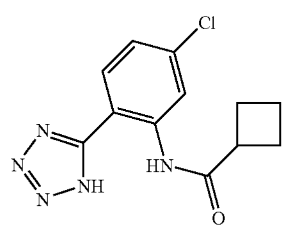 |
| 81 | N-[5-Chloro-2-(1H-tetrazol-5-yl)phenyl]-2-{[2-(4-methylpiperazin-1-yl)phenyl]oxy}acetamide | 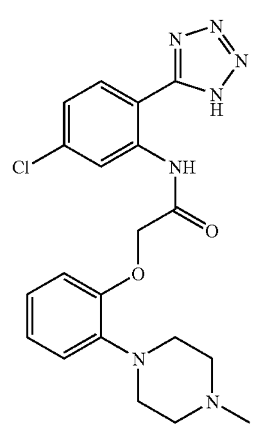 |

TABLE 1-continued

| Cmpnd No. | Name | Structure |
|---|---|---|
| 82 | 4-Chloro-2-{[(2,5-dichloro-3-thienyl)carbonyl]amino}benzoic acid | 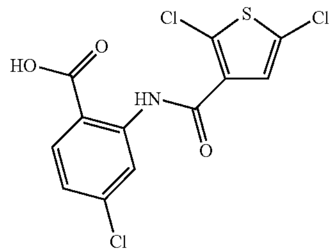 |

All of the compounds in Table 1 were tested for PIM-1 activity and had an $IC_{50}$ value of <2000 nM. The compounds in Table 1 that were tested for PIM-3 activity had $IC_{50}$ values of <2000 nM. Preferred compounds in Table 1 had PIM-1 activity<1000 nM. More preferred compounds had both PIM-1 and PIM-3 $IC_{50}$ values<1000 nM.

TABLE 2

| Cmpnd No. | Name | Structure |
|---|---|---|
| 83 | N-[3-Chloro-2-(1H-tetrazol-5-yl)phenyl]thiophene-2-carboxamide | 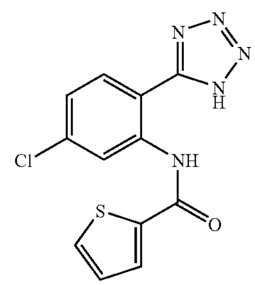 |
| 84 | N-[2-Chloro-6-(1H-tetrazol-5-yl)phenyl]thiophene-2-carboxamide | 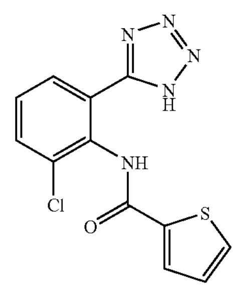 |
| 85 | N-[5-Chloro-2-(1H-tetrazol-5-yl)phenyl]-3-methyl-1-benzofuran-2-carboxamide | 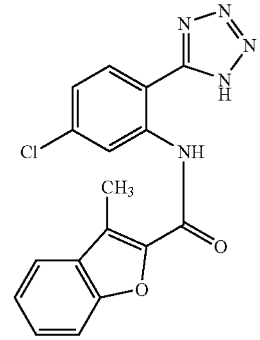 |

TABLE 2-continued

| Cmpnd No. | Name | Structure |
|---|---|---|
| 86 | N-{2-[(Phenylmethyl)amino]-5-(1H-tetrazol-5-yl)pyrimidin-4-yl}thiophene-2-carboxamide | 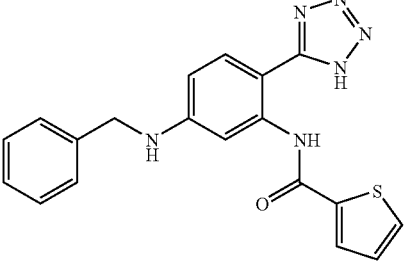 |
| 87 | N-[6-(1H-Tetrazol-5-yl)-1H-benzimidazol-5-yl]thiophene-2-carboxamide | 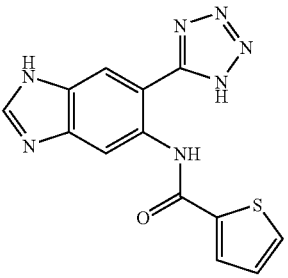 |

All of the compounds in Table 2 were tested for PIM-1 activity and had an IC$_{50}$ value of > or =2000 nM.

PIM Assay Protocol

PIM kinase activity was measured by monitoring peptide substrate dependent hydrolysis of ATP via quantitation of remaining ATP with luciferase based chemiluminescence. For compound evaluation, 0.5 ul compound dissolved in DMSO was added to 10 ul of PIM-1 and/or PIM-3 dissolved in assay buffer (20 mM HEPES pH 7.5, 10 mM MgCl$_2$, 0.03% Triton and 1 mM DTT). After preincubation for 30 minutes at room temperature the reaction was initiated by addition of 10 ul of ATP and substrate peptide AKRRRLSA in assay buffer. Final enzyme, ATP, and peptide concentrations were 1-2 nM, 500 nM, and 10 μM, respectively. After incubation for 120 min at room temperature reaction progress was quantitated by addition of 10 ul Kinase-Glo (Promega) and measurement of chemiluminescence in a Victor reader (Perkin Elmer). A reaction in which compound was omitted was used to determine maximum reaction progress. Omission of compound and enzyme from the reaction was used to determine zero reaction progress.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A compound according to formula I

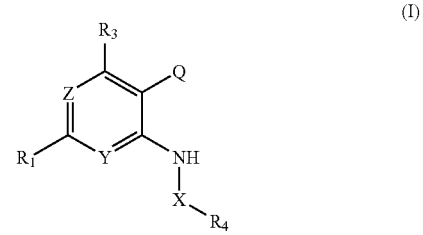

or pharmaceutically acceptable salts thereof, wherein

Q is tetrazolyl;

X is —C(O)—;

R$_1$ is a halogen;

R$_2$ and R$_5$ are independently H or halogen;

R$_3$ is H, chloro, bromo, methyl, NR$_6$R$_7$, or methoxy;

R$_4$ is C$_1$-C$_7$ alkyl, which is optionally substituted with C$_2$-C$_4$ alkenyl, C$_1$-C$_4$ alkoxy, NR$_6$R$_7$, —C$_0$-C$_6$ alkylC(O)OR$_6$, —O-phenyl where the phenyl is optionally substituted with 1, 2, or 3 groups that are independently, halogen, C$_1$-C$_4$ alkyl, C$_1$-C$_4$ alkoxy, hydroxyl, 4-methylpiperazin-1-yl, CF$_3$, or OCF$_3$.

R$_6$ and R$_7$ at each occurrence are independently H, C$_1$-C$_4$ alkyl, C$_2$-C$_4$ alkanoyl, or phenylC$_1$-C$_4$ alkyl;

Y is CR$_5$; and

Z is CR$_2$.

2. A compound according to formula I

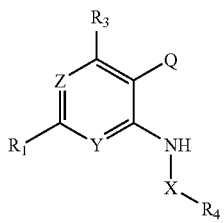

or pharmaceutically acceptable salts thereof, wherein
Q is tetrazolyl;
X is —C(O)—;
$R_1$ is a halogen;
$R_2$ and $R_5$ are independently H or halogen;
$R_3$ is H, chloro, bromo, methyl, $NR_6R_7$, or methoxy;
$R_4$ is heteroaryl or heteroaryl $C_1$-$C_6$ alkyl, each of which is optionally substituted with one or more groups, where each group is independently $C_1$-$C_6$ alkyl, $C_1$-$C_6$ alkoxy, halogen, —$SO_2$—($C_1$-$C_4$ alkyl), —S—($C_1$-$C_4$ alkyl), $C_1$-$C_6$ haloalkyl, $C_1$-$C_6$ haloalkoxy, $C_1$-$C_6$ alkoxy $C_1$-$C_6$ alkyl, $NR_6R_7$, $C_2$-$C_6$ alkanoyl, aryl, or $C_1$-$C_6$ alkyl substituted with $C_1$-$C_6$ alkoxycarbonyl, where the aryl is selected from phenyl and naphthyl, and where the aryl is optionally substituted with one or more groups, where each group is independently halogen, $C_1$-$C_6$ haloalkyl, $C_1$-$C_6$ haloalkoxy, $C_1$-$C_6$ alkyl, $C_1$-$C_6$ alkoxy, or hydroxy;
$R_6$ and $R_7$ at each occurrence are independently H, $C_1$-$C_4$ alkyl, $C_2$-$C_4$ alkanoyl, or phenyl$C_1$-$C_4$ alkyl;
Y is $CR_5$; and
Z is $CR_2$.

3. A compound according to claim 2, wherein
$R_4$ is heteroaryl or heteroaryl $C_1$-$C_6$ alkyl, where the heteroaryl group is thienyl, thiadiazolyl, oxazolyl, benzothienyl, isoxazolyl, benzofuranyl, pyridyl, pyrazolyl, or furanyl, each of which is optionally substituted with one or more groups, where each group is independently halogen, $C_1$-$C_4$ alkyl, —$SO_2$—($C_1$-$C_4$ alkyl), —S—($C_1$-$C_4$ alkyl), $C_1$-$C_4$ alkoxy, or aryl, where the aryl is phenyl optionally substituted with one or more groups, where each group is independently halogen, $C_1$-$C_4$ haloalkyl, $C_1$-$C_4$ haloalkoxy, $C_1$-$C_4$ alkyl, $C_1$-$C_4$ alkoxy, or hydroxy.

4. A compound according formula I

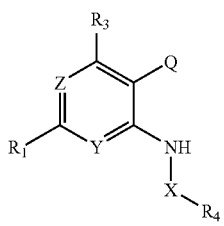

or pharmaceutically acceptable salts thereof, wherein
Q is tetrazolyl;
X is —C(O)—;
$R_1$ is a halogen;
$R_2$ and $R_5$ are independently H or halogen;
$R_3$ is H, chloro, bromo, methyl, $NR_6R_7$, or methoxy;

$R_4$ is heterocycloalkyl or heterocycloalkyl $C_1$-$C_6$ alkyl, each of which is optionally substituted with one or more groups, where each group is independently $C_1$-$C_6$ alkyl, $C_1$-$C_6$ alkoxy, halogen, $C_1$-$C_6$ haloalkyl, $C_1$-$C_6$ haloalkoxy, $C_1$-$C_6$ alkoxy $C_1$-$C_6$ alkyl, $NR_6R_7$, $C_2$-$C_6$ alkanoyl, aryl, or $C_1$-$C_6$ alkyl substituted with $C_1$-$C_6$ alkoxycarbonyl, where the aryl is selected from phenyl and naphthyl, and where the aryl is optionally substituted with one or more groups, where each group is that are independently halogen, $C_1$-$C_6$ alkyl, $C_1$-$C_6$ alkoxy, or hydroxy;
$R_6$ and $R_7$ at each occurrence are independently H, $C_1$-$C_4$ alkyl, $C_2$-$C_4$ alkanoyl, or phenyl$C_1$-$C_4$ alkyl;
Y is $CR_5$; and
Z is $CR_2$.

5. A compound according to claim 4, wherein
$R_4$ is heterocycloalkyl or heterocycloalkyl $C_1$-$C_6$ alkyl, where the heterocycloalkyl group is 3-oxo-2-oxabicyclo[2.2.1]heptanyl, piperidinyl, or tetrahydrofuranyl, each of which is optionally substituted with one or more groups, where each group is independently $C_1$-$C_6$ alkyl, $C_1$-$C_6$ alkoxy, halogen, $C_1$-$C_4$ haloalkyl, $C_1$-$C_4$ haloalkoxy, $C_1$-$C_6$ alkoxy $C_1$-$C_6$ alkyl, $NR_6R_7$, $C_2$-$C_6$ alkanoyl, aryl, or $C_1$-$C_6$ alkyl substituted with $C_1$-$C_6$ alkoxycarbonyl, the aryl is selected from phenyl and naphthyl, where the aryl is optionally substituted with one or more groups, where each group is independently halogen, $C_1$-$C_6$ alkyl, $C_1$-$C_6$ alkoxy, or hydroxy.

6. A compound according to claim 5, wherein
$R_4$ is heterocycloalkyl or heterocycloalkyl $C_1$-$C_6$ alkyl, where the heterocycloalkyl group is 3-oxo-2-oxabicyclo[2.2.1]heptane substituted with one or more methyl groups, piperidinyl substituted with $C_2$-$C_4$ alkanoyl, or tetrahydrofuranyl.

7. A compound selected from one of:
3-Chloro-N-(5-chloro-2-(1H-tetrazol-5-yl)phenyl)thiophene-2-carboxamide;
N-[5-Chloro-2-(1H-tetrazol-5-yl)phenyl]-2,2-dimethylpropanamide;
N-[5-Chloro-2-(1H-tetrazol-5-yl)phenyl]cyclohexanecarboxamide;
N-[5-Chloro-2-(1H-tetrazol-5-yl)phenyl]-2-methylpropanamide;
N-[5-Chloro-2-(1H-tetrazol-5-yl)phenyl]-2-methylbutanamide;
N-[5-Chloro-2-(1H-tetrazol-5-yl)phenyl]-4-methyl-1,2,3-thiadiazole-5-carboxamide;
N-[5-Chloro-2-(1H-tetrazol-5-yl)phenyl]-2-cyclopentylacetamide;
(4R)—N-[5-Chloro-2-(1H-tetrazol-5-yl)phenyl]-4,7,7-trimethyl-3-oxo-2-oxabicyclo[2.2.1]heptane-1-carboxamide;
N-[5-Chloro-2-(1H-tetrazol-5-yl)phenyl]-3-methylbutanamide;
N-[5-Chloro-2-(1H-tetrazol-5-yl)phenyl]-5-methylisoxazole-3-carboxamide;
N-[5-Chloro-2-(1H-tetrazol-5-yl)phenyl]-2-(2-thienyl)acetamide;
N-[5-Chloro-2-(1H-tetrazol-5-yl)phenyl]-2-methylpentanamide;
3-Chloro-N-[5-chloro-2-(1H-tetrazol-5-yl)phenyl]-1-benzothiophene-2-carboxamide;
N-[5-Chloro-2-(1H-tetrazol-5-yl)phenyl]pentanamide;
N-[5-Chloro-2-(1H-tetrazol-5-yl)phenyl]isoxazole-5-carboxamide;
(3s,5s,7s)-N-[5-Chloro-2-(1H-tetrazol-5-yl)phenyl]tricyclo[3.3.1.1~3,7~]decane-1-carboxamide;

N-[5-Chloro-2-(1H-tetrazol-5-yl)phenyl]-2-ethylbutanamide;
N-[5-Chloro-2-(1H-tetrazol-5-yl)phenyl]butanamide;
N-[5-Chloro-2-(1H-tetrazol-5-yl)phenyl]cyclopentanecarboxamide;
N-[5-Chloro-2-(1H-tetrazol-5-yl)phenyl]-3,5-dimethylisoxazole-4-carboxamide;
N-[5-Chloro-2-(1H-tetrazol-5-yl)phenyl]propanamide;
N-[5-Chloro-2-(1H-tetrazol-5-yl)phenyl]-1-benzothiophene-2-carboxamide;
N-[5-Chloro-2-(1H-tetrazol-5-yl)phenyl]-4-methylpentanamide;
N-[5-Chloro-2-(1H-tetrazol-5-yl)phenyl]-2-(methyloxy)acetamide;
N-[5-Chloro-2-(1H-tetrazol-5-yl)phenyl]-N~2~,N~2~-dimethylglycinamide;
Ethyl 3-{[5-chloro-2-(1H-tetrazol-5-yl)phenyl]amino}-3-oxopropanoate;
N-[5-Chloro-2-(1H-tetrazol-5-yl)phenyl]-5-methyl-3-phenylisoxazole-4-carboxamide;
N-[3-Chloro-2-(1H-tetrazol-5-yl)phenyl]thiophene-2-carboxamide;
N-[2-Chloro-6-(1H-tetrazol-5-yl)phenyl]thiophene-2-carboxamide;
N-[5-Chloro-2-(1H-tetrazol-5-yl)phenyl]-3-methyl-1-benzofuran-2-carboxamide;
N-{2-[(Phenylmethyl)amino]-5-(1H-tetrazol-5-yl)pyrimidin-4-yl}thiophene-2-carboxamide;
N-[6-(1H-Tetrazol-5-yl)-1H-benzimidazol-5-yl]thiophene-2-carboxamide;
N-[5-Chloro-2-(1H-tetrazol-5-yl)phenyl]-2-ethylhexanamide;
N-[5-Chloro-2-(1H-tetrazol-5-yl)phenyl]-2-(phenyloxy)acetamide;
Methyl 4-{[5-chloro-2-(1H-tetrazol-5-yl)phenyl]amino}-4-oxobutanoate;
(1R,2R)—N-[5-Chloro-2-(1H-tetrazol-5-yl)phenyl]-2-phenylcyclopropanecarboxamide;
3-(2-Chlorophenyl)-N-[5-chloro-2-(1H-tetrazol-5-yl)phenyl]-5-methylisoxazole-4-carboxamide;
2-Chloro-N-[5-chloro-2-(1H-tetrazol-5-yl)phenyl]pyridine-3-carboxamide;
N-[5-Chloro-2-(1H-tetrazol-5-yl)phenyl]-2-(methylthio)pyridine-3-carboxamide;
3-(2-Chloro-6-fluorophenyl)-N-[5-chloro-2-(1H-tetrazol-5-yl)phenyl]-5-methylisoxazole-4-carboxamide;
3-Chloro-N-[5-chloro-2-(1H-tetrazol-5-yl)phenyl]-4-(methylsulfonyl)thiophene-2-carboxamide;
N-[5-Chloro-2-(1H-tetrazol-5-yl)phenyl]-2,5-dimethylfuran-3-carboxamide;
N-[5-Chloro-2-(1H-tetrazol-5-yl)phenyl]pent-4-enamide;
N-[5-Chloro-2-(1H-tetrazol-5-yl)phenyl]cyclopropanecarboxamide;
5-Chloro-N-[5-chloro-2-(1H-tetrazol-5-yl)phenyl]-1-methyl-1H-pyrazole-4-carboxamide;
2-[(4-Chlorophenyl)oxy]-N-[5-chloro-2-(1H-tetrazol-5-yl)phenyl]acetamide;
2-[(3-Chlorophenyl)oxy]-N-[5-chloro-2-(1H-tetrazol-5-yl)phenyl]acetamide;
N-[5-Chloro-2-(1H-tetrazol-5-yl)phenyl]-2-{[3-(methyloxy)phenyl]oxy}acetamide;
N-[5-Chloro-2-(1H-tetrazol-5-yl)phenyl]-3-(phenyloxy)propanamide;
N-[5-Chloro-2-(1H-tetrazol-5-yl)phenyl]-3-[(4-fluorophenyl)oxy]propanamide;
N-[5-Chloro-2-(1H-tetrazol-5-yl)phenyl]cyclobutanecarboxamide; and
N-[5-Chloro-2-(1H-tetrazol-5-yl)phenyl]-2-{[2-(4-methylpiperazin-1-yl)phenyl]oxy}acetamide;
or a pharmaceutically acceptable salt thereof.

8. A pharmaceutical composition comprising a compound of claim 1, or a pharmaceutically acceptable salt thereof, and at least one pharmaceutically acceptable carrier, excipient or solvent.

9. A pharmaceutical composition comprising a compound of claim 2, or a pharmaceutically acceptable salt thereof, and at least one pharmaceutically acceptable carrier, excipient or solvent.

10. A pharmaceutical composition comprising a compound of claim 4, or a pharmaceutically acceptable salt thereof, and at least one pharmaceutically acceptable carrier, excipient or solvent.

* * * * *